(12) United States Patent
Damiano et al.

(10) Patent No.: US 11,357,911 B2
(45) Date of Patent: Jun. 14, 2022

(54) INFUSION PUMP AND SYSTEM FOR PREVENTING MISCHANNELING OF MULTIPLE MEDICAMENTS

(71) Applicant: Trustees of Boston University, Boston, MA (US)

(72) Inventors: Edward R. Damiano, Acton, MA (US); Kirk D. Ramey, Tallahassee, FL (US); Firas H. El-Khatib, Allston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/122,263

(22) Filed: Dec. 15, 2020

(65) Prior Publication Data
US 2021/0093777 A1   Apr. 1, 2021

Related U.S. Application Data

(63) Continuation of application No. 15/031,512, filed as application No. PCT/US2014/062186 on Oct. 24, 2014, now Pat. No. 10,881,789.
(Continued)

(51) Int. Cl.
*A61M 5/145* (2006.01)
*A61M 5/168* (2006.01)
(Continued)

(52) U.S. Cl.
CPC ........ *A61M 5/1452* (2013.01); *A61M 5/1413* (2013.01); *A61M 5/162* (2013.01);
(Continued)

(58) Field of Classification Search
CPC ........... A61M 2005/14208; A61M 2039/1094; A61M 2202/07; A61M 2205/14;
(Continued)

(56) References Cited

U.S. PATENT DOCUMENTS 1,930,929 A   10/1933   Eisenberg
3,807,467 A   4/1974    Tascher et al.
(Continued)

FOREIGN PATENT DOCUMENTS

CN   106061528 A   10/2016
EP   2 678 056     1/2014
(Continued)

OTHER PUBLICATIONS

Kolind et al., "Preservation-free drug for insulin pumps," Novo Nordisk Pharmaceutical company, Pump partner meeting ATTD 2020, WOP Technology Presentation, 26 pages.
(Continued)

*Primary Examiner* — Quynh-Nhu H. Vu
(74) *Attorney, Agent, or Firm* — BainwoodHuang

(57) ABSTRACT

A multi-medicament infusion system (10) for preventing the mischanneling of medicaments may include an infusion pump (12), medicament reservoirs (16A,16B), a multi-channel lumen (18), and an infusion set (20). The medicament reservoirs may be sized and shaped differently such that the medicament reservoirs can only be inserted into the infusion pump in a unique configuration. The multi-channel lumen may include connectors that mate to corresponding connectors on the infusion pump and the infusion set only in a unique configuration. Because the various parts of the multi-infusion system may only be connected in the unique configuration, the expected medicaments may be administered appropriately and channeled to the correct infusion sites.

22 Claims, 24 Drawing Sheets

Related U.S. Application Data

(60) Provisional application No. 61/895,279, filed on Oct. 24, 2013, provisional application No. 62/011,306, filed on Jun. 12, 2014, provisional application No. 61/932,835, filed on Jan. 29, 2014, provisional application No. 61/895,270, filed on Oct. 24, 2013, provisional application No. 61/895,288, filed on Oct. 24, 2013.

(51) Int. Cl.
*A61M 5/14* (2006.01)
*A61M 5/162* (2006.01)
*A61M 5/172* (2006.01)
*A61M 39/10* (2006.01)
*A61M 5/142* (2006.01)

(52) U.S. Cl.
CPC ...... *A61M 5/16831* (2013.01); *A61M 5/1723* (2013.01); *A61M 5/14248* (2013.01); *A61M 2005/14208* (2013.01); *A61M 2039/1094* (2013.01); *A61M 2202/07* (2013.01); *A61M 2205/14* (2013.01); *A61M 2205/18* (2013.01); *A61M 2205/276* (2013.01); *A61M 2205/52* (2013.01); *A61M 2205/6036* (2013.01); *A61M 2205/6045* (2013.01)

(58) Field of Classification Search
CPC ........ A61M 2205/18; A61M 2205/276; A61M 2205/52; A61M 2205/6036; A61M 2205/6045; A61M 5/1413; A61M 5/14248; A61M 5/1452; A61M 5/162; A61M 5/16831; A61M 5/1723
See application file for complete search history.

(56) References Cited

U.S. PATENT DOCUMENTS

| | | | |
|---|---|---|---|
| 4,150,673 A * | 4/1979 | Watt | A61M 5/162 |
| | | | 604/408 |
| 4,253,501 A | 3/1981 | Ogle | |
| 4,515,584 A * | 5/1985 | Abe | A61M 5/1723 |
| | | | 417/477.1 |
| 4,585,439 A | 4/1986 | Michel | |
| 4,608,042 A | 8/1986 | Vanderveen | |
| 4,675,006 A | 6/1987 | Hrushesky | |
| 5,085,643 A | 2/1992 | Larkin et al. | |
| 5,147,323 A * | 9/1992 | Haber | A61M 5/19 |
| | | | 604/191 |
| 5,243,982 A * | 9/1993 | Mostl | A61B 5/14532 |
| | | | 128/DIG. 12 |
| 5,298,023 A * | 3/1994 | Haber | A61M 5/2448 |
| | | | 604/191 |
| 5,356,380 A | 10/1994 | Hoekwater et al. | |
| 5,411,480 A | 5/1995 | Kriesel | |
| 5,472,403 A * | 12/1995 | Cornacchia | A61M 5/1407 |
| | | | 600/4 |
| 5,505,704 A * | 4/1996 | Pawelka | A61M 5/19 |
| | | | 604/191 |
| 5,522,803 A | 6/1996 | Teissen-Simony | |
| 5,529,463 A * | 6/1996 | Layer | F04B 19/022 |
| | | | 417/403 |
| 5,545,152 A | 8/1996 | Funderburk et al. | |
| 5,616,124 A | 4/1997 | Hague et al. | |
| 5,916,494 A | 6/1999 | Widman et al. | |
| 5,954,697 A | 9/1999 | Srisathapat et al. | |
| 5,961,494 A * | 10/1999 | Hogan | A01K 11/00 |
| | | | 604/191 |
| 5,971,972 A * | 10/1999 | Rosenbaum | A61J 1/10 |
| | | | 604/411 |
| 6,106,498 A | 8/2000 | Friedli et al. | |
| 6,132,416 A | 10/2000 | Broselow | |
| 6,248,067 B1 | 6/2001 | Causey, III et al. | |
| 6,259,587 B1 | 7/2001 | Sheldon et al. | |
| 6,360,784 B1 | 3/2002 | Philippens et al. | |
| 6,362,591 B1 | 3/2002 | Moberg | |
| 6,368,314 B1 | 4/2002 | Kipfer et al. | |
| 6,390,130 B1 | 5/2002 | Guala | |
| 6,485,465 B2 | 11/2002 | Moberg et al. | |
| 6,551,276 B1 | 4/2003 | Mann et al. | |
| 6,551,298 B1 | 4/2003 | Zhang et al. | |
| 6,554,798 B1 | 4/2003 | Mann et al. | |
| 6,555,986 B2 | 4/2003 | Moberg | |
| 6,558,320 B1 | 5/2003 | Causey, III et al. | |
| 6,572,545 B2 | 6/2003 | Knobbe et al. | |
| 6,585,695 B1 | 7/2003 | Adair et al. | |
| 6,620,138 B1 | 9/2003 | Marrgi et al. | |
| 6,641,533 B2 | 11/2003 | Causey, III et al. | |
| 6,652,483 B2 * | 11/2003 | Slate | A61M 5/30 |
| | | | 604/68 |
| 6,656,148 B2 | 12/2003 | Das et al. | |
| 6,659,980 B2 | 12/2003 | Moberg et al. | |
| 6,719,728 B2 | 4/2004 | Mason et al. | |
| 6,736,797 B1 | 5/2004 | Larsen et al. | |
| 6,752,787 B1 | 6/2004 | Causey, III et al. | |
| 6,801,420 B2 | 10/2004 | Talbot et al. | |
| 6,809,653 B1 | 10/2004 | Mann et al. | |
| 6,811,534 B2 | 11/2004 | Bowman et al. | |
| 6,821,421 B2 | 11/2004 | Murakami | |
| 6,854,620 B2 | 2/2005 | Ramey | |
| 6,872,200 B2 | 3/2005 | Mann et al. | |
| 6,878,132 B2 | 4/2005 | Kipfer | |
| 6,936,029 B2 | 8/2005 | Mann et al. | |
| 6,939,329 B1 | 9/2005 | Verkaart | |
| 6,958,705 B2 | 10/2005 | Lebel et al. | |
| 6,960,198 B2 | 11/2005 | Sarmiento | |
| 6,979,326 B2 | 12/2005 | Mann et al. | |
| 6,997,920 B2 | 2/2006 | Mann et al. | |
| 7,025,226 B2 | 4/2006 | Ramey | |
| 7,025,743 B2 | 4/2006 | Mann et al. | |
| 7,098,803 B2 | 8/2006 | Mann et al. | |
| 7,109,878 B2 | 9/2006 | Mann et al. | |
| 7,187,528 B2 | 3/2007 | Talbot et al. | |
| 7,193,521 B2 | 3/2007 | Moberg et al. | |
| 7,281,314 B2 | 10/2007 | Hess et al. | |
| 7,285,105 B2 | 10/2007 | Kim et al. | |
| 7,291,133 B1 | 11/2007 | Kindler et al. | |
| 7,324,012 B2 | 1/2008 | Mann et al. | |
| 7,342,508 B2 | 3/2008 | Morgan et al. | |
| 7,460,350 B2 | 12/2008 | Talbot et al. | |
| 7,534,226 B2 | 5/2009 | Mernoe et al. | |
| 7,602,310 B2 | 10/2009 | Mann et al. | |
| 7,621,893 B2 * | 11/2009 | Moberg | A61M 5/16854 |
| | | | 604/151 |
| 7,625,354 B2 | 12/2009 | Hochman | |
| 7,628,772 B2 | 12/2009 | McConnell et al. | |
| 7,628,782 B2 | 12/2009 | Adair et al. | |
| 7,648,494 B2 | 1/2010 | Kornerup et al. | |
| 7,654,127 B2 | 2/2010 | Krulevitch et al. | |
| 7,655,618 B2 | 2/2010 | Green et al. | |
| 7,658,734 B2 | 2/2010 | Adair et al. | |
| 7,678,762 B2 | 3/2010 | Green et al. | |
| 7,678,763 B2 | 3/2010 | Green et al. | |
| 7,683,027 B2 | 3/2010 | Green et al. | |
| 7,708,717 B2 | 5/2010 | Estes et al. | |
| 7,749,185 B2 * | 7/2010 | Wilson | A61M 1/3659 |
| | | | 604/43 |
| 7,760,481 B2 | 7/2010 | Talbot et al. | |
| 7,766,873 B2 | 8/2010 | Moberg et al. | |
| 7,776,030 B2 | 8/2010 | Estes et al. | |
| 7,789,859 B2 | 9/2010 | Estes et al. | |
| 7,794,427 B2 | 9/2010 | Estes et al. | |
| 7,794,428 B2 | 9/2010 | Estes et al. | |
| 7,815,602 B2 | 10/2010 | Mann et al. | |
| 7,819,843 B2 | 10/2010 | Mann et al. | |
| 7,831,310 B2 | 11/2010 | Lebel et al. | |
| 7,833,196 B2 | 11/2010 | Estes et al. | |
| 7,879,010 B2 | 2/2011 | Hunn et al. | |
| 7,879,026 B2 | 2/2011 | Estes et al. | |
| 7,887,512 B2 | 2/2011 | Estes et al. | |
| 7,892,206 B2 | 2/2011 | Moberg et al. | |
| 7,914,449 B2 | 3/2011 | Kouchi et al. | |

(56) References Cited

U.S. PATENT DOCUMENTS

| | | |
|---|---|---|
| 7,922,708 B2 | 4/2011 | Estes et al. |
| 7,951,112 B2 | 5/2011 | Patzer |
| 7,967,785 B2 | 6/2011 | Morgan et al. |
| 7,981,084 B2 | 7/2011 | Estes et al. |
| 7,981,105 B2 | 7/2011 | Adair et al. |
| 7,988,683 B2 | 8/2011 | Adair et al. |
| 7,998,111 B2 | 8/2011 | Moberg et al. |
| 7,998,131 B2 | 8/2011 | Adair et al. |
| 8,004,422 B2 | 8/2011 | Hess et al. |
| 7,938,803 B2 | 10/2011 | Mernoe et al. |
| 8,034,026 B2 | 10/2011 | Grant et al. |
| 8,057,436 B2 | 11/2011 | Causey et al. |
| 8,062,257 B2 | 11/2011 | Moberg et al. |
| 8,065,096 B2 | 11/2011 | Moberg et al. |
| 8,088,096 B2 | 1/2012 | Lauchard et al. |
| 8,105,279 B2 | 1/2012 | Mernoe et al. |
| 8,106,534 B2 | 1/2012 | Spurlin et al. |
| 8,142,397 B2 | 3/2012 | Patzer |
| 8,167,846 B2 | 5/2012 | Chong et al. |
| 8,177,767 B2 | 5/2012 | Kristensen et al. |
| 8,182,447 B2 | 5/2012 | Moberg et al. |
| 8,192,394 B2 | 6/2012 | Estes et al. |
| 8,197,444 B1 | 6/2012 | Bazargan et al. |
| 8,206,350 B2 | 6/2012 | Mann et al. |
| 8,206,353 B2 | 6/2012 | Chong et al. |
| 8,211,059 B2 | 7/2012 | Kriesel |
| 8,211,062 B2 | 7/2012 | Estes et al. |
| 8,251,959 B2 | 8/2012 | Johner et al. |
| 8,257,345 B2 | 9/2012 | Adair et al. |
| 8,267,893 B2 | 9/2012 | Moberg et al. |
| 8,273,061 B2 | 9/2012 | McConnell et al. |
| 8,282,601 B2 | 10/2012 | Mernoe et al. |
| 8,287,495 B2 | 10/2012 | Michaud et al. |
| 8,287,516 B2 | 10/2012 | Kornerup et al. |
| 8,298,184 B2 | 10/2012 | DiPerna et al. |
| 8,303,572 B2 | 11/2012 | Adair et al. |
| 8,372,039 B2 | 2/2013 | Mernoe et al. |
| 8,409,142 B2 | 4/2013 | Causey et al. |
| 8,430,847 B2 | 4/2013 | Mernoe et al. |
| 8,430,849 B2 | 4/2013 | Smith et al. |
| 8,454,575 B2 | 6/2013 | Estes et al. |
| 8,469,942 B2 | 6/2013 | Kow et al. |
| 8,475,408 B2 | 7/2013 | Mernoe et al. |
| 8,480,623 B2 | 7/2013 | Mernoe et al. |
| 8,483,980 B2 | 7/2013 | Moberg et al. |
| 8,500,716 B2 | 8/2013 | Adair et al. |
| 8,512,276 B2 | 8/2013 | Talbot et al. |
| 8,512,289 B2 | 8/2013 | Chong et al. |
| 8,523,803 B1 | 9/2013 | Favreau |
| 8,551,045 B2 | 10/2013 | Sie et al. |
| 8,551,046 B2 | 10/2013 | Causey et al. |
| 8,556,856 B2 | 10/2013 | Bazargan et al. |
| 8,556,866 B2 | 10/2013 | Krulevitch et al. |
| 8,562,565 B2 | 10/2013 | Fonacier et al. |
| 8,562,587 B2 | 10/2013 | Kovatchev et al. |
| 8,568,349 B2 | 10/2013 | Shergold |
| 8,573,027 B2 | 11/2013 | Rosinko et al. |
| 8,579,813 B2 | 11/2013 | Causey, III et al. |
| 8,597,269 B2 | 12/2013 | Chong et al. |
| 8,603,026 B2 | 12/2013 | Favreau |
| 8,603,027 B2 | 12/2013 | Favreau |
| 8,603,033 B2 | 12/2013 | Bazargan et al. |
| 8,613,726 B2 | 12/2013 | Causey, III et al. |
| 8,613,731 B2 | 12/2013 | Hansen et al. |
| 8,617,110 B2 | 12/2013 | Moberg et al. |
| 8,622,966 B2 | 1/2014 | Causey, III et al. |
| 8,628,510 B2 | 1/2014 | Bazargan et al. |
| 8,641,671 B2 | 2/2014 | Michaud et al. |
| 8,647,074 B2 | 2/2014 | Moberg et al. |
| 8,647,296 B2 | 2/2014 | Moberg et al. |
| 8,663,103 B2 | 3/2014 | Causey, III et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,696,633 B2 | 4/2014 | Estes et al. |
| 8,747,368 B2 | 6/2014 | Mernoe et al. |
| 8,747,369 B2 | 6/2014 | Mernoe et al. |
| 8,758,323 B2 | 6/2014 | Michaud et al. |
| 8,771,229 B2 | 7/2014 | Amirouche et al. |
| 8,777,901 B2 | 7/2014 | Smith et al. |
| 8,790,307 B2 | 7/2014 | Amirouche et al. |
| 8,821,442 B2 | 9/2014 | Haaar |
| 8,823,528 B2 | 9/2014 | Blomquist |
| 8,834,420 B2 | 9/2014 | Estes et al. |
| 8,841,012 B2 | 9/2014 | Fonacier et al. |
| 8,864,726 B2 | 10/2014 | Halili et al. |
| 8,864,737 B2 | 10/2014 | Hasegawa et al. |
| 8,864,739 B2 | 10/2014 | Moberg et al. |
| 8,870,829 B2 | 10/2014 | Halili et al. |
| 8,876,770 B2 * | 11/2014 | Kraft ............... A61M 5/14244 604/152 |
| 8,900,206 B2 | 12/2014 | Halili et al. |
| 8,905,972 B2 | 12/2014 | Smith et al. |
| 8,915,879 B2 | 12/2014 | Smith et al. |
| 8,936,573 B2 | 1/2015 | Blomquist |
| 8,945,068 B2 | 2/2015 | Halili et al. |
| 8,974,435 B2 | 3/2015 | Friedli |
| 8,992,475 B2 | 3/2015 | Mann et al. |
| 8,992,507 B2 | 3/2015 | Aeschlimann et al. |
| 8,998,840 B2 | 4/2015 | Hanson et al. |
| 8,998,842 B2 | 4/2015 | Lauchard et al. |
| 8,998,856 B2 * | 4/2015 | Eggert ............... A61M 5/2448 604/191 |
| 8,998,858 B2 | 4/2015 | Chong et al. |
| 9,011,371 B2 | 4/2015 | Moberg et al. |
| 9,033,925 B2 | 5/2015 | Moberg et al. |
| 9,033,951 B2 | 5/2015 | Kow et al. |
| 9,050,406 B2 | 6/2015 | Kow et al. |
| 9,101,710 B2 | 8/2015 | Yavorsky et al. |
| 9,101,715 B2 | 8/2015 | Causey, III et al. |
| 9,107,999 B2 | 8/2015 | Moberg et al. |
| 9,114,209 B2 | 8/2015 | Estes et al. |
| 9,114,213 B2 | 8/2015 | Murakami et al. |
| 9,119,917 B2 | 9/2015 | Blomquist |
| 9,132,228 B2 | 9/2015 | Yan |
| 9,173,998 B2 | 11/2015 | Rosinko et al. |
| 9,180,242 B2 | 11/2015 | Metzmaker et al. |
| 9,180,243 B2 | 11/2015 | Michaud |
| 9,180,254 B2 | 11/2015 | Avery et al. |
| 9,184,490 B2 | 11/2015 | Crouther et al. |
| 9,194,388 B2 | 11/2015 | Laermer |
| 9,205,192 B2 | 12/2015 | Estes et al. |
| 9,211,376 B2 | 12/2015 | Kouyoumjian et al. |
| 9,211,377 B2 | 12/2015 | DiPerna et al. |
| 9,216,249 B2 | 12/2015 | Smith et al. |
| 9,220,835 B2 * | 12/2015 | Cane' ............... A61M 5/1422 |
| 9,250,106 B2 | 2/2016 | Rosinko et al. |
| 9,272,009 B2 | 3/2016 | Spencer |
| 9,283,318 B2 | 3/2016 | Yavorsky et al. |
| 9,295,826 B2 | 3/2016 | Bertrand et al. |
| 9,308,320 B2 | 4/2016 | Smith et al. |
| 9,308,321 B2 | 4/2016 | Alderete et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,335,910 B2 | 5/2016 | Farnan et al. |
| 9,339,639 B2 | 5/2016 | Halili et al. |
| 9,344,024 B2 | 5/2016 | Favreau |
| 9,345,643 B2 | 5/2016 | Okiyama |
| 9,364,608 B2 | 6/2016 | Moberg et al. |
| 9,379,652 B2 | 6/2016 | Favreau |
| 9,379,653 B2 | 6/2016 | Favreau |
| 9,381,297 B2 | 7/2016 | Brown et al. |
| 9,381,300 B2 | 7/2016 | Smith et al. |
| 9,393,399 B2 | 7/2016 | Yavorsky et al. |
| 9,415,157 B2 | 8/2016 | Mann et al. |
| 9,427,519 B2 | 8/2016 | Kraft et al. |
| 9,433,731 B2 | 9/2016 | Trock et al. |
| 9,433,732 B2 | 9/2016 | Moberg et al. |
| 9,433,733 B2 | 9/2016 | Moberg et al. |
| 9,452,255 B2 | 9/2016 | Tieck et al. |
| 9,452,256 B2 | 9/2016 | Tieck et al. |
| 9,463,309 B2 | 10/2016 | Yavorsky et al. |
| 9,494,147 B2 | 11/2016 | Chong et al. |

(56) References Cited

U.S. PATENT DOCUMENTS

| | | | |
|---|---|---|---|
| 9,498,573 B2 | 11/2016 | Smith et al. | |
| 9,514,518 B2 | 12/2016 | Gillespie et al. | |
| 9,517,299 B2 | 12/2016 | Tieck et al. | |
| 9,517,301 B2 | 12/2016 | Estes et al. | |
| 9,533,132 B2 | 1/2017 | Halili et al. | |
| 9,539,385 B2 | 1/2017 | Mathys | |
| 9,539,388 B2 | 1/2017 | Causey et al. | |
| 9,554,967 B2 | 1/2017 | Moia et al. | |
| 9,579,452 B2 | 2/2017 | Adair et al. | |
| 9,592,339 B2 | 3/2017 | Zhou | |
| 9,597,462 B2 | 3/2017 | Moore | |
| 9,610,431 B2 | 4/2017 | Halili et al. | |
| 9,629,992 B2 | 4/2017 | Halili et al. | |
| 9,636,453 B2 | 5/2017 | Monirabbasi et al. | |
| 9,682,189 B2 | 6/2017 | Good et al. | |
| 9,687,612 B2 | 6/2017 | Avery et al. | |
| 9,707,339 B2 * | 7/2017 | Chartrand | A61M 1/3659 |
| 9,715,327 B2 | 7/2017 | Rosinko et al. | |
| 9,717,845 B2 | 8/2017 | Istoc | |
| 9,717,848 B2 | 8/2017 | Geismar et al. | |
| 9,731,067 B2 | 8/2017 | Pananen | |
| 9,744,290 B2 | 8/2017 | Tieck et al. | |
| 9,744,291 B2 | 8/2017 | Tieck et al. | |
| 9,744,301 B2 | 8/2017 | Mann et al. | |
| 9,750,871 B2 | 9/2017 | Metzmaker et al. | |
| 9,750,873 B2 | 9/2017 | Brown et al. | |
| 9,750,875 B2 | 9/2017 | Smith et al. | |
| 9,770,553 B2 | 9/2017 | Bazargan et al. | |
| 9,782,543 B2 | 10/2017 | Groeschke et al. | |
| 9,789,245 B2 | 10/2017 | Tieck et al. | |
| 9,795,732 B2 | 10/2017 | Trock et al. | |
| 9,801,787 B2 | 10/2017 | Py | |
| 9,814,830 B2 | 11/2017 | Mernoe et al. | |
| 9,814,872 B2 | 11/2017 | Eggert et al. | |
| 9,839,741 B2 | 12/2017 | Yavorsky et al. | |
| 9,841,014 B2 | 12/2017 | Yap et al. | |
| 9,863,837 B2 | 1/2018 | Rule et al. | |
| 9,872,957 B2 | 1/2018 | Causey et al. | |
| 9,883,834 B2 | 2/2018 | Amirouche et al. | |
| 9,889,256 B2 | 2/2018 | Cabiri et al. | |
| 9,895,490 B2 | 2/2018 | Kow et al. | |
| 9,925,330 B2 | 3/2018 | Tieck et al. | |
| 9,931,459 B2 | 4/2018 | Tieck et al. | |
| 9,931,460 B2 | 4/2018 | Tieck et al. | |
| 9,943,645 B2 | 4/2018 | Monirabbasi et al. | |
| 9,950,113 B2 | 4/2018 | Franke et al. | |
| 9,987,420 B2 | 6/2018 | Pananen | |
| 9,993,592 B2 | 6/2018 | Amirouche et al. | |
| 9,993,594 B2 | 6/2018 | Bazargan et al. | |
| 10,010,674 B2 | 7/2018 | Rosinko et al. | |
| 10,010,678 B2 | 7/2018 | Schildt et al. | |
| 10,016,564 B2 | 7/2018 | Piehl et al. | |
| 10,029,045 B2 | 7/2018 | Smith et al. | |
| 10,064,993 B2 | 9/2018 | Mernoe et al. | |
| 10,071,200 B2 | 9/2018 | Alderete et al. | |
| 10,080,839 B2 | 9/2018 | Cole et al. | |
| 10,086,133 B2 | 10/2018 | Pananen et al. | |
| 10,086,134 B2 | 10/2018 | Pananen et al. | |
| 10,092,701 B2 | 10/2018 | Johansen et al. | |
| 10,105,483 B2 | 10/2018 | Mernoe | |
| 10,105,497 B2 | 10/2018 | Dreier et al. | |
| 10,130,759 B2 | 11/2018 | Amirouche et al. | |
| 10,130,763 B2 | 11/2018 | Lauchard et al. | |
| 10,137,243 B2 | 11/2018 | Wang et al. | |
| 10,141,882 B2 | 11/2018 | Favreau | |
| 10,146,911 B2 | 12/2018 | Trock | |
| 10,166,327 B2 | 1/2019 | Tieck et al. | |
| 10,172,998 B2 | 1/2019 | Tieck et al. | |
| 10,172,999 B2 | 1/2019 | Tieck et al. | |
| 10,207,047 B2 | 2/2019 | Estes | |
| 10,213,549 B2 | 2/2019 | Amirouche et al. | |
| 10,220,143 B2 | 3/2019 | Moberg et al. | |
| 10,228,663 B2 | 3/2019 | Favreau | |
| 10,232,109 B2 | 3/2019 | Deak et al. | |
| 10,238,030 B2 | 3/2019 | Urbani | |
| 10,238,793 B2 | 3/2019 | Deak et al. | |
| 10,252,001 B2 | 4/2019 | Geismar et al. | |
| 10,258,736 B2 | 4/2019 | Metzmaker et al. | |
| 10,272,196 B2 | 4/2019 | Smith et al. | |
| 10,279,110 B2 | 5/2019 | Mann et al. | |
| 10,300,264 B2 | 5/2019 | Halili et al. | |
| 10,307,536 B2 | 6/2019 | Causey et al. | |
| 10,322,227 B2 | 6/2019 | Piehl et al. | |
| 10,363,365 B2 | 7/2019 | Bazargan | |
| 10,376,631 B2 | 8/2019 | Tieck et al. | |
| 10,376,632 B2 | 8/2019 | Tieck et al. | |
| 10,384,013 B2 | 8/2019 | Krusell et al. | |
| 10,391,257 B2 | 8/2019 | Piehl et al. | |
| 10,478,554 B2 | 11/2019 | Bazargan et al. | |
| 10,517,892 B2 | 12/2019 | Chattaraj et al. | |
| 10,532,156 B2 | 1/2020 | Istoc | |
| 10,552,580 B2 | 2/2020 | Bazargan | |
| 10,603,431 B2 | 3/2020 | Mernoe et al. | |
| 10,772,796 B2 | 9/2020 | Kavazov | |
| 10,850,032 B2 | 12/2020 | Steck et al. | |
| 10,857,287 B2 | 12/2020 | Damiano et al. | |
| 10,861,591 B2 | 12/2020 | Grosman et al. | |
| 10,881,789 B2 | 1/2021 | Damiano et al. | |
| 10,960,136 B2 | 3/2021 | Palerm et al. | |
| 2002/0019608 A1 * | 2/2002 | Mason | A61M 5/1424 604/133 |
| 2002/0038392 A1 | 3/2002 | De La Huerga | |
| 2002/0055711 A1 | 5/2002 | Lavi et al. | |
| 2002/0065484 A1 * | 5/2002 | Douglas | A61M 5/158 604/93.01 |
| 2002/0161332 A1 | 10/2002 | Ramey | |
| 2003/0009133 A1 | 1/2003 | Ramey | |
| 2005/0015056 A1 | 1/2005 | Duchon et al. | |
| 2005/0020980 A1 | 1/2005 | Inoue | |
| 2005/0038387 A1 * | 2/2005 | Kriesel | A61M 5/16827 604/133 |
| 2005/0051580 A1 | 3/2005 | Ramey | |
| 2005/0154434 A1 | 7/2005 | Simon et al. | |
| 2005/0256461 A1 * | 11/2005 | DiFiore | A61M 39/105 604/247 |
| 2006/0264908 A1 | 11/2006 | Ishii et al. | |
| 2007/0088271 A1 * | 4/2007 | Richards | A61M 5/14244 604/151 |
| 2007/0142786 A1 | 6/2007 | Lampropoulos et al. | |
| 2007/0161955 A1 | 7/2007 | Bynum et al. | |
| 2007/0273671 A1 | 11/2007 | Zadesky et al. | |
| 2007/0282294 A1 | 12/2007 | Sidler | |
| 2008/0051719 A1 | 2/2008 | Moberg | |
| 2008/0188813 A1 | 8/2008 | Miller et al. | |
| 2008/0243085 A1 | 10/2008 | DeStefano | |
| 2008/0262425 A1 | 10/2008 | Mogensen | |
| 2008/0319383 A1 * | 12/2008 | Byland | A61M 5/31551 604/67 |
| 2009/0326506 A1 | 12/2009 | Hasegawa et al. | |
| 2010/0049144 A1 | 2/2010 | McConnell et al. | |
| 2010/0145303 A1 * | 6/2010 | Yodfat | A61M 5/14228 604/506 |
| 2010/0191165 A1 | 7/2010 | Appling et al. | |
| 2010/0217241 A1 | 8/2010 | Mann et al. | |
| 2011/0021905 A1 | 1/2011 | Patrick et al. | |
| 2011/0118659 A1 * | 5/2011 | Maaskamp | A61M 39/223 604/28 |
| 2011/0230838 A1 | 9/2011 | Adams et al. | |
| 2011/0288494 A1 | 11/2011 | Mendels | |
| 2012/0078185 A1 | 3/2012 | Smith | |
| 2012/0078197 A1 | 5/2012 | O'Connor et al. | |
| 2012/0211946 A1 | 8/2012 | Halili et al. | |
| 2012/0211947 A1 | 8/2012 | Halili et al. | |
| 2012/0215177 A1 | 8/2012 | Halili et al. | |
| 2012/0215178 A1 | 8/2012 | Halili et al. | |
| 2012/0215179 A1 | 8/2012 | Halili et al. | |
| 2012/0215180 A1 | 8/2012 | Halili et al. | |
| 2012/0215183 A1 | 8/2012 | Halili et al. | |
| 2012/0226234 A1 | 9/2012 | Bazargan et al. | |
| 2013/0046253 A1 | 2/2013 | Yavorsky et al. | |
| 2013/0085470 A1 | 4/2013 | O'Connor et al. | |
| 2013/0245604 A1 | 9/2013 | Kouyoumjian et al. | |

(56) References Cited

U.S. PATENT DOCUMENTS

| | | | |
|---|---|---|---|
| 2013/0345641 A1* | 12/2013 | German | A61M 5/24 604/189 |
| 2015/0057615 A1 | 2/2015 | Mernoe, V et al. | |
| 2015/0073384 A1* | 3/2015 | Limaye | A61M 5/1452 604/506 |
| 2015/0202375 A1 | 7/2015 | Schabbach et al. | |
| 2015/0265826 A1 | 9/2015 | Dudley | |
| 2015/0314063 A1 | 11/2015 | Nagar et al. | |
| 2015/0357683 A1 | 12/2015 | Lohr | |
| 2016/0015885 A1 | 1/2016 | Pananen et al. | |
| 2016/0015886 A1 | 1/2016 | Pananen et al. | |
| 2016/0015887 A1 | 1/2016 | Pananen et al. | |
| 2016/0015911 A1 | 1/2016 | Bazargan et al. | |
| 2016/0051760 A1 | 2/2016 | Krusell et al. | |
| 2016/0058668 A1 | 3/2016 | Metzmaker et al. | |
| 2016/0074587 A1 | 3/2016 | Searle et al. | |
| 2016/0082182 A1 | 3/2016 | Gregory et al. | |
| 2016/0089493 A1 | 3/2016 | Crouther et al. | |
| 2016/0106919 A1 | 4/2016 | Hayter et al. | |
| 2016/0184519 A1* | 6/2016 | Blundred | A61M 5/16827 604/89 |
| 2016/0220754 A1 | 8/2016 | Shaanan et al. | |
| 2016/0263324 A1 | 9/2016 | Shaanan et al. | |
| 2016/0271322 A1 | 9/2016 | Ramey | |
| 2016/0361494 A1 | 12/2016 | Jurg et al. | |
| 2017/0056590 A1 | 3/2017 | DiPerna | |
| 2017/0065768 A1 | 3/2017 | Moore | |
| 2017/0182307 A1 | 6/2017 | Halili et al. | |
| 2017/0189666 A1 | 7/2017 | Sealfon et al. | |
| 2017/0192506 A1 | 7/2017 | Andersen et al. | |
| 2017/0216523 A1 | 8/2017 | Neftel et al. | |
| 2017/0235920 A1 | 8/2017 | Bauss et al. | |
| 2017/0239422 A1 | 8/2017 | Kodgule et al. | |
| 2017/0286638 A1 | 10/2017 | Searle et al. | |
| 2017/0312454 A1 | 11/2017 | Chattaraj et al. | |
| 2018/0036475 A1 | 2/2018 | Lin | |
| 2018/0043104 A1 | 2/2018 | Mueller-Pathle | |
| 2018/0043105 A1 | 2/2018 | Nazzaro et al. | |
| 2018/0103897 A1 | 4/2018 | Amirouche | |
| 2018/0104417 A1 | 4/2018 | Nessel et al. | |
| 2018/0117248 A1 | 6/2018 | Cabiri et al. | |
| 2018/0117296 A1 | 6/2018 | Damiano et al. | |
| 2018/0207366 A1 | 7/2018 | Marcoz et al. | |
| 2018/0228979 A1 | 8/2018 | Schildt et al. | |
| 2018/0280624 A1 | 10/2018 | Bitton et al. | |
| 2018/0311435 A1 | 11/2018 | Galasso | |
| 2018/0318498 A1 | 11/2018 | Grant et al. | |
| 2018/0318506 A1 | 11/2018 | Oakes et al. | |
| 2018/0326164 A1 | 11/2018 | Bauss et al. | |
| 2018/0353699 A1 | 12/2018 | Helmer et al. | |
| 2019/0001060 A1 | 1/2019 | Gylleby et al. | |
| 2019/0009032 A1 | 1/2019 | Hautaviita et al. | |
| 2019/0015582 A1 | 1/2019 | Naftalovitz et al. | |
| 2019/0030247 A1 | 1/2019 | Edwards et al. | |
| 2019/0054251 A1 | 2/2019 | Pieronek et al. | |
| 2019/0091460 A1 | 3/2019 | Yavorsky et al. | |
| 2019/0134305 A1 | 5/2019 | Srinivasan et al. | |
| 2019/0151559 A1 | 5/2019 | Byerly et al. | |
| 2019/0167900 A1 | 6/2019 | Friedli et al. | |
| 2019/0192762 A1 | 6/2019 | Metzmaker et al. | |
| 2019/0209775 A1 | 7/2019 | Merchant | |
| 2019/0217007 A1 | 7/2019 | Sasaki | |
| 2020/0330719 A1 | 10/2020 | Segal | |
| 2021/0030949 A1 | 2/2021 | Damiano et al. | |
| 2021/0030957 A1 | 2/2021 | Damiano et al. | |
| 2021/0106750 A1 | 4/2021 | Damiano et al. | |
| 2021/0283328 A1 | 9/2021 | Damiano et al. | |

FOREIGN PATENT DOCUMENTS

| | | | |
|---|---|---|---|
| EP | 3 060 276 | 8/2016 | |
| EP | 3 060 277 | 8/2016 | |
| EP | 3 062 841 | 9/2016 | |
| EP | 3 150 241 | 6/2018 | |
| EP | 3 378 516 | 9/2018 | |
| EP | 3 319 662 | 3/2019 | |
| HK | 1230529 | 12/2017 | |
| HK | 1254602 A | 7/2019 | |
| JP | 57-124151 | 8/1982 | |
| JP | 59-30241 | 2/1984 | |
| JP | 2004-538118 | 12/2004 | |
| JP | 2007-511252 | 5/2007 | |
| JP | 2013-524905 | 6/2013 | |
| JP | 2014-515673 | 7/2014 | |
| JP | 2016-538098 | 8/2016 | |
| JP | 2018-525060 | 9/2018 | |
| RU | 2549310 | 4/2015 | |
| WO | WO 99/64103 | 12/1999 | |
| WO | WO 04/045704 | 6/2004 | |
| WO | WO 05/004973 | 1/2005 | |
| WO | WO 06/054367 | 5/2006 | |
| WO | WO-2007075677 A2 * | 7/2007 | A61M 5/1782 |
| WO | WO 09/069511 | 4/2009 | |
| WO | WO 07/086186 | 5/2009 | |
| WO | WO 09/060741 | 5/2009 | |
| WO | WO 12/008285 | 1/2012 | |
| WO | WO 12/072555 | 6/2012 | |
| WO | WO 12/110474 | 8/2012 | |
| WO | WO 12/0115911 | 8/2012 | |
| WO | WO 12/160104 | 11/2012 | |
| WO | WO 13/161979 | 10/2013 | |
| WO | WO 14/104027 | 3/2014 | |
| WO | WO 15/061690 | 4/2015 | |
| WO | WO 15/061691 | 4/2015 | |
| WO | WO 15/061693 | 4/2015 | |
| WO | WO 15/155229 | 10/2015 | |
| WO | WO 15/166993 | 11/2015 | |
| WO | WO 17/007968 | 1/2017 | |
| WO | WO 17/199012 | 11/2017 | |
| WO | WO 17/217105 | 12/2017 | |
| WO | WO 18/129354 | 7/2018 | |
| WO | WO 19/021985 | 1/2019 | |
| WO | WO 19/046593 | 3/2019 | |

OTHER PUBLICATIONS

Ping One Touch Owner's Booklet, Dated Oct. 2014, (360 pages).
Renesas Synergy™ Platform, "Capacitive Touch Hardware Design and Layout Guidelines for Synergy, RX200, and RX100." R01AN3825EU0101 Rev.1.01, Jun. 14, 2017, pp. 1-18.
International Preliminary Report on Patentability, PCT/US2014/062187, dated Apr. 26, 2016, 6 pages.
International Preliminary Report on Patentability, PCT/US2014/062189, dated Apr. 26, 2016, 7 pages.
International Preliminary Report on Patentability, PCT/US2014/062186, dated Apr. 26, 2016, 6 pages.
International Search Report and Written Opinion, PCT2014/062186, dated Feb. 18, 2015, 9 pages.
International Search Report and Written Opinion, PCT2014/062187, dated Feb. 24, 2015, 10 pages.
International Search Report and Written Opinion, PCT2014/062189, dated Feb. 24, 2015, 11 pages.
Boston University, Jan. 2014, Bionic Pancreas: Introducing the iLet 1294 1000, http://sites.bu.edu/bionicpacreas/introducing-the-ilet-1294-1000/, 3 pp.
Brown et al., Apr. 1, 2016, Introducing Beta Bionics: bringing the iLet bionic pancreas to market, https://diatribe.org/introducing-beta-bionics-bringing-ilet-bionic-pancreas-marekt, 3 pp.
Hoskins, Oct. 2, 2018, iLet "Bionic Pancreas" making progress with gen 4 device, Healthline, https//www.healthline.com/diabetesmine/beta-bionics-ilet-update#1, 15 pp.
Idlebrook, Jul. 30, 2019, Beta Bionics secures funding for pivotal ILet bionic pancreas trials, https://t1dexchange.org/welcome-glu-users/articles/beta-bionics-secures-funding-for-pivotal-ilet-bionic-pancreas-trials, 4 pp.
Krugman, Aug. 25, 2018, iLet Bionic Pancreas Interface, sarakrugman.com/ilet-interface, 3 pp.

(56) References Cited

OTHER PUBLICATIONS

Sifferlin, Apr. 1, 2016, The bionic pancreas is getting closer to reality, time.com, https://time.com/4278068/bionic-pancreas-company, 5 pp.

* cited by examiner

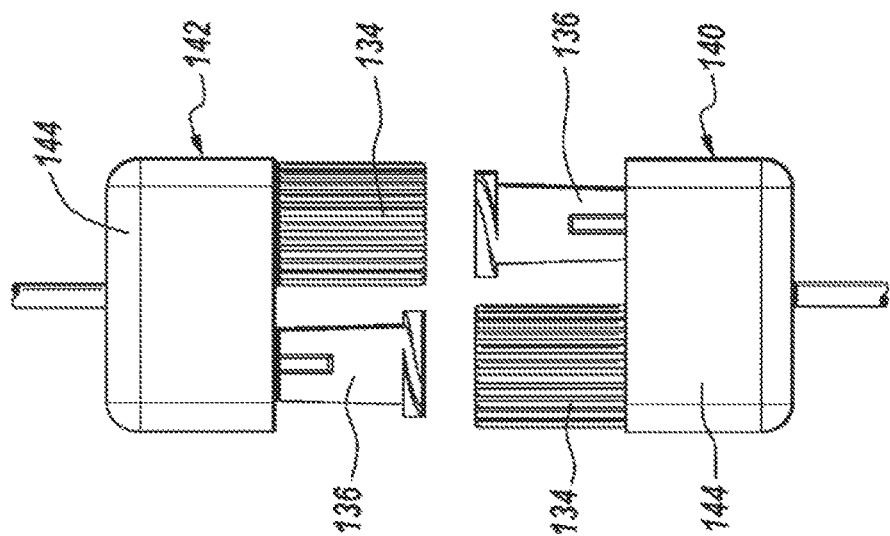
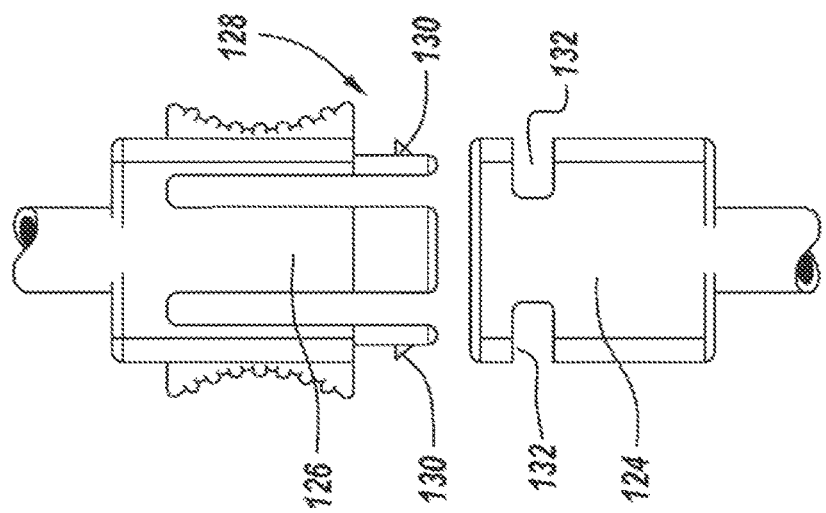
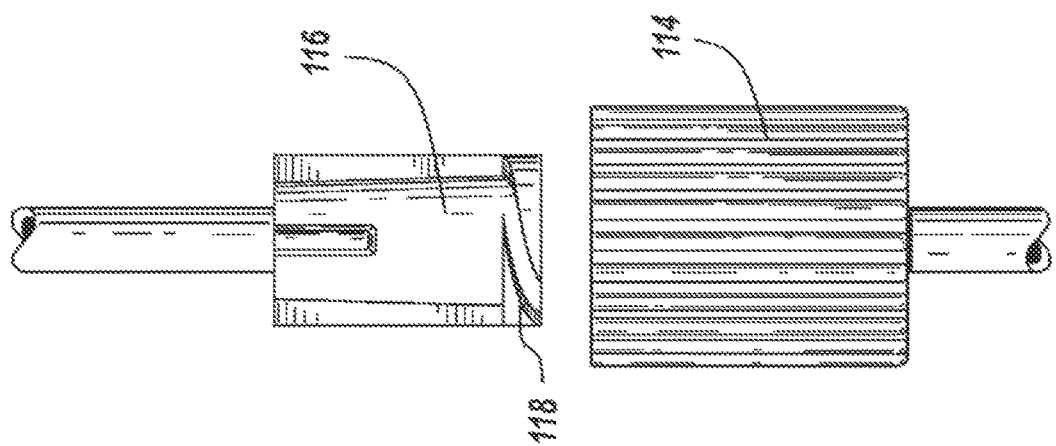
Fig. 8C
Fig. 8B
Fig. 8A

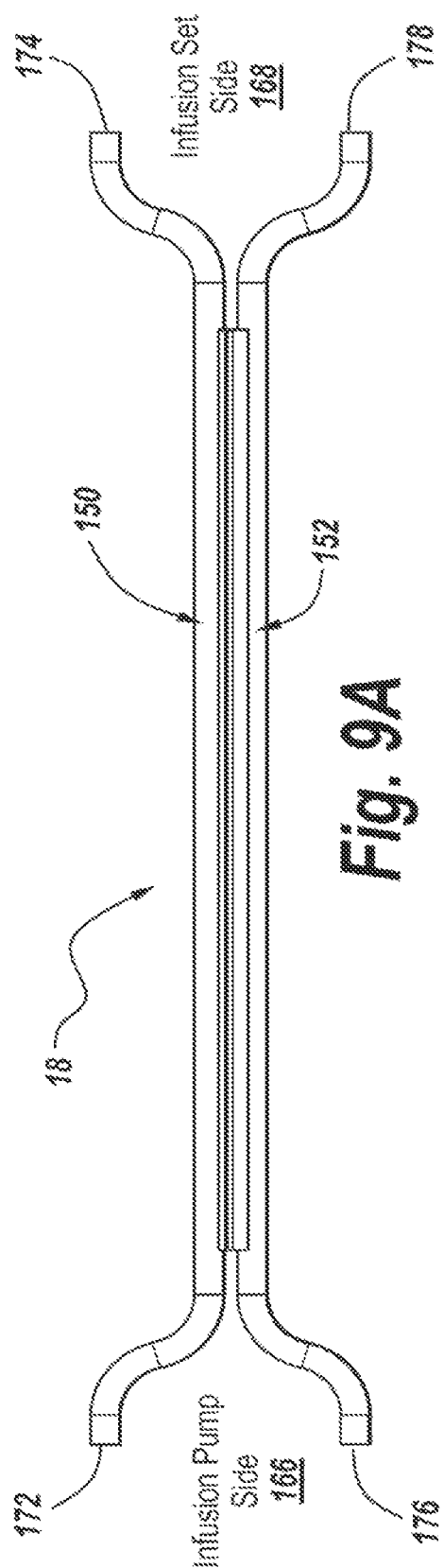
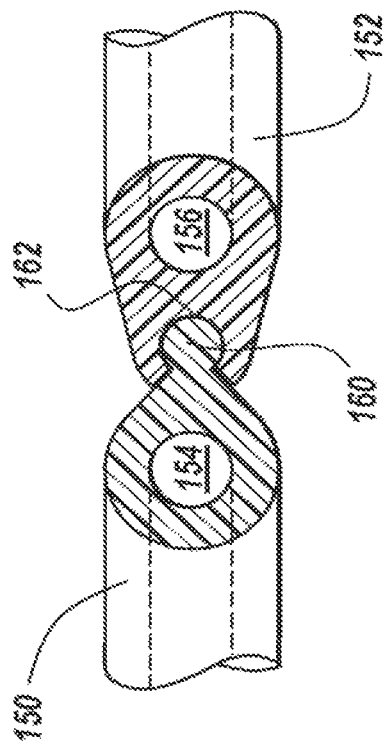

INFUSION PUMP AND SYSTEM FOR PREVENTING MISCHANNELING OF MULTIPLE MEDICAMENTS

INCORPORATION BY REFERENCE TO ANY PRIORITY APPLICATIONS

This application is a continuation of U.S. application Ser. No. 15/031,512, filed Apr. 22, 2016, which is a 35 U.S.C. 371 national stage filing of International Application PCT/US2014/062186, filed Oct. 24, 2014, which claims priority to U.S. Provisional Application No. 61/895,270 filed on Oct. 24, 2013, U.S. Provisional Application No. 61/895,279, filed Oct. 24, 2013, U.S. Provisional Application No. 61/895,288, filed Oct. 24, 2013, U.S. Provisional Patent Application No. 61/932,835 filed Jan. 29, 2014, and U.S. Provisional Application No. 62/011,306 filed Jun. 12, 2014, in the United States. The contents of the aforementioned applications are hereby incorporated by reference in their entireties.

STATEMENT REGARDING FEDERALLY SPONSORED RESEARCH AND DEVELOPMENT

This invention was made with government support under Contract No. DK085633 awarded by the National Institutes of Health. The government has certain rights in the invention.

RELATED APPLICATIONS

This application claims priority to the following US patent applications: U.S. Patent Application No. 61/895,270, filed on Oct. 24, 2013 and entitled "Manifold for the Transferral of Medicaments from Different Vials Without Mis-Channeling;" U.S. Patent Application No. 61/895,279, filed on Oct. 24, 2013 and entitled "Device for Bridging Infusion Sources With Sites of Infusion in a Multi-Channel Infusion System of Two Medicaments;" U.S. Patent Application No. 61/895,288, filed on Oct. 24, 2013 and entitled "Infusion Set or Administration Set for Infusing Two or More Medicaments via an Array of Multiple Catheters or Canulae;" U.S. Patent Application No. 61/932,835, filed on Jan. 29, 2014 and entitled "Multi-infusion Device that allows Unique Loading of Vials for Delivery of Medicaments Without Mis-Channeling;" and U.S. Patent Application No. 62/011,306, filed on Jun. 12, 2014 and entitled "Infusion System for Preventing Mischanneling of Multiple Medicaments." The contents of the aforementioned applications are incorporated herein by reference.

BACKGROUND OF THE INVENTION

Field of the Invention

The present invention relates to a system and method for administering medicaments to a diabetic patient. More particularly, the present invention relates to system and method of preventing the mischanneling of medicaments so as to avoid the accidental administration of the wrong medicament to the diabetic patient.

Background of the Invention

Diabetes mellitus, often referred to as diabetes, is a chronic condition in which a person has elevated blood glucose levels that result from defects in the body's ability to produce and/or use insulin. There are three main types of diabetes. Type 1 diabetes is a condition wherein the body does not produce insulin and therefore cannot control the amount of sugar in the blood stream. This type of diabetes can be autoimmune, genetic, and/or environmental and usually strikes children and young adults. Type 2 diabetes is a condition wherein the body does not produce or use insulin normally. This type of diabetes accounts for between 90-95% of diabetes cases and is linked to obesity and physical inactivity. Gestational diabetes is a form of glucose intolerance diagnosed during pregnancy and usually resolves spontaneously after delivery.

Insulin is used to control blood sugar in people who have Type 1 and Type 2 diabetes. Insulin is a hormone that helps keep blood glucose levels on target by moving glucose from the blood into the cells of the body. The cells then use glucose for energy. In people who do not have diabetes, the body produces the correct amount of Insulin on its own, whereas the bodies of diabetics do not. There are different types of insulin but they differ only in how quickly they begin to work and how long they continue to control blood sugar or glucose. Insulin is usually needed several times a day, and more than one type of insulin may be needed. Insulin helps control high blood sugar but unfortunately does not cure diabetes.

The number of diagnosed cases of diabetes continues to increase in the U.S. and throughout the world, creating enormous economic and public health consequences. Devices and therapies that improve the quality of life for the diabetic patient are important not only for the patient, but for society at large. One area in which recently developed technologies have been able to improve the standard of care has been in the maintenance of tight control over blood glucose levels. It is well known that if a diabetic patient's blood glucose values can be maintained in a relatively narrow and normal range (e.g., between about 80 milligrams per deciliter (mg/dL) to about 120 mg/dL) the physiologically damaging consequences of unchecked diabetes can be minimized.

Diabetes is managed primarily by controlling the level of glucose in the bloodstream. This level is dynamic and complex and is affected by multiple factors including the amount and type of food consumed and the amount of insulin (which mediates the transport of glucose across cell membranes) in the blood. Blood glucose levels are also sensitive to many different types of things, such as exercise, sleep, stress, smoking, travel, illness, and other psychological and lifestyle factors unique to individual patients. With better blood glucose information, diabetic patients can better control their blood glucose level through a variety of means, including diet, exercise, and medication. For this reason a large industry has developed to provide the diabetic population with ever more convenient and accurate ways to measure blood glucose levels and to deliver insulin to the patient. There are many forms of blood glucose measuring devices; one common type is represented by hand-held electronic meters which receive blood samples via enzyme-based "test strips", In using these systems, the patient lances a finger or alternate body site to obtain a blood sample, the strip is inserted into a test strip opening in the meter housing, the sample is applied to the test strip and the electronics in the meter convert a current generated by the enzymatic reaction in the test strip to a blood glucose value.

Some diabetic patients require insulin for the treatment of their diabetes, in order to maintain their glucose levels within the desired range. These "insulin-dependent" diabetic patients have traditionally administered insulin doses to themselves subcutaneously via either a hypodermic syringe or with a specialized injector known as an insulin pen. Although these subcutaneous injection methods can deliver insulin at an appropriate time and at an appropriate total dosage, the single bolus aspect of the delivery is unlike a physiological profile of insulin production in the body, which involves a lower rate of insulin entry into the bloodstream, over a more extended time course.

In order to address this issue, conventional techniques have evolved to include insulin pumps. With the insulin pump, a diabetic receives a continuous dosage of insulin from a pump apparatus via an "injection device" mounted on his or her body, Insulin is supplied (e.g., pumped) from the insulin pump through a tube to the injection device. Injection devices generally include a delivery cannula mounted in a subcutaneous manner through the skin of the patient at an infusion site. The injection device typically includes a channel that transmits insulin from an inlet port to the delivery cannula which results in delivery to the subcutaneous tissue layer of the diabetic in which the delivery cannula is located.

Insulin pumps offer significant therapeutic value as they deliver insulin if desired in a more normal physiological manner, with measured doses of insulin being slowly infused over an extended period of time. Further, the rate at which insulin is delivered can be programmed so as to follow standard or individually-modified protocols, thus giving the user even better glucose control over the course of a day. Conventional insulin pumps have evolved to become small in size, which offers easier portability and unobtrusiveness, and with electronic advances, they have evolved to become more fully-featured, and thereby capable of enhanced performance.

As mentioned above, standard-of-care insulin therapies for regulating blood glucose in diabetes typically involve either multiple daily subcutaneous injections or subcutaneous infusion with an insulin pump. Occasionally, the amount of dosed insulin can prove excessive in the sense that it can lead to hypoglycemia or a situation of impending hypoglycemia. To combat and/or reverse such adverse situations, individuals typically consume additional carbohydrates (e.g. sweet juice or glucose tablets) and in some situations can also administer a so-called "rescue dose" of a counter regulatory agent, such as glucagon. In such an application, glucagon is typically reconstituted into solution from an emergency kit and manually administered intramuscularly.

Hence, one traditional approach for managing diabetes is to control blood glucose levels via a control system that automates the transcutaneous delivery of both insulin and glucagon, as needed. Such a control system can, for example, orchestrate the automatic administration of both insulin and glucagon. With such a multi-hormone system, there is a need to fill one infusion reservoir (or infusion cartridge) with one medicament, and another infusion reservoir (or infusion cartridge) with another medicament. During the filling process, each medicament needs to be transferred from a storage vial to the reservoir or cartridge and then ultimately delivered to the patient. Since multiple different hormones having very different physiological effects are being delivered to the patient, it is important to make sure that the correct medicament is being delivered to the patient.

A drawback of the present multi hormonal regimens which employ multiple medicaments is that the patient or other person may accidentally load, transfer and/or administer the incorrect medicament. The accidental administration of the incorrect medicament to the patient can have serious and potentially fatal consequences.

SUMMARY OF THE INVENTION

It is thus an object of the present invention to provide a system and method to ensure the proper channeling of medicaments during the loading, transferal or administration process. The proper channeling of medicaments is especially important in the case of insulin and glucagon, since these medicaments produce opposite effects (e.g., lowering versus raising blood sugar levels). If the medicaments are accidentally loaded in the incorrect locations or reservoirs, the control system that automates delivery of the medicaments via the insulin pump can thus deliver the wrong medicament to the patient. Because the wrong medicament would have the opposite of the intended effect, this could not only fail to alleviate the patient's condition, but could make the patient's condition worse. Moreover, this improper channeling could cause a negative feedback loop, wherein the control system attempts to adjust the patient's blood sugar level in one direction, but the delivery of the incorrect medicament causes the blood sugar level to be altered in the opposite direction. Sensing this, the control system can trigger further doses of the wrong medicament in an attempt to control the patient's condition, causing the patient's condition to further deteriorate.

It is thus an object of the present invention to provide a system and method of preventing the administration of the incorrect medicament to the patient.

Exemplary embodiments of the present invention provide a multi-medicament infusion system that helps prevent the mischanneling of medicaments. The system can include an infusion pump, medicament reservoirs, one or more manifold, a multi-channel lumen assembly, and an infusion set. The medicament reservoirs may be sized and shaped differently such that the medicament reservoirs can only be inserted into the infusion pump in a unique or selected configuration. The multi-channel lumen may include feature elements such as connectors or adapters, that mate to corresponding connectors or adapters on the infusion pump and if desired the infusion set only in a unique configuration. Because the various parts of the multi-infusion system may only be connected in the unique configuration, the expected medicaments may be administered appropriately and channeled to the correct infusion sites.

According to one practice of the invention, a system for delivering multiple fluids to a patient is provided and includes at least first and second reservoirs, where each of the reservoirs houses a fluid and has a feature element associated therewith. The feature element of the first reservoir is different than the feature element of the second reservoir. The system also includes at least first and second inlets or ports (functioning at least as inlet ports), where each of the inlet ports has a feature element associated therewith, and wherein the feature element of the first inlet port is different than the feature element of the second inlet port. Further, the feature element of the first reservoir is complementary to the feature element of the first inlet port or a first intermediary coupling piece between the first reservoir and the first inlet port and the feature element of the second reservoir is complementary to the feature element of the second inlet port, such that when assembled the first reservoir is capable of only being fluidly coupled to the first inlet port and the second reservoir is capable of only being fluidly coupled to the second inlet port, thereby preventing mischanneling of the fluid.

According to the system of the present invention, an infusion pump is provided and the first and second inlet ports are formed therein. Alternatively, the first and second inlet ports are manifolds disposed on the outside of the infusion pump or formed in the infusion pump. Additionally, the infusion pump can include a first outlet port fluidly coupled to the first inlet port, and a second outlet port fluidly coupled to the first inlet port.

The first reservoir can house for example a regulating agent, such as insulin, and the second reservoir can house a counter-regulatory agent, such as glucagon.

According to the present invention, the feature element of the first inlet port can comprise a first surface feature and the feature element of the second inlet port can comprise a second surface feature, where the first surface feature is different than the second surface feature. According to one embodiment, the first and second inlet ports each have formed therein a piercing element for piercing the first and second reservoirs, respectively. If desired, the first and second inlet ports can be removably and replaceably coupled together.

The system can also include a first cap element having a feature element associated therewith and is configured to engage at least the feature element of the first inlet port, and a second cap element having a feature element associated therewith and is configured to engage at least the feature element of the second inlet port. The feature element of the first cap element is complementary in shape to the feature element of the first inlet port and the feature element of the second cap element is complementary in shape to the feature element of the second inlet port, such that when assembled the first cap element is capable of only being fluidly coupled to the first inlet port and the second cap element is capable of only being fluidly coupled to the second inlet port. Further, the first and second cap elements simultaneously respectively engage with the first and second reservoirs and the first and second delivery ports so as to secure the reservoirs in place.

The system in addition to the infusion pump can include a multi-channel lumen assembly having a first tube having an inlet port fluidly coupled to the first outlet port of the infusion pump and an outlet port, and a second tube having an inlet port fluidly coupled to the second outlet port of the infusion pump and an outlet port, and an infusion set having a first inlet port fluidly coupled to the outlet port of the first tube and a second inlet port fluidly coupled to the outlet port of the second tube.

According to another practice, the first outlet port of the infusion pump has a feature element associated therewith and the second outlet port of the infusion pump has a feature element associated therewith. The inlet port of the first tube of the multichannel lumen assembly has a feature element associated therewith and the second tube of the multi-channel lumen assembly has a feature element associated therewith. The feature element of the first outlet port of the infusion pump is complementary in shape to the feature element of the inlet port of the first tube and the feature element of the second outlet port of the infusion pump is complementary in shape to the feature element of the inlet port of the second tube, such that when assembled the first outlet port is capable of only being fluidly coupled to the inlet port of the first tube and the second outlet port is capable of only being fluidly coupled to the inlet port of the second tube.

According to still another practice, the outlet port of the first tube of the multichannel lumen assembly has a feature element associated therewith and the outlet port of the second tube of the multi-channel lumen assembly has a feature element associated therewith. Further, the first inlet port of the infusion set has a feature element associated therewith and the second inlet port of the infusion set has a feature element associated therewith. The feature element of the outlet port of the first tube of the multi-channel lumen assembly is complementary in shape to the feature element of the first inlet port and the feature element of the outlet port of the second tube of the multi-channel lumen assembly is complementary in shape to the feature element of the second inlet port, such that when assembled the outlet port of the first tube is capable of only being fluidly coupled to the first inlet port and the outlet port of the second tube is capable of only being fluidly coupled to the second inlet port.

According to yet another embodiment, the inlet port of the first tube has one or more feature elements to serve as a first intermediary coupling piece by attaching to the feature element of the first reservoir and the feature element of the first inlet port, and the inlet port of the second tube has one or more feature elements to serve as a second intermediary coupling piece by attaching to the feature element of the second reservoir and the feature element of the second inlet port. When assembled, the first reservoir is capable of only being fluidly coupled to the inlet port of the first tube and the second reservoir is capable of only being fluidly coupled to the inlet port of the second tube, thereby preventing mis-channeling of the fluid.

BRIEF DESCRIPTION OF THE DRAWINGS

These and other features and advantages of the present invention will be more fully understood by reference to the following detailed description in conjunction with the attached drawings in which like reference numerals refer to like elements throughout the different views. The drawings illustrate principals of the invention and, although not to scale, show relative dimensions.

FIGS. 8A-8C are unassembled perspective views of the different types of feature elements of FIGS. 7A-7C that can be used in connection with the outlet ports of the infusion pump according to the teachings of the present invention.

FIG. 9A is a perspective view of the multi-channel lumen assembly of the infusion system of FIG. 1 according to the teachings of the present invention.

FIG. 9B is cross-sectional view of the attachment feature of the multi-channel lumen assembly according to the teachings of the present invention.

DETAILED DESCRIPTION

The present invention described herein relates to an infusion system 10 for subcutaneously delivering a plurality of medicaments or infusates, and preferably different types of medicaments or infusates, to a patient. Specific examples are set forth below with respect to a dual-medicament delivery and infusion system for delivering multiple medicaments, such as for example insulin and glucagon, to the patient. However, one of ordinary skill in the art will readily recognize that the infusion system 10 of the present invention may be used with other types of medicaments or infusates, and may be used, configured or designed to deliver more than or less than two medicaments.

In a conventional infusion system suitable for delivering a single type of medicament to the patient (e.g., a conventional insulin pump), it is generally unnecessary to ensure that the expected or correct medicament has been properly installed in the expected configuration or orientation within the pump. Because the conventional system utilizes only a single medicament that is typically carefully sourced, there is limited cause for concern that the wrong medicament is used or that the medicament is installed in an incorrect manner.

When increasing the number of medicaments to be delivered to or infused within the patient, however, the correct installation of the medicaments becomes a potential source of problems. Especially in the case of a system for delivering counter-acting medicaments (such as glucagon and insulin), the results of a mis-installed or mischanneled medicament can be harmful or potentially fatal. Furthermore, if the medicaments are to be installed by the end-user (e.g., in the patient's home), it may be quite easy to incorrectly install the medicaments and/or the various parts of the system that channel the medicaments to their infusion sites if the user has no formal medical training.

The present application addresses these and other problems. Exemplary embodiments provide a safe and reliable multi-medicament infusion system that prevents the incorrect installation and mischanneling of medicaments. The systems and methods of the present invention as described herein can be used in an in-patient setting or an outpatient setting, and can be used in the context of an autonomous or semi-autonomous closed-loop glucose control system (e.g. sensor-augmented infusion system).

Figure 1:
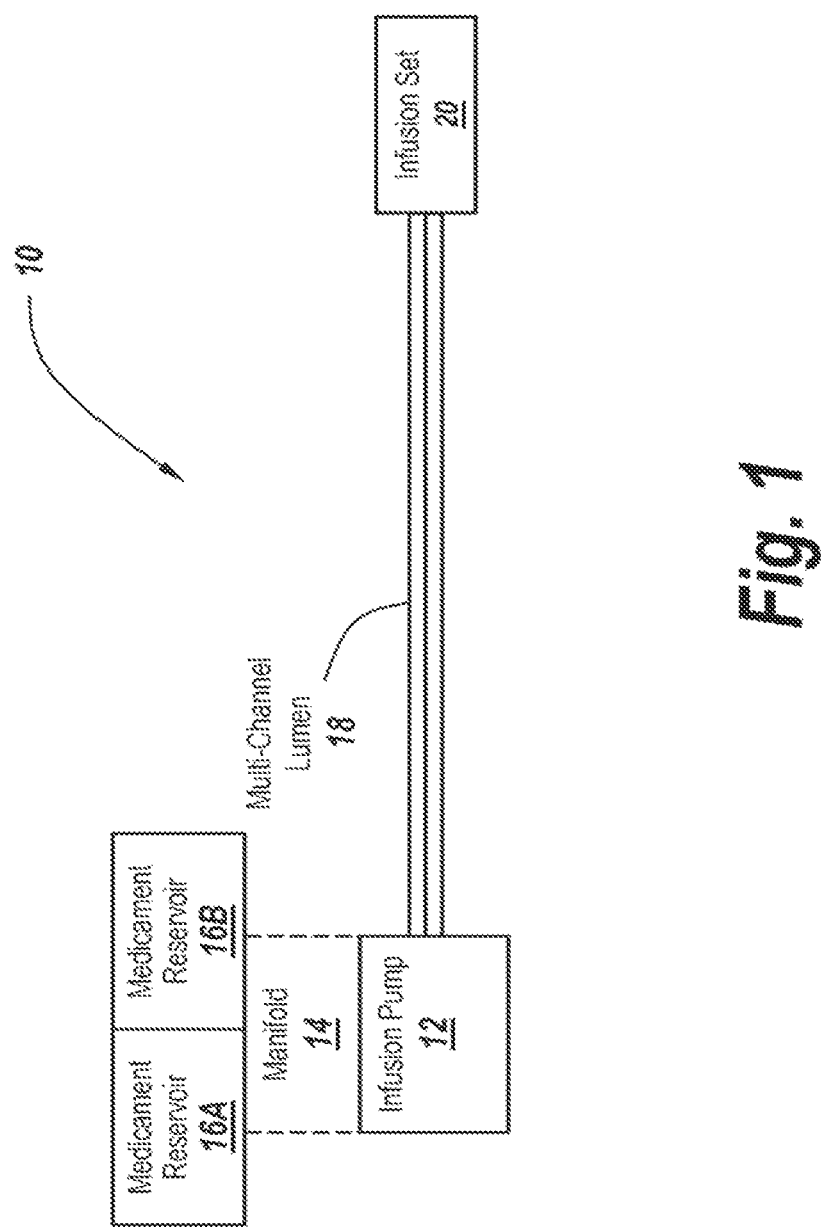
FIG. 1 is a schematic block diagram depicting an overview of a multi-medicament infusion system according to the teachings of the present invention.
Figure 2:
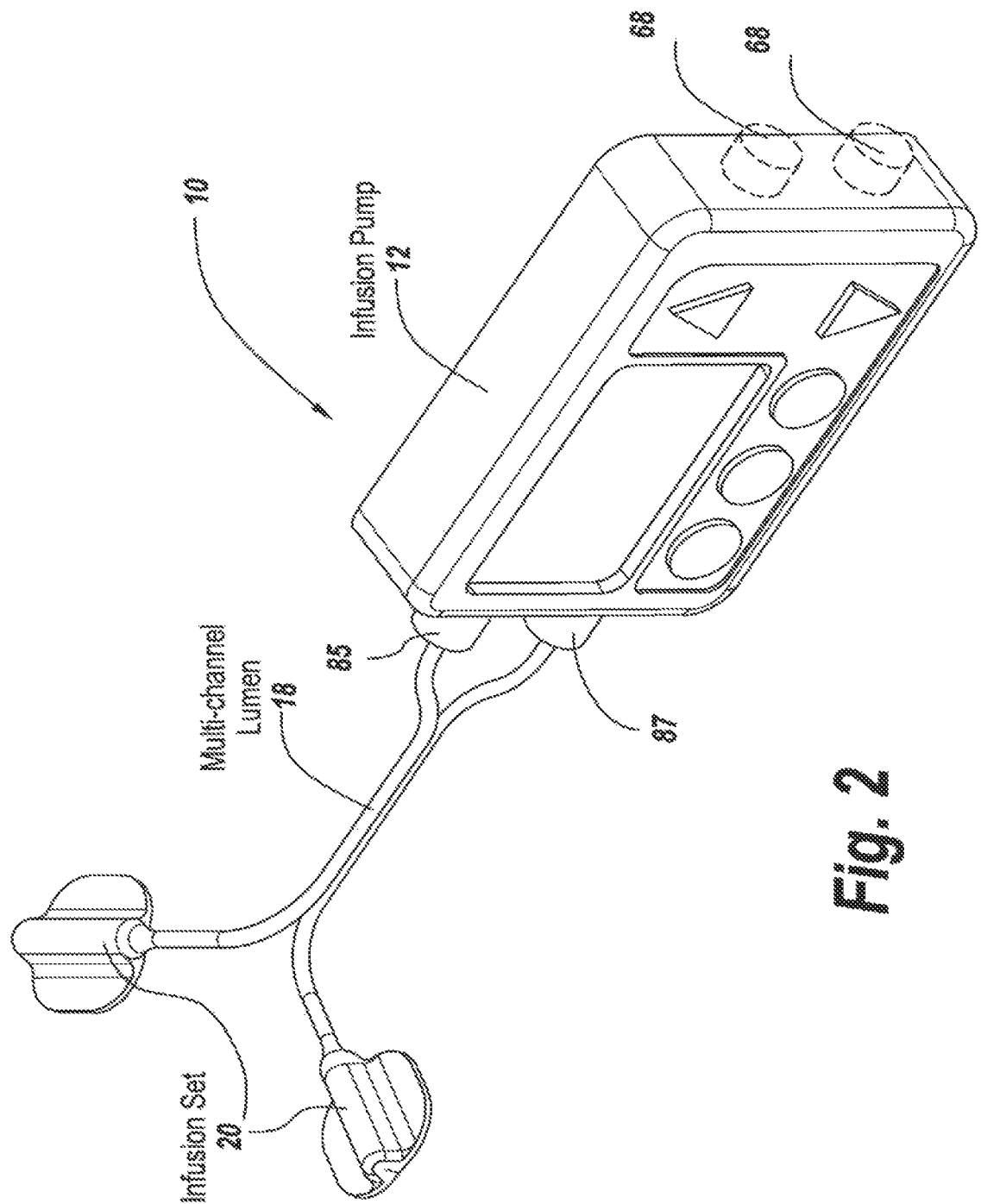
FIG. 2 is a perspective view of an exemplary multi-medicament infusion system employing an infusion pump, a multi-channel lumen assembly, and an infusion set according to the teachings of the present invention, where the manifold and reservoirs are either housed within the infusion pump or are not yet connected.

FIGS. 1 and 2 are schematic diagrams depicting an overview of a multi-medicament infusion system 10 according to an exemplary embodiment of the present invention. The illustrated infusion system 10 includes for example a delivery device such as an infusion pump 12 for delivering one or more medicaments to a patient. The infusion pump 12 is coupled to a manifold 14 that is shaped and configured for accepting a plurality of medicament reservoirs 16A and 16B. The manifold 14 allows the medicament reservoirs 16A, 16B to be fluidly coupled to the infusion pump 12. Alternatively or in addition, the medicament reservoirs 16A, 16B can be inserted directly into manifolds that can be formed directly and integrally within the infusion pump without the use or need for an external manifold 14. The infusion pump 12 serves to deliver (i.e., pump) the medicaments from the medicament reservoirs 16A, 16B to a multi-channel lumen or tube assembly 18, which carries the medicaments to an infusion set 20 that subcutaneously delivers the medicaments to the patient.

The medicament reservoirs 16A, 16B may be inserted into the infusion pump 12 via an inlet. The inlet can function as an inlet port, an outlet port or both. For example, FIG. 2 shows (in phantom) two connectors or caps 68 covering inlet ports into which the medicament reservoirs 16A, 16B may be inserted and two caps or connectors 85, 87 that are coupled to the outlet ports. As used herein, the term "inlet" or "port" is meant to include any suitable aperture for receiving a medicament reservoir 16A, 16B and/or delivering a medicament from the medicament reservoir 16A, 16B to another device. In some embodiments, an inlet may receive the medicament on a first device and a separate aperture or outlet may deliver the medicament from a first device to a second device. In other embodiments, the inlet aperture and the outlet aperture may be integral, or no outlet aperture may be provided at all. As such, the inlet hence functions as a combination inlet/outlet port or aperture. The presence of an inlet with a corresponding inlet port or aperture on a device does not necessarily require the presence of a distinct outlet or outlet port or aperture on that device.

Alternatively or in addition, a manifold 14 may be provided in place of the inlet ports/caps 68. Medicament from the medicament reservoirs may be delivered to the multi-channel lumen 18 through an outlet port of the infusion pump 12.

In some embodiments, the inlet port of the infusion pump 12 (through which the medicament is received by the infusion pump 12) and the outlet port of the infusion pump 12 (through which the medicament is pumped to the multi-channel lumen 18) may be the same. For example, the multi-channel lumen 18 may be provided with an integrated first medicament inlet/outlet interface 85 and an integrated second medicament inlet/outlet interface 87. Specifically, the inlets covered by the connectors 68, 68 can be eliminated and the inlets covered by the connectors 85, 87 thus function as combined inlet/outlet ports. In such an embodiment, the medicament reservoirs 16A, 16B may be inserted into respective ports or openings in the infusion pump 12. The integrated first and second medicament inlet/outlet connectors or interfaces 85, 87 may interface with the inlet/outlet ports or openings of the infusion pump 12 to receive medicaments pumped by the infusion pump 12. The infusion system employing connectors and ports of this type are also illustrated in FIGS. 4, 6D, 7A-7C, 14, 17A-17B, and 18.

The multi-channel lumen assembly 18 can include two or more channels, where each channel is adapted to deliver a particular type of medicament to an appropriate inlet port on the infusion set 20. The multiple channels (e.g., fluid pathways) formed by the multi-channel lumen assembly 18 may be coupled and uncoupled together in order to assist the patient in assembling the infusion system, replacing one or more tubes of the assembly, or preventing the tubes of the lumen assembly from becoming tangled or caught on objects during daily use and during the performance of normal daily activities.

The multiple channels may bridge the span between the infusion pump 12 and the infusion set 20 by independent channels where each channel can be a single or multiple-lumen channel, by channels joined by webbing or by some other manner where each channel can be a single or multiple-lumen channel, or by a single multiple-lumen channel where the enclosed lumens are arranged in an array or as concentric lumens.

The infusion set 20 can connect the multi-channel lumen assembly 18 to a delivery system, such as a cannula, for delivering the medicaments to the user. The infusion set 20 can include one or more infusion ports that adheres to the skin of the patient and which contains one or more piercing elements, such as needles or cannulas, and which are inserted on, into, or under the skin and which can reside there for one to several days before being replaced by a new infusion set.

The illustrated infusion pump 12 can be any suitable infusion pump sized and configured to deliver a plurality of medicaments as set forth herein. The infusion pump 12 may be programmed with suitable logic for controlling the delivery of the medicaments based on measurements associated with a condition of the user. For example, in the case of an infusion pump 12 for delivering medicaments, such as insulin and glucagon, the infusion pump may control the delivery of the medicaments based on real-time measurements of the user's blood glucose level measured from, for example, a glucose sensor (not shown) that is operatively coupled to the patient and if needed to the pump. The infusion pump 10 may be manually operated, semi-autonomous with some manual control by the user, or part of a fully autonomous multi-hormone glucose-control system, an example of which is a closed-loop glucose control system that uses a sensor-augmented infusion pump mechanism to automatically administer both insulin and glucagon or other medicaments. As such, the infusion pump 12 can be coupled if desired to a controller (not shown) that assists with the control and operation of the delivery device. An example of a system and associated control logic suitable for use with the infusion system of the present invention is described in U.S. Pat. No. 7,806,854, assigned to the assignee hereof, the contents of which are herein incorporated by reference.

The infusion pump 12 can be any pump suitable for delivering via a catheter and tubing assembly a plurality of medicaments to the patient. The infusion pump 12 for example can be an ambulatory infusion pump that can deliver the medicament (such as insulin) through the tubing assembly 18 and associated infusion set 20, thereby permitting the subcutaneous infusion of the desired medicine. Features of the illustrated infusion pump 12 may include, for example and without limitation, basal and/or bolus delivery programs, bolus calculation estimators, limit alarms, reminders, visual, vibratory and auditory alarm indications, pump operation logging and analysis, and optionally, a food database to assist in calculating meal carbohydrate amounts. Although not illustrated herein, the infusion pump 12 can communicate via a cable or wirelessly to a computing device. Those of ordinary skill will readily recognize that the computing device can include a controller and other associated hardware and software capable of communicating with or controlling the infusion pump, and providing if desired information or other data to the infusion pump, such as configuration settings and personal data. The computing device may include software for maintaining or storing logs, displaying pump data in text or graphical format and may provide analysis to the user and/or healthcare professionals. The infusion pump can also include a display-screen and an on-board power source for providing power to the pump.

In the illustrated infusion system 10, there are several locations at which a medicament can be mis-installed or mischanneled. For example, the incorrect medicament reservoir can be placed or mounted in the incorrect manifold 14 or coupled to the incorrect inlet port of the infusion pump 12. The outlet ports of the infusion pump 12 can be connected incorrectly to the respective channels of the multi-channel lumen assembly 18, and thus even if the medicament reservoirs were properly installed, they can be improperly channeled to the infusion site. Finally, the end portions or outlets of the multi-channel lumen assembly 18 can be connected to the incorrect inlets of the infusion set 20.

The exemplary embodiments of the present invention address these concerns by providing feature elements and/or mating connectors or adapters on certain components of the infusion system 10. The unique mating connectors and feature elements ensure that each portion of the system can only be connected to the system in a unique way or configuration, thus preventing the mischanneling of medicaments. The exemplary embodiments of the present invention may have the following advantages: (1) the infusion system allows the user to easily connect and disconnect the channels independently from both medicament sources as well as from the infusion ports or sites; (2) the infusion system mitigates the possibility of mischanneling by accidentally connecting the wrong tubing to the wrong medicament source or infusion site (e.g., by having a connector that is disposed between one tube and one pump reservoir of one medicament system differ from the connector of the other tube and reservoir); and (3) the infusion system allows for a single or multistep insertion of the dual-cannula infusion site or port.

One of ordinary skill in the art will understand that the infusion system depicted in FIGS. 1-2 is intended to be exemplary only. A suitable medicament delivery system may include more or fewer parts than depicted. For example, it is contemplated that the multi-channel lumen assembly 18 may be omitted, so that the infusion pump 12 is integral with the infusion set 20. Control logic for controlling the infusion pump 12 may be built into the infusion pump 12, or may be separate from the infusion pump (e.g., being provided in a separate computing device, such as a mobile phone or handheld pump controller, which communicates wirelessly with the infusion pump 12).

In such an embodiment, the reservoirs 16A, 16B may be bladders in the infusion pump 12 that are manually filled, such as by a syringe. The syringe may include surface features designed to mate with a filling port on the infusion pump 12, such that only one type of syringe is able to fill a respective bladder. In another embodiment, the infusion pump 12 may be of a clamshell design, folding open in order to allow one or more cartridges to be inserted as the reservoirs 16A, 16B, in which case the cartridges may be provided with surface features such that the cartridges may only be inserted into an appropriate slot or port of the infusion pump. In yet another embodiment, the cartridges may be loaded into an intermediate loading device which transfers the fluids from the cartridges to the infusion pump 12, in which case the intermediate loading device may be provided with surface features matching inlet ports of the infusion pump 12.

With reference to FIGS. 3A-3E, the infusion system 10 of the present invention may further include a plurality of manifolds 14 for housing and fluidly coupling a reservoir thereto. Like reference numerals denoting like or similar structure will be used throughout the various Figures and views. Each manifold can be an external manifold that is provided external to the infusion pump or the manifold can be an internal manifold that is housed within the pump, such as illustrated for example in FIGS. 4, 7A-7C, 14, and 18. According to exemplary embodiments, the manifold 14 forms in essence a docking port for the medicament reservoir 16 that allows for the reliable transfer of one or more medicaments or infusates from the reservoir to the infusion pump 12 in such a manner as to prevent the mischanneling of the medicaments or infusates during the transferal or administration process. For the sake of simplicity, the manifold is illustrated external to the infusion pump 12. The manifold preferably forms a plurality of chambers, which are typically separate and distinct from each other, and which are configured to house a specific medicament reservoir. Although the chambers are preferably fluidly isolated from each other, those of ordinary skill will readily recognize that the manifold can be configured to house multiple reservoirs. According to yet another practice, the manifold can be constructed to hold multiple reservoirs in a common chamber.

The manifold 14 can be shaped, sized or configured for coupling, either directly or indirectly through any suitable intermediate mechanical device, to the reservoirs 16A and 16B. The reservoirs can be any housing or structure suitable for containing or holding a selected fluid. The fluid holding structure can be flexible or relatively rigid depending upon the application or use of the reservoir. The fluid can be any suitable fluid such as for example a medicament or infusate. Examples of suitable fluid holding structures include vials, cartridges, bladders, ampoules, or other suitable containers for holding the fluid. Moreover, the reservoir can be configured to include a septum as is known in the art. For purposes of simplicity, we reference below the delivery of a medicament. The medicament can include any suitable compound or drug for treating, regulating, controlling or addressing one or more conditions of the patient. In the present embodiment, the condition is diabetes mellitus, although those of ordinary skill will readily recognize that other conditions can be addressed as well. The medicament can include for example a regulating agent, such as insulin, for regulating the blood glucose levels in the patient and/or a counter-regulatory agent, such as glucose or glucagon, for more effective blood glucose regulation in certain circumstances. One of ordinary skill in the art will readily recognize that other type of agents can be used as well.

The present invention provides for a selected feature element or connector/adapter to be disposed on either or both the manifold or reservoir for ensuring that the proper medicament reservoir is coupled to the proper or correct manifold. This arrangement of components helps prevent the accidental coupling of a reservoir containing a specific medicament to an incorrect manifold. For example, according to one practice, the manifold includes two separate manifolds each configured to mate with a specific reservoir. Hence, a first manifold can be adapted to accommodate a first reservoir containing a first medicament, such as insulin, and a second manifold can be adapted to accommodate a second reservoir containing a second medicament, such as glucagon. In this example, it is important to ensure that the glucagon reservoir is not accidentally coupled to the insulin manifold and vice versa.

One or more components of the infusion system, including for example the manifold, reservoir, pump, or any combination of components, can include a selected feature element that ensures the proper coupling together of the components to help prevent the mischanneling or misloading of medicaments. The term "feature" or "feature element" as used herein can include any suitable structure, coupler, connector, adapter or feature having any suitable size, shape, dimension, or surface element or surface feature that allows, permits, enables or facilitates the coupling together of one or more system components, such as for example a selected reservoir to a selected manifold or portion of a manifold, whether external to the infusion pump or internal to the infusion pump, in selected ways so as help prevent the mischanneling of medicaments. The feature element can include for example the size, area or volume of a component, such as the volume or size of a chamber defined by the manifold. The feature element is also intended to include any suitable surface feature, which can include for example, any element formed on, within or which protrudes from a surface of one or more components of the infusion system, such as for example the manifold, reservoir, pump, tubes of infusion set, that also allows, enables or facilitates the coupling together of one or more system components. Examples of suitable surface features can be detents, ribs, slots, keys, grooves, holes, corrugations, indentations, or any other suitable mechanical and/or electrical coupling or attaching element. When a surface feature is formed for example on the reservoir or manifold, the present invention contemplates forming a complementary shaped surface feature on the other mating system component or element, thus allowing the reservoir and the manifold to be coupled together. If the corresponding surface feature is absent from the corresponding element, then the reservoir and manifold cannot be coupled together. The feature element is also intended to include any suitable connector, coupler, fastener or adapter that is also adapted and configured to mechanically and/or fluidly couple together one or more components of the infusion system. In some embodiments, two elements (such as the medicament reservoirs 16A, 16B and the infusion pump 12 or lumen 18) may be indirectly coupled to each other through an intermediary coupling piece. For example, the intermediary coupling pieces may be connectors or caps (such as the caps 68, 84, 86) or the inlet ports of lumen 18 (such as the inlet ports 85, 87) that capture the medicament reservoirs 16A, 16B and couple to the infusion pump 12, as described in exemplary embodiments below.

Preferably, the feature elements when employed help form specific dedicated fluid pathways that helps prevent the mischanneling of medicaments and hence helps prevent the accidental administration of an incorrect medicament to the patient.

As illustrated in FIGS. 1-3E, the manifolds 14A, 14B can include differently sized or configured chambers or slots which are adapted to only couple to matching medicament reservoirs 16A, 16B filled with the proper medicaments. The manifolds allow the specific or unique engagement with or insertion of one or more specific medicament reservoirs of different cross-sectional sizes and/or shapes or profiles. The manifold allows the medicament reservoirs to be secured in place so that they can be captured by and/or carried within the manifold housing. This capture may be a permanent capture or can employ a multi-use capture and release methodology, as is known in the art.

Figure 3A:
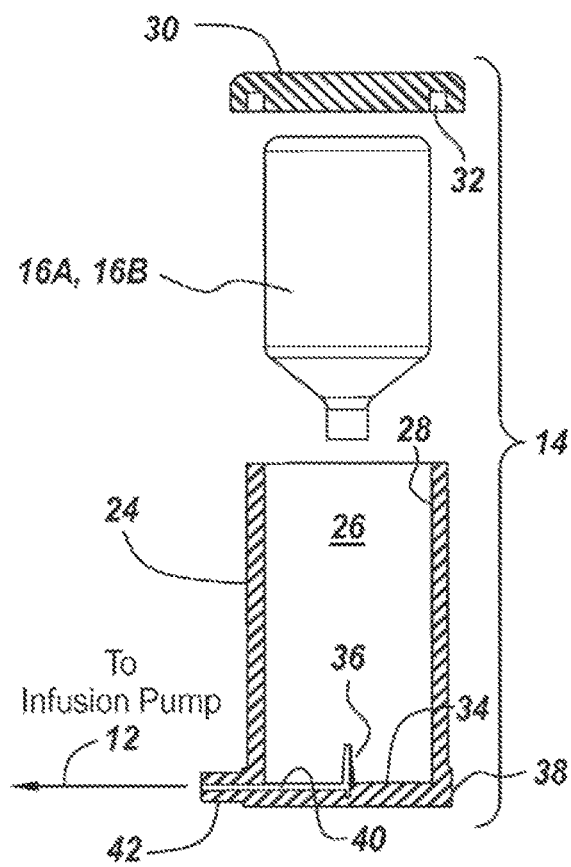
FIG. 3A is a cross-sectional view of the manifold and reservoir portion of the infusion system of FIG. 1 illustrating the capture of the reservoir within a chamber of the manifold according to the teachings of the present invention.

Further, the manifolds and reservoirs can have any selected shape, size or design. To that end, FIGS. 3A-3E illustrate one embodiment of a manifold and reservoir combination that is suitable for use with the infusion system 10 of the present invention. FIG. 3A is a cross-sectional view of a single port manifold 14 and associated reservoir 16A. One of ordinary skill in the art will readily recognize that another manifold and reservoir assembly can be provided so as to be able to administer multiple medicaments to the patient. For the sake of simplicity, only one manifold is illustrated and described herein. The illustrated manifold 14 can include for example a housing 24 having an inner wall 28 that defines an interior chamber 26. The chamber has a bottom surface that has a piercing element, such as a needle portion 36, extending outwardly therefrom. The piercing element can include any suitable structure configured for piercing the reservoir in order to draw or extract the medicament therefrom. The needle portion is adapted to pierce or penetrate a reservoir when mounted in the chamber 26 so as to fluidly couple the medicament housed within the reservoir with the infusion pump. The housing also includes a base portion 38 that has a fluid or medicament passage 40 formed therein. The fluid passage terminates in a coupler portion or connector end 42. The reservoir is hence fluidly coupled with the infusion pump via the needle 36 and fluid passage 40. The base elements can be a separate base structure that has a single chamber housing associated therewith, FIG. 3D. Hence, a separate, second base portion and associated housing can be provided to deliver a second medicament to the infusion pump. The base portions can be configured if desired to be coupled together in a removable and replaceable manner or the base portion be formed as a unitary structure that has associated therewith multiple housings, FIG. 3E.

The manifold 14 can also include a cap element 30 that helps seal the top portion of the chamber 26 when attached to the housing 24. The cap element 30 can be coupled or secured to the housing 24 by any suitable mechanism. In the illustrated example, the cap includes a groove 32 formed on an underside of the cap that is adapted to mate with the top edge of the housing.

Figure 3B:
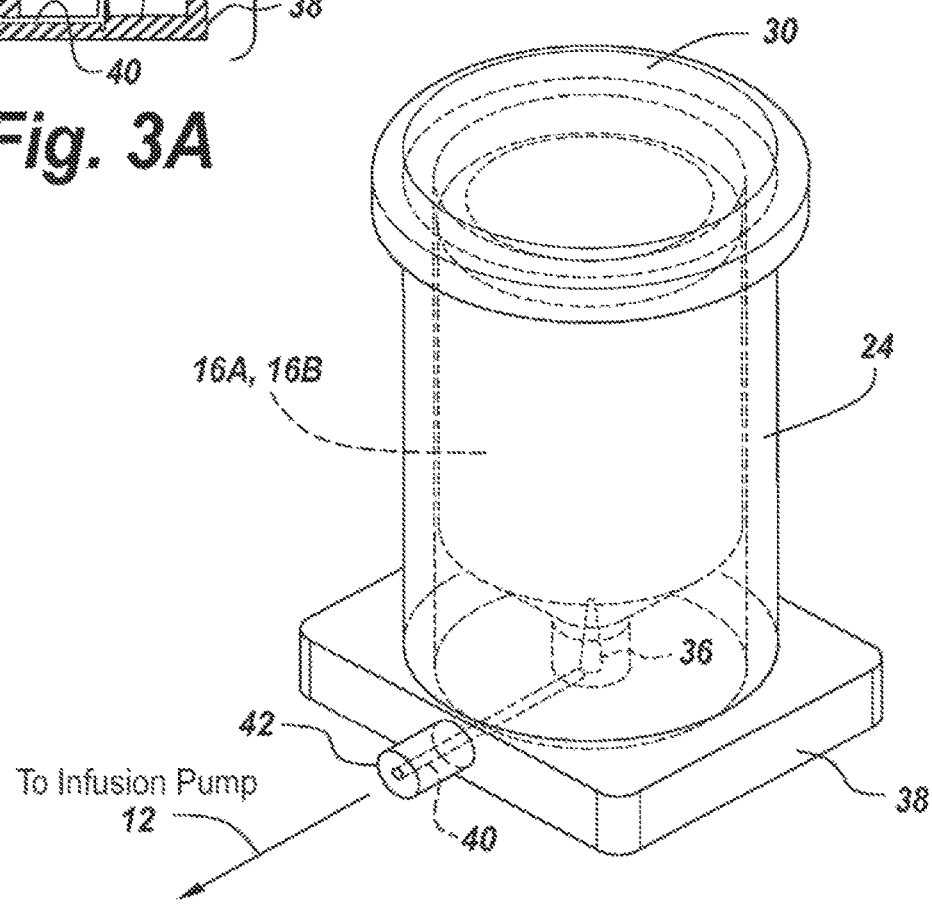
FIG. 3B is a perspective view of the manifold and reservoir portion of the infusion system of FIG. 1 illustrating the capture of the reservoir within a chamber of the manifold and the extraction of the medicament housed within the reservoir according to the teachings of the present invention.
Figure 3C:
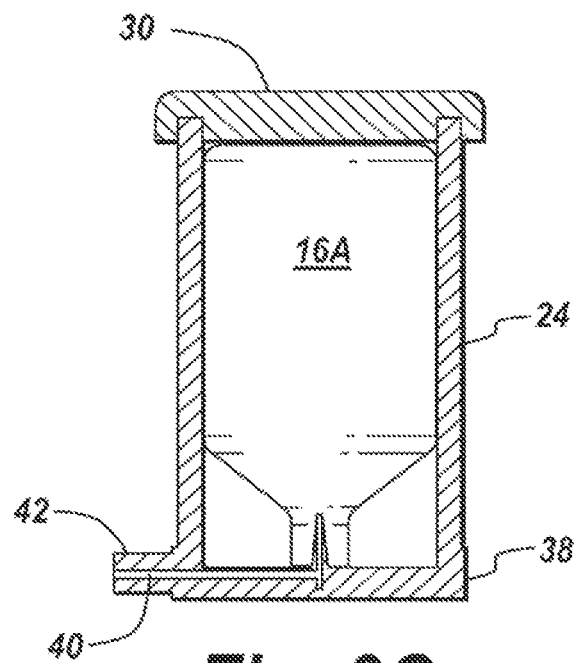
FIG. 3C is a cross-sectional view of the manifold and reservoir portion of the infusion system of FIG. 1 assembled together according to the teachings of the present invention.
Figure 3D:
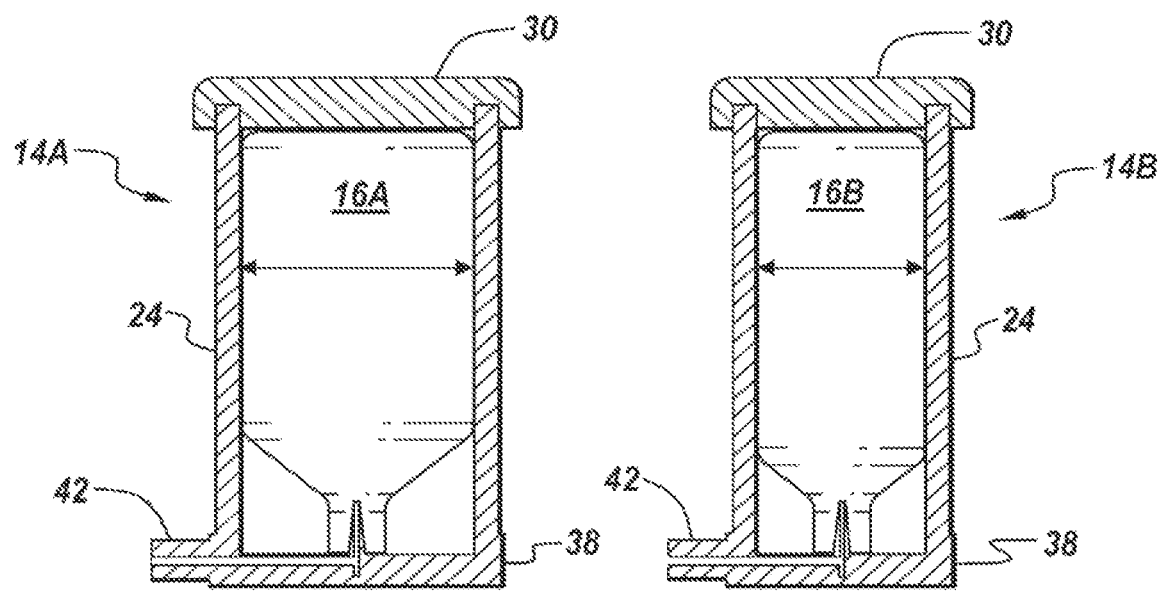
FIG. 3D is a cross-sectional view of the multiple manifolds and reservoirs of the infusion system of FIG. 1 assembled together where the manifolds have different sized manifold chambers to prevent the accidental loading of a reservoir in the incorrect manifold according to the teachings of the present invention.
Figure 3E:
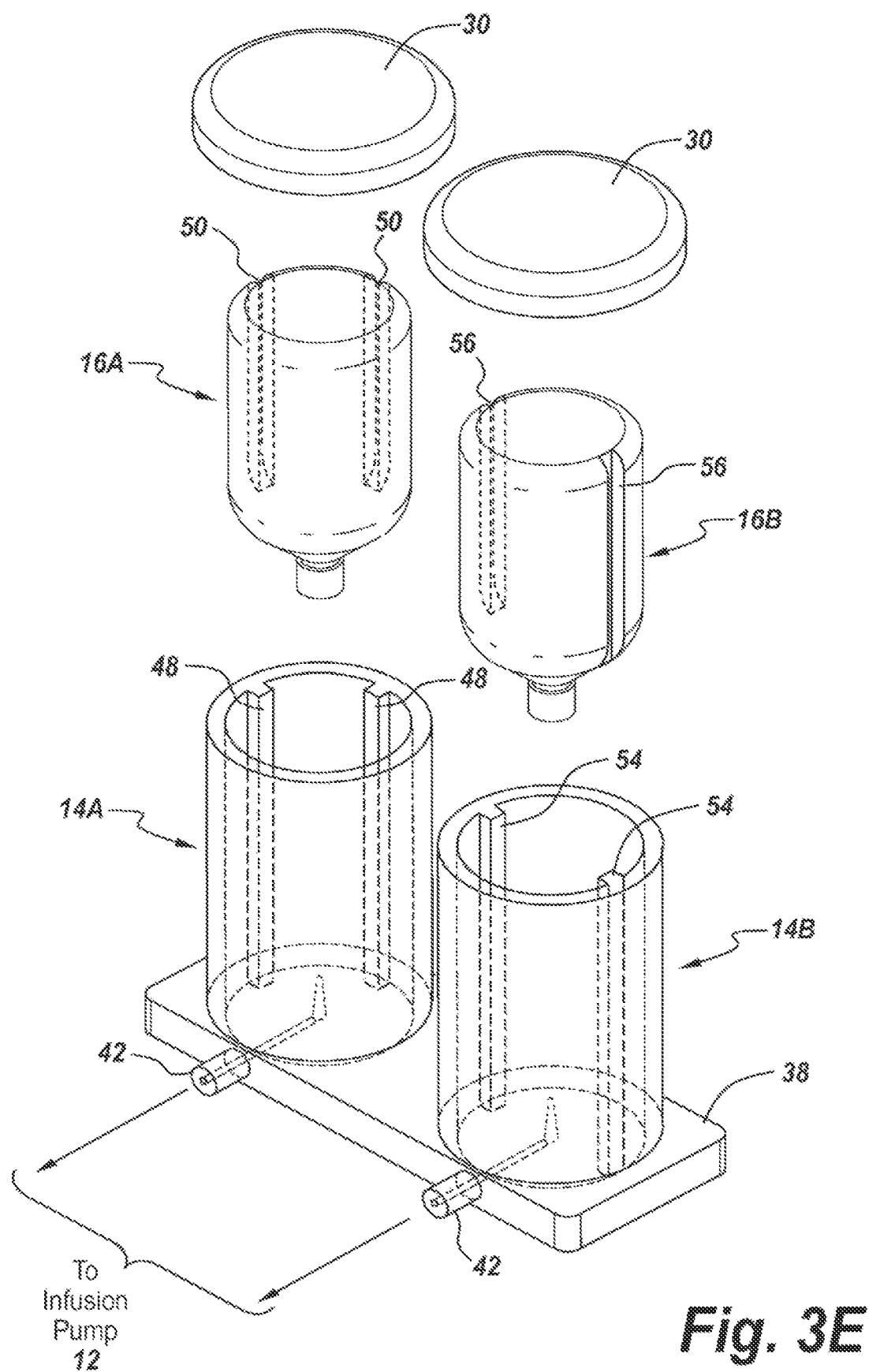
FIG. 3E is a cross-sectional exploded view of the multiple manifolds and reservoirs of the infusion system of FIG. 1 where the manifolds and reservoirs have different mating feature elements to help prevent the accidental loading of a reservoir in the incorrect manifold according to the teachings of the present invention.

As shown in FIGS. 3D and 3E, the manifolds and/or reservoirs can be configured such that only a selected reservoir is capable of being mounted or seated within a selected manifold. The feature elements employed to effectuate this can be varied, as described above. For example, as shown in FIG. 3D, the manifolds can be sized such that the chamber of a first manifold 14A is larger than the chamber of a second manifold 14B. In this scenario, the chamber of the first manifold 14A is larger (e.g., has a larger diameter and hence has a greater volume) than the chamber of the second manifold 14B. This arrangement is particularly advantageous when employing insulin and glucagon as medicaments, since the commercially available prefilled reservoirs containing insulin tend to be larger, and oftentimes significantly larger (e.g., three times as large), than the commercially available reservoirs containing glucagon. Hence, in the current example, the reservoir 16A can contain insulin and is adapted to be mounted within the larger manifold 14A. Likewise, the smaller reservoir 16B can contain glucagon and is adapted to be mounted within the smaller manifold 14B. The patient is thus able to easily and readily determine which reservoir 16A, 16B is adapted to seat within which manifold 14A, 14B simply based on the sizes of the reservoirs and associated chambers. This arrangement helps provide a safe and reliable multi-medicament infusion system that prevents the incorrect installation and mischanneling of medicaments.

Furthermore, as illustrated, the base portion of the manifolds 14A, 14B can be separate and distinct from each other. Although not shown, the base portions can also be configured to be easily assembled and disassembled. The base portions can be coupled together using known connection techniques, including the use of snap fit features and the like. When designed as such, the based portions allow the patient to configure and customize the infusion system in a manner that best suits the patient's needs by the ability to detach and reattach the base portions as needed or desired.

Alternatively, and according to another practice, the manifolds and the reservoirs can include one or more surface features that helps determine which reservoir is intended to be accommodated in a particular manifold. As illustrated in FIG. 3E, the first manifold 14A can include one or more surface features, such as ribs 48, that are formed on and extend outwardly from the inner wall 28 into the chamber. The ribs can be spaced apart and disposed at selected locations about the circumference of the inner wall. The reservoir 16A can also include one or more mating or complementary shaped surface features, such as for example grooves 50, that are formed within an outer surface of the reservoir and which are spaced at selected locations that correspond to the locations of the ribs 48. Hence, the reservoir 16A having the grooves 50 formed therein is adapted to seat within and mate with the corresponding ribs 48 of the manifold 14A.

Similarly, the second manifold 14B can include one or more surface features, such as ribs 54, that are formed on and extend outwardly from the inner wall 28 into the chamber. The ribs 54 can be spaced at selected locations about the circumference of the inner wall. The second reservoir 16B can also include one or more mating or complementary shaped surface features, such as grooves 56, that are formed within an outer surface of the reservoir and which are spaced at selected locations that correspond to the locations of the ribs 48. Hence, the reservoir 16B having the grooves 56 formed therein is adapted to seat within and mate with the corresponding ribs 54 of the manifold 14B. In the current example, the locations of the ribs 54 and grooves 56 differ from the locations of the ribs 48 and grooves 50. As such, the reservoir 16B is prevented from being mounted within the manifold 14A, and the reservoir 16A is prevented from being mounted within the manifold 14B. This configuration prevents the accidental loading of a medicament reservoir in the incorrect manifold, thus avoiding the accidental administration to the patient of the incorrect medicament.

Those of ordinary skill in the art will readily recognize that many different types and shapes of feature elements and surface features can be employed by the manifold and reservoir of the present invention. For example, although a pair of protruding surface features are employed by the manifolds and a pair of groove style surface features are employed by the reservoirs of the present invention, the surface features can also be reversed where the grooves are formed in the inner wall of the manifolds and the ribs are formed on the outer surface of the reservoirs. Alternatively, the manifold chambers can have different shapes relative to each other and the reservoirs can be configured to have a shape complementary to its associated chamber to allow seating within the manifold. Furthermore, the feature elements can also be formed on the cap portion of the manifold rather than on the housing portion.

The illustrated base portion 38 is a single unitary base such that the manifolds 14A and 14B are coupled thereto and extend outwardly therefrom. Those of ordinary skill in the art will readily recognize that the base portion can also be split into separate portions; one portion associated with each manifold. Moreover, the separate base portions can be configured such that the base portions can be assembled and disassembled as needed.

According to another practice, the feature element can be constructed to include the piercing element rather than have the piercing element formed as part of the manifold. As such, in this potential configuration, the reservoir can be mounted within a manifold, such as for example a manifold formed internally within the infusion pump. A reservoir and a feature element, such as a connector, can be mounted within the manifold. The connector can include a piercing element for piercing the reservoir.

In use, the reservoirs are inserted within the chambers of the manifolds 14. Specifically, the reservoir 16A is mounted within the manifold 14A and the reservoir 16B is mounted within the manifold 14B. After properly seating or docking the medicament reservoir in the manifold, the cap is snapped into position, thus securely capturing the medicament reservoir within the manifold housing 20. FIG. 3B illustrates the manifold 14 with the medicament reservoir 16A captured within the housing. The cap 30 may permanently snap in place after capturing the medicament reservoir 14, resulting in a permanent capture of the medicament reservoirs 14, or the cap can be readily and easily removable to allow replacement of the reservoir. The needle portions formed in the chambers pierce the tip or head portions of the reservoirs when loaded within the chambers. When the reservoirs are pierced by the needle, the medicaments contained therein flow from the reservoirs through the fluid passage 40 and then eventually to the infusion pump 12. The infusion pump can then administer the medicament to the patient through the lumen or tube assembly 18 to the infusion set 20 as needed or desired. The infusion pump can be programmed to administer the various medicaments continuously or at selected intervals as is known in the art.

Furthermore, the manifolds 14 allow for automatic air-pressure equalization as fluid is drawn from the reservoirs 16A, 16B. The manifold may also allow a transparent view of the amounts of medicament resident in the reservoirs that are inserted within the chambers of the manifolds. Furthermore, the manifold 12 may detach into separate single manifolds/ports, and may be re-attached, or the manifold can be integrated together, such as on a common base portion.

In order to further prevent the accidental mischanneling or mis-loading of medicaments during the transfer of the medicament from the reservoirs to the infusion pump, the outlet ports of the manifold assembly and/or the inlet ports of the infusion pump can be configured to have different feature elements. According to one practice, each manifold can have an outlet port (e.g., coupler portion 42) that has a feature element that is different than the feature element formed on the outlet port of the other manifold. That is, the shape, size or design of the outlet ports of the manifolds can differ. The outlet ports are adapted to mate with a corresponding inlet port of the infusion pump or a tube having an inlet end that is shaped in a complementary manner to the associated manifold outlet port so as to form a fluid pathway between the manifold and the tube or between the manifold and the infusion pump. This fluid pathway allows the drawing of the medicament from the reservoir for the purpose of filling a corresponding cartridge or reservoir in the infusion pump.

The infusion pump can also have formed at outlet ports selected feature elements, such as connectors or adapters, that are also differently designed or configured so as to mate with a specific tube of the lumen assembly 18. This design feature can be in addition to the unique connecting arrangements of the inlet ports. Nonetheless, the formation of fluid pathways that are specific or unique to particular medicaments serve to help prevent the accidental administration of the wrong medicament to the patient. Further, those of ordinary skill in the art will readily recognize that the feature elements of the infusion system of the present invention can be deployed in multiple parts of the multi-medicament infusion system, such as at the connection between the medicament reservoir 16 and the manifold 14, the connection between the manifold 14 and the infusion pump 12, the connection between the infusion pump 12 and the multi-channel lumen assembly 18, and the connection between the multi-channel lumen assembly 18 and the infusion set 20.

Figure 4:
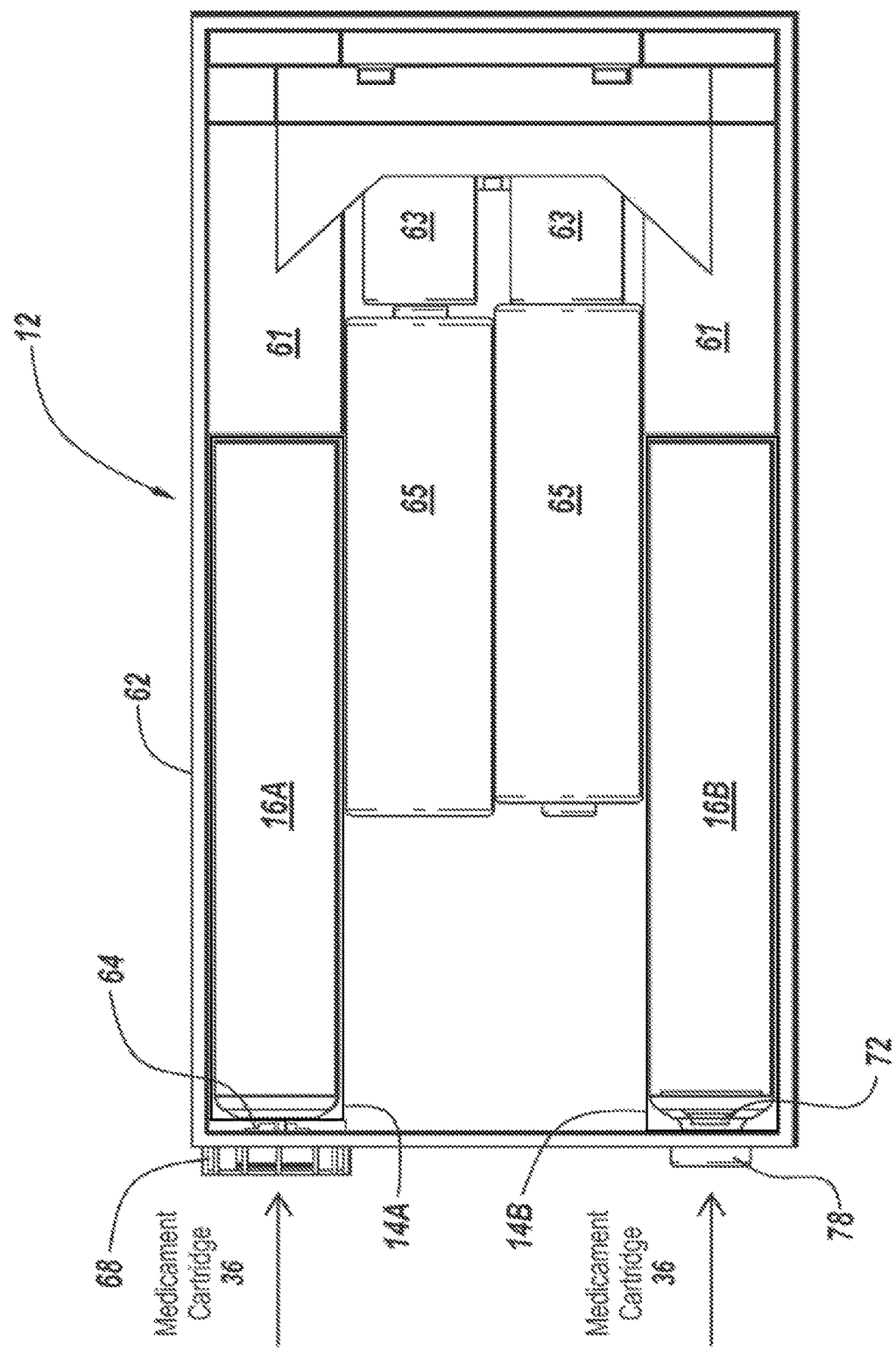
FIG. 4 is a cross-sectional view of one embodiment of an infusion pump illustrating the use of internal manifolds for housing different medicament reservoirs and the use of different feature elements for capturing the reservoirs within the manifolds and to help prevent the accidental mischanneling of medicaments according to the teachings of the present invention.
Figure 5A:
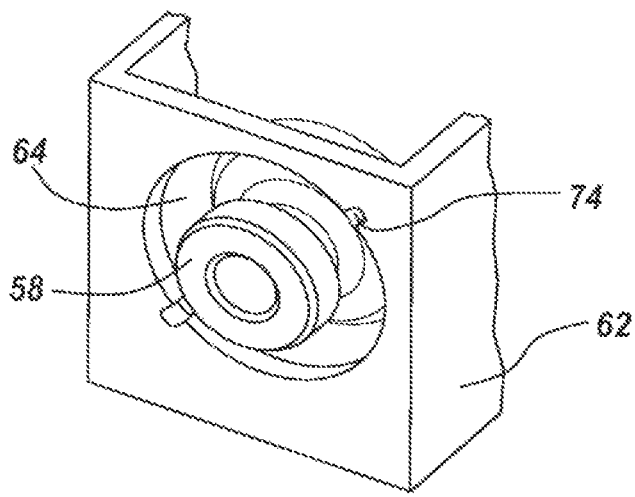
FIGS. 5A-5C illustrate the different feature elements used in connection with the infusion pump of FIG. 4 according to the teachings of the present invention.
Figure 5B:
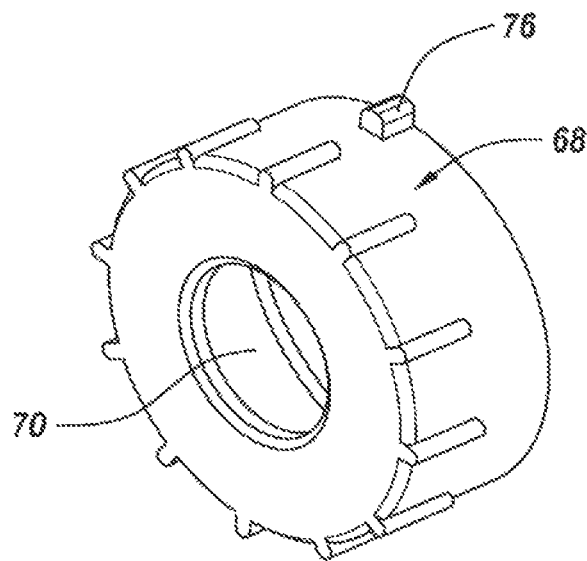
Figure 5C:
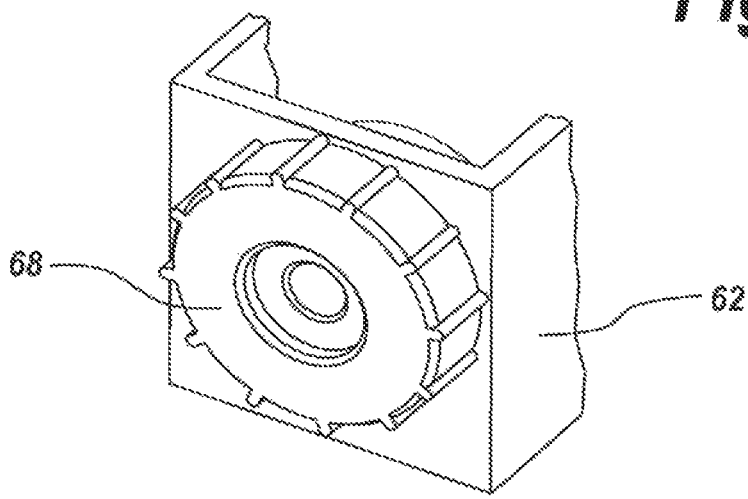

FIG. 4 illustrates an infusion pump 12 having the manifolds 14A, 14B formed within the housing 62 of the pump. The reservoirs 16A, 16B can take many forms, and can include vials, cartridges or ampoules of selected medicaments, such as insulin and glucagon. As set forth above, the internal manifolds can have different or asymmetric feature elements, thus forming dissimilar engagement interfaces. Specifically, the manifolds can have different sizes or shapes so as to only accommodate a reservoir having a similar or complementary size or shape. When constructed in this manner, the system helps prevent the mis-loading of reservoirs in the pump and hence to prevent the mischanneling of medicaments. Once the reservoir having the appropriate feature element is installed in the correct manifold, a cap can be used to close the end of the manifold to ensure that the reservoir does not become dislodged during use.

According to another practice, one or more of the connector or cap, pump housing 62, or reservoir may have asymmetric features that lead to dissimilar engagement interfaces in terms of loading a selected reservoir. Specifically, a separate connector or adapter type feature element can be used in connection with the reservoir and/or pump housing to create the dissimilar interface. Examples of suitable asymmetric feature elements, as set forth above, can include slots with inside versus outside threads (matched by their corresponding caps), slots with distinct bayonet style latching mechanisms, slots, reservoirs or manifolds with corresponding docking keys or keyways, or a combination of these features, so as to help prevent the mis-loading and mischanneling of the incorrect medicament.

The feature elements (such as adapters or connectors) may be permanently or temporarily attached to one or more of the medicament reservoirs 16A, 16B so that they are distinguishable in terms of their connector ends, cross-sections, shapes, profiles, grooves, threading, or other properties. As such, each medicament reservoir uniquely matches its corresponding slot in the pump housing and/or uniquely connects to its corresponding infusion tube, including any associated connector, septum, or piercing element. Alternatively, the reservoir can have a neck or head portion that is configured to have a selected feature element (e.g., differently shaped necks) that are designed to match selected connectors employed therewith. The pump housing can further be designed to accommodate a selected connector only at a selected location (e.g., a selected manifold), thus creating fluid specific pathways.

As shown in FIGS. 4-6D, the pump housing 62 can include a plurality of inlet ports or slots 64, 72. The inlet port 64 and associated cap 68 can be designed to mate together. For example, one or more of the inlet ports 64, 72 can have a feature element formed thereon that is adapted to mate with a corresponding feature element formed on the cap 68. FIGS. 5A-5C show the inlet port 64 having formed thereon a corresponding groove 74. The cap 68 can be configured to cooperate and mate with the inlet port to form for example a bayonet style mount. For example, the cap can include a pair of pins 76 that extend outwardly from the cap surface.

The cap can also function as a connector whereby it mates with a selected feature element formed on the reservoir, such as on the neck portion thereof. According to the illustrated embodiment, the cap can optionally include a central passage 70 that is sized and configured to seat over an end or neck portion 58 of a selected reservoir. The reservoir 16A can include a neck portion having a selected size and/or shape that is adapted to seat within the central passage 70 of the cap 68 or designed to couple with the cap. After the reservoir 16A is mounted within the corresponding manifold 14A, the cap 68 is inserted in the inlet port 64 by aligning the pins 76 with the keys or grooves 74, inserting the cap over the end of the appropriate reservoir in the appropriate slot, and then turning the cap to lock the cap to the pump housing. This arrangement serves to ensure that the correct reservoir is mounted and retained within the correct reservoir.

In some embodiments, the cap 68 may mate directly with the reservoir 16A, such as by permanently capturing the neck portion 58 of the reservoir 16A. Alternative or in addition, any combination of elements 68, 86, and 87 may mate with the reservoir 16A. In some embodiments, the neck portion 58 of the reservoir 16A may be provided with a feature that corresponds to a feature on the cap 68, so that the cap 68 may mate with and permanently capture only a single type of reservoir 16A (and not mating with and capturing the other reservoir 16B).

Alternatively or in addition, the cap 68 may mate with a feature of the inlet of the infusion pump 12, such as by mating threading or other non-permanent securing features. The cap 68 may be designed to mate with only one inlet of the infusion pump.

By combining the permanent mating of the cap 68 with one type of reservoir 16A and one inlet of the infusion pump, an appropriate reservoir 16A may be permanently captured by the cap 68 while the cap 68 mates with an appropriate inlet on the infusion pump 12 in a non-permanent manner. Thus, a two-stage mating to prevent mishandling may be accomplished, which may be particularly useful in the case where the reservoirs 16A, 16B are provided by a third party and it may not be possible to provide distinguishing features on the reservoirs 16A, 16B. Further, the cap 68 with the attached reservoir 16A may be removed and discarded when the reservoir 16A is depleted.

The other inlet port 72 of the pump is adapted to receive a separate reservoir containing a different medicament. The reservoir, cap, and pump housing can be configured in a different manner to accept reservoir 16B while simultaneously being unable to accept reservoir 16A. For example, the inlet can mount a standard cap 78 that secures the reservoir 16B within the pump housing and/or mate with a feature element formed on the neck of reservoir 16B. For example, as illustrated, the neck portions of the reservoirs 16A and 16B can be configured differently.

The infusion pump 12 may include one or more pumping mechanisms 61 for dispensing the medicaments from the reservoirs 16A, 16B. In an exemplary embodiment, the pumping mechanism 61 may be a lead screw for actuating a plunger at the rear of each of the reservoirs 16A, 16B. By pushing on the plunger, medicament may be forced out of the front of the reservoirs 16A, 16B. In other embodiments, the pumping mechanisms may include a lever, pneumatically actuated pump, hydraulically actuated pump, electrical pump, or any other device suitable for exerting pressure on, or otherwise dispensing medicament from, the medicament reservoirs 16A, 16B. The pumping device may be driven by a motor 63, such as an electric motor. The motor 63 may be powered, for example, by batteries 65 disposed in the pump housing 62.

In exemplary embodiments, the infusion pump 12 may be provided with hardware and/or software control logic associated with the pumping mechanism 61. For example, one of the medicament reservoirs 16A, 16B may include less medicament than the other reservoir, or may be smaller than the other reservoir. In order to further ensure that the wrong reservoir is not inserted into the wrong inlet port, the logic may prevent the infusion pump 12 from dispensing the medicament if the pumping mechanism 61 fails to make contact with a plunger on the end of one of the reservoirs 16A, 16B after being extended for more than a predetermined threshold distance.

For example, if one of the medicaments is insulin and the other medicament is glucagon, the glucagon may be provided in the medicament reservoir 16A in a smaller amount than the insulin is provided in the medicament reservoir 16B. In one embodiment, the medicament reservoir 16A may include about one-third as much glucagon as the medicament reservoir 16B includes insulin. Even if the reservoirs 16A, 16B are of the same size, the plunger at the rear of the glucagon reservoir 16A will initially be deployed two-thirds of the distance into the medicament reservoir 16A. If the glucagon reservoir 16A is inadvertently inserted into the slot intended for the insulin, then the pumping mechanism 61 will need to extend much further than expected in order to make contact with the plunger at the rear of the medicament reservoir 16A. Once it is determined that the pumping mechanism 61 has extended to or more than the predetermined extension distance, logic in the infusion pump 12 may recognize that a problem has occurred and may prevent medicament from being dispensed. Optionally, an error warning indicating that the wrong reservoir 16A has been inserted into the wrong inlet port may be displayed on a display device of the infusion pump 12.

The above process may be employed with a minimum threshold as well. For instance, if in the above example the insulin reservoir 16B is inadvertently inserted into the inlet slot intended for the glucagon, then the pumping mechanism 61 may extend only a short distance before making contact with the plunger at the rear of the reservoir 16B. Because logic stored in the infusion pump 12 expects that it will be necessary to extend the pumping mechanism more than a minimum threshold distance in order to make contact with the plunger, the infusion pump 12 may prevent medicament from being dispensed and an error warning may be displayed.

Alternatively or in addition to the above embodiments, the pumping mechanism 61 for one of the medicament reservoirs 16A, 16B may be initially deployed at a different distance than the other pumping mechanism 61. In the above example, the pumping mechanism 61 associated with the inlet slot intended for the glucagon reservoir 16A may be initially deployed further than, or in a more extended position than, the pumping mechanism 61 associated with the inlet slot intended for the insulin reservoir 16B. In this case, it may be difficult or impossible to insert the insulin reservoir 16B into the slot intended for the glucagon 16A, since the plunger at the rear of the insulin reservoir 16B will make contact with the pumping mechanism 61 for the glucagon slot before the insulin reservoir 16B is fully inserted. This may provide a further mechanism for preventing the wrong medicament reservoir from being inserted into the wrong inlet slot.

One of ordinary skill in the art will understand that the configuration depicted in FIG. 4 is intended to be exemplary. Other suitable configurations for an infusion pump 12 may use more, fewer, or different parts.

FIGS. 6A-6D illustrate other embodiments of the present invention where the system can employ asymmetric interfaces to help prevent the mis-loading of reservoirs in the incorrect manifold to help prevent the mischanneling of medicaments. The illustrated infusion pump 12 has inlet ports 72, 64 that are specially configured to receive connectors or caps 84, 86 respectively. The inlet port 72 can have associated therewith a feature element, such as a threaded adapter 88 and the inlet port 64 can associated therewith a threaded adapter 90. The adapter 88 can be configured as a female threaded connector that is adapted to receive and secure a cap 84 having formed thereon a male threaded region 80. The adapter 90 can be configured as a male threaded connector having an external threaded region 82 that is adapted to receive and secure a cap 86 having formed therein a set of female threads 94.

The manifold adapted to receive the reservoir 16A can be sized to accommodate only the reservoir 16A, and the manifold adapted to receive the reservoir 16B can be sized to accommodate only the reservoir 16B. Thus, when the reservoir 16A is seated within the corresponding manifold, the cap 86 is threaded on the male threaded region 82 of the adapter 90. Similarly, when the reservoir 16B is seated within the corresponding manifold, the threaded region 80 of the cap 84 is threaded into the female threaded region 94 of the adapter 88. The adapters, caps and manifolds thus form fluid pathways that are specific to the reservoirs 16A and 16B such that the reservoirs are unable to be mounted within the other manifold. This asymmetric arrangement helps prevent the mis-loading of reservoirs in the incorrect manifold, thus helping to prevent the mischanneling of medicaments.

In some embodiments, there may be multiple points of capture at the inlet or outlet ports of the infusion pump 12.

For example, the reservoirs 16A, 16B may be provided with collars or swages 83 that may be permanently or non-permanently captured by one or more prongs or other capture devices placed or formed on the caps 84, 86. The caps may non-permanently attach to the infusion pump 12 through the threading 80, 90. If the caps 84, 86 permanently capture the collars 83 of the medicament reservoirs 16A, 16B, then the medicament reservoirs 16A, 16B may be withdrawn from the infusion pump 12 when the caps 84, 86 are removed from the infusion pump 12.

Figure 6A:
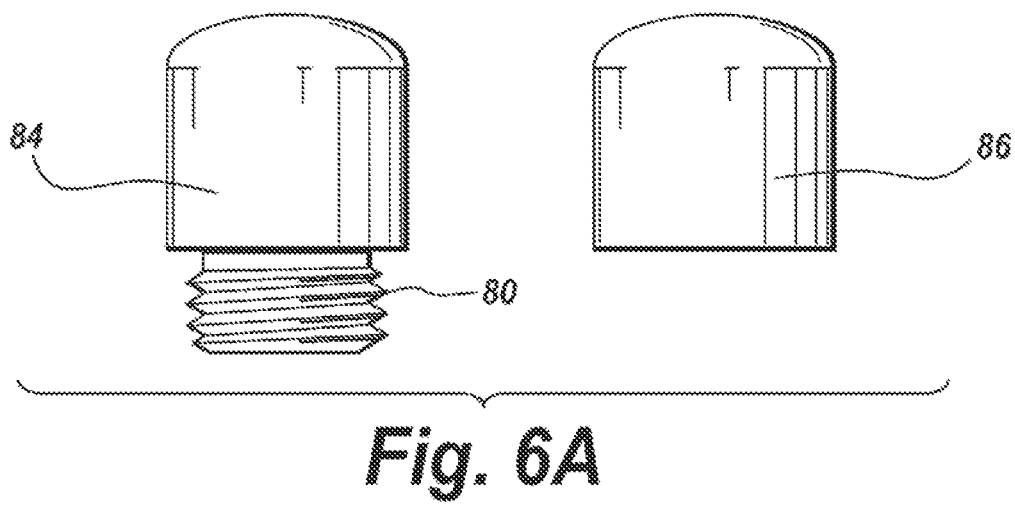
FIGS. 6A-6D illustrate another example of the different types of feature elements that can be used in connection with the inlet ports of the infusion pump of FIG. 4 according to the teachings of the present invention.
Figure 6B:
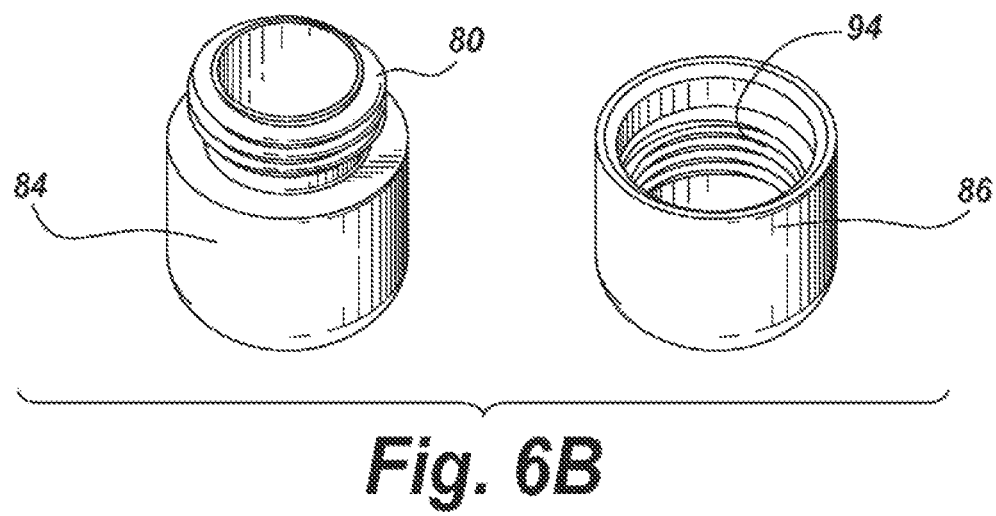
Figure 6C:
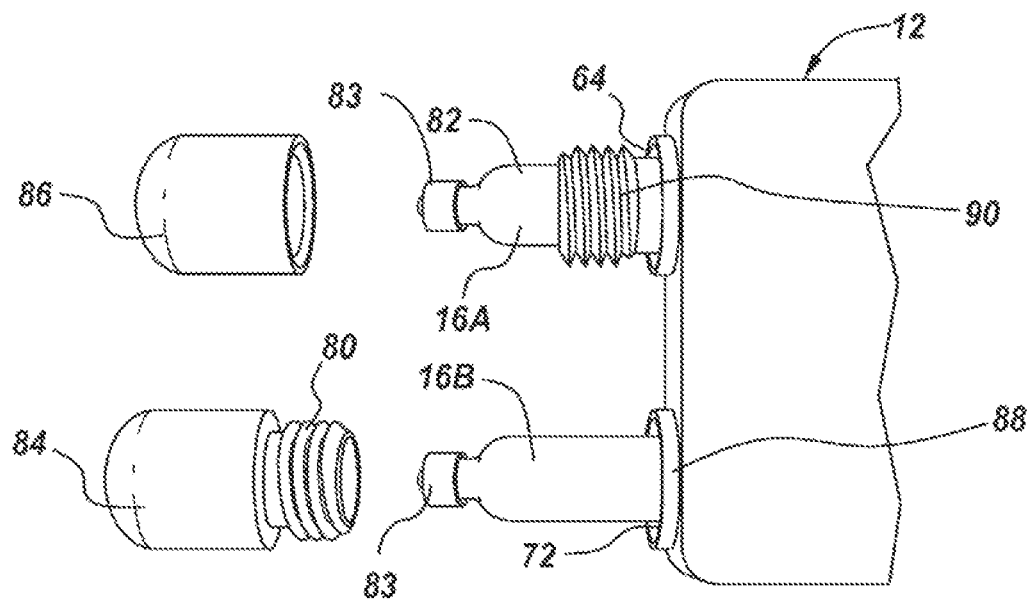
Figure 6D:
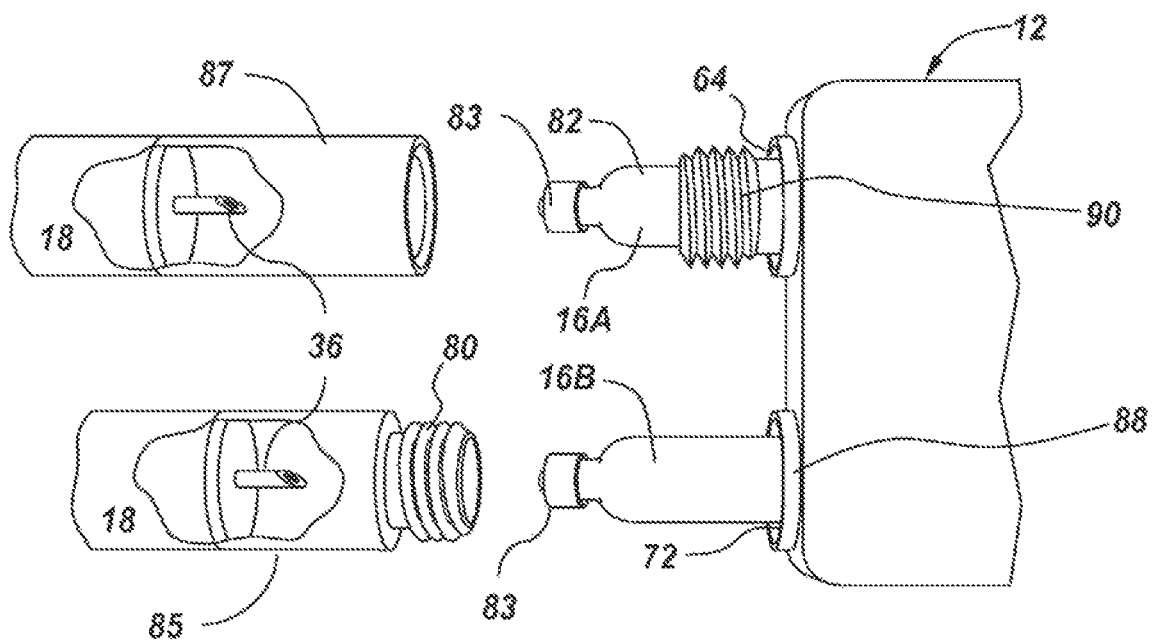

Another embodiment is shown in FIG. 6D. In this embodiment, the multichannel lumen assembly 18 includes male or female threading to allow the lumen assembly 18 to connect directly to the infusion pump 12. The lumen assembly 18 may include in one channel thereof a piercing element such as needle 36 that is positioned inside of and near the end of the lumen 18. The needle 36 may function similarly to the needle 36 of the manifold 14, described above, in that the needle 36 may pierce the septum end of the medicament reservoir 16A, 16B and receive medicament pumped from the reservoir 16A, 16B by the infusion pump 12.

Thus, in this embodiment the inlet ports 72, 64 of the infusion pump 12 serve to receive the medicament reservoirs for pumping by the infusion pump 12, and furthermore serves as the outlet ports of the infusion pump 12. Accordingly, the interface between the lumen assembly 18 with an internal needle 36 and the inlet ports 72, 64 of the infusion pump 12 forms an integrated inlet/outlet port for the infusion pump 12.

The embodiments of FIGS. 6C and 6D may also be combined. For example, caps 84, 86 may be respectively provided with needles 36 mounted inside the caps 84, 86. The lumen 18 may connect to the rear of the caps 84, 86, and may be secured in the caps (for example) by an adhesive. The lumen assembly 18 be affixed to a channel in the cap that is fed by the needle 36. The caps 84, 86 may be attached to the infusion pump 12 by any suitable mechanism, including those shown in FIGS. 7A-7C. The collars 83 of the reservoirs 16A, 16B may be permanently captured by the caps so that, when the combined lumen 18 and cap 84, 86 is removed, the reservoir 16A, 16B is removed along with the lumen 18 and cap 84, 86.

Figure 7A:
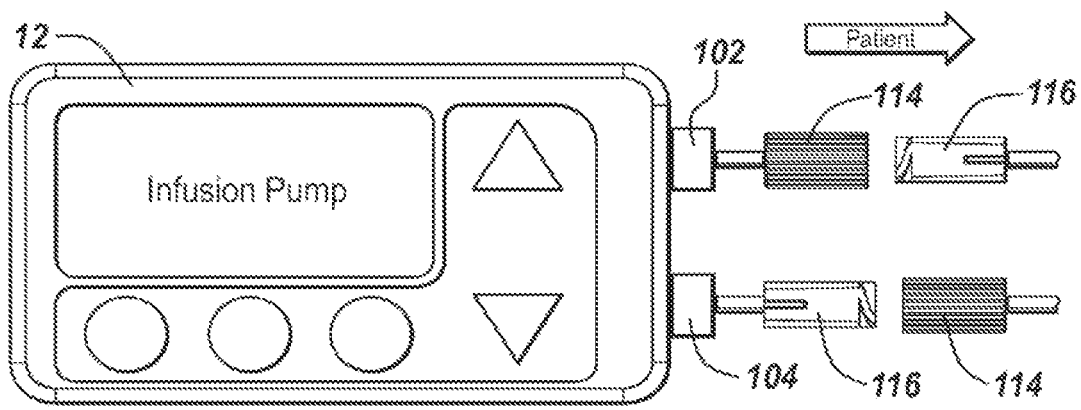
FIGS. 7A-7C illustrate the different types of feature elements that can be used in connection with the outlet ports of the infusion pump of the infusion system of FIG. 1 according to the teachings of the present invention.

FIGS. 7A-8C illustrate other feature elements that can be mounted on the inlet or outlet ports of the infusion pump 12 and on the inlet ports or connector ends of the tubes or channels forming the multi-channel lumen assembly 18 to help prevent the mischanneling of medicaments by the use of unique coupling methods for each medicament. Those of ordinary skill in the art will readily recognize that the infusion pump 12 can have inlets formed as separate inlet and outlet ports, or combined inlet/outlet ports. FIGS. 7A and 8A show an infusion pump 12 having outlet ports 102, 104 formed therein. The outlet ports are adapted to be coupled to the multi-channel lumen assembly 18. In this regard, the multi-channel lumen assembly can comprise for example a pair of tubes that can be attached and detached as desired. Each tube of the multi-channel lumen assembly 18 is adapted to be coupled to a particular outlet port of the infusion pump so as to deliver medicaments to the patient via the infusion set 20. The tubes of the multi-channel lumen assembly and the outlet ports of the infusion pump can include feature elements, such as selected connectors or adapters, that create multiple unique fluid pathways between specific medicament reservoirs and infusion sites. As shown, the outlet port 102 can have a first feature element, such as a female portion 114 of a bayonet style connector, coupled thereto. The corresponding feature element, such as a male portion 116 of the bayonet style connector, can be coupled to a first tube of the multi-channel lumen assembly 18. A similar feature element can be coupled to the second outlet port. Specifically, the outlet port 104 can have the male portion 116 of the bayonet style connector coupled thereto. The corresponding female portion 114 can be coupled to a second tube of the multi-channel lumen assembly 18. The male portion 116 of the connector has formed at a mating end thereof an engagement portion 118 configured as a partial thread. The female portion 114 of the connector has internal threads (not shown) formed in a rotatable housing that is adapted to engage the engagement portion 118 of the male portion of the connector. In order to couple the two connector portions together, the male portion is inserted into the female portion and then the female portion is rotated so as to lock the two portions together.

When the tubes of the multi-channel lumen assembly are coupled to the outlet ports as described above, the infusion system creates a pair of specific, dedicated and non-interchangeable fluid pathways. The first tube that is coupled to the male connector can only be connected to the outlet port 102 and the second tube that is coupled to the female connector can only be coupled to the outlet port 104.

Figure 7B:
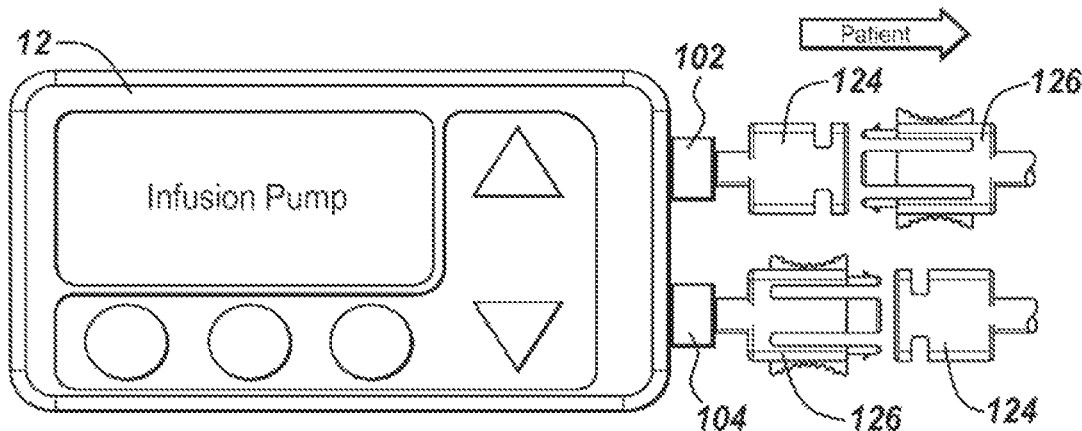

FIGS. 7B and 8B illustrate another embodiment of a feature element that can be used to form specific fluid pathways between selected medicament reservoirs and the infusion sites in order to help prevent the mischanneling of medicaments. The illustrated infusion pump 12 has outlet ports 102, 104 formed therein. The outlet ports are adapted to be coupled to the first and second tubes of the multi-channel lumen assembly 18. Each tube of the assembly 18 is adapted to be coupled to a particular outlet port of the infusion pump so as to deliver particular medicaments to the patient via the infusion set 20. As shown, the outlet port 102 can have a first feature element, such as a female connector portion 124, coupled thereto. The corresponding feature element, such as a male portion 126, can be coupled to the first tube of the multi-channel lumen assembly 18. A similar feature element can be coupled to the second outlet port. Specifically, the outlet port 104 can have the male portion 126 of the feature element coupled thereto. The corresponding female portion 124 can be coupled to the second tube of the multi-channel lumen assembly 18. The male portion 126 of the connector has formed at a mating end thereof an engagement portion 128 configured as a spaced pair of flexible legs 130. The female portion 124 of the connector has a pair of grooves 132 formed therein that are sized and configured to engage the legs 130 of the male portion of the connector. To couple the two connector portions 124, 126 together, the legs of the male portion 126 are inserted into the female portion 124 until the legs engage and seat within the grooves 132 so as to lock the two portions together. Similar to the connectors 114, 116, when the tubes of the multi-channel lumen assembly are coupled to the outlet ports as described above, the infusion system creates a pair of specific and non-interchangeable fluid pathways. That is, the first tube that is coupled to the male connector can only be connected to the outlet port 102 and the second tube that is coupled to the female connector can only be coupled to the outlet port 104.

Figure 7C:
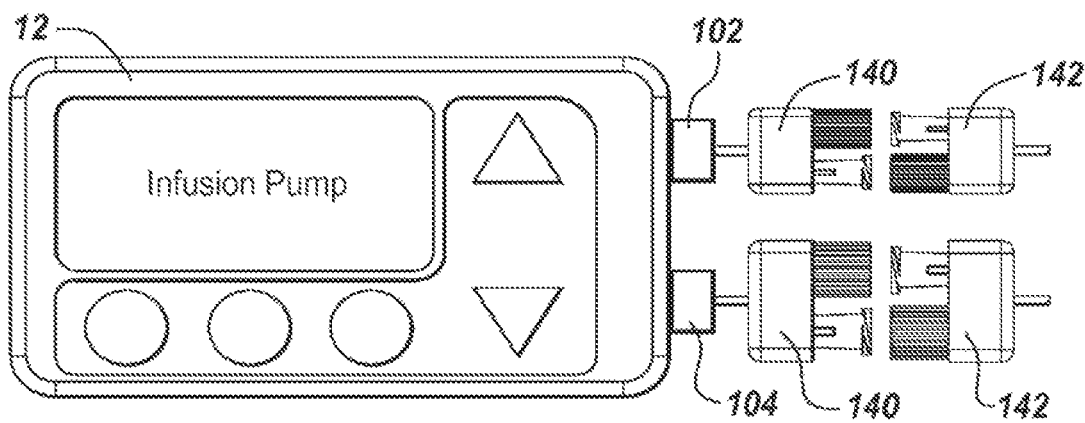
Figure 10A:
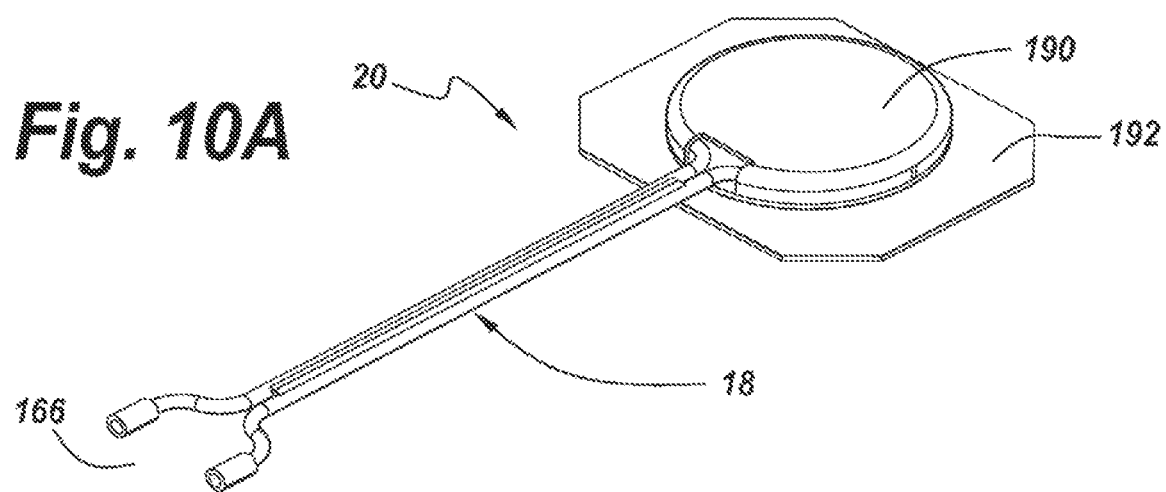
FIG. 10A is a perspective view of the infusion set portion of the infusion system of FIG. 1 illustrating the fluid connection between the multi-channel lumen assembly and the infusion set according to the teachings of the present invention.
Figure 10B:
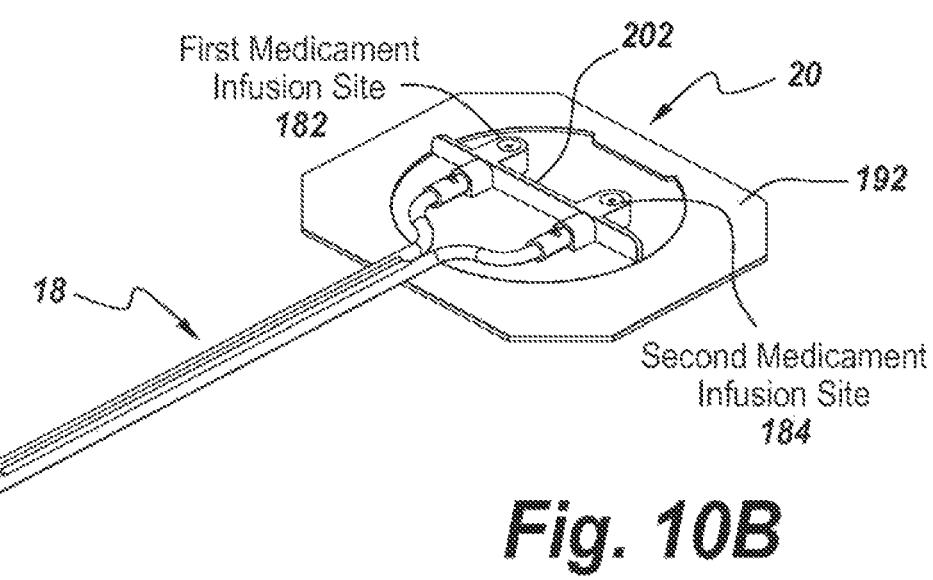
FIG. 10B is a perspective view of the infusion set portion of the infusion system of FIG. 1 illustrating the fluid connection between the multi-channel lumen assembly and the infusion set with the cover removed according to the teachings of the present invention.
Figure 10C:
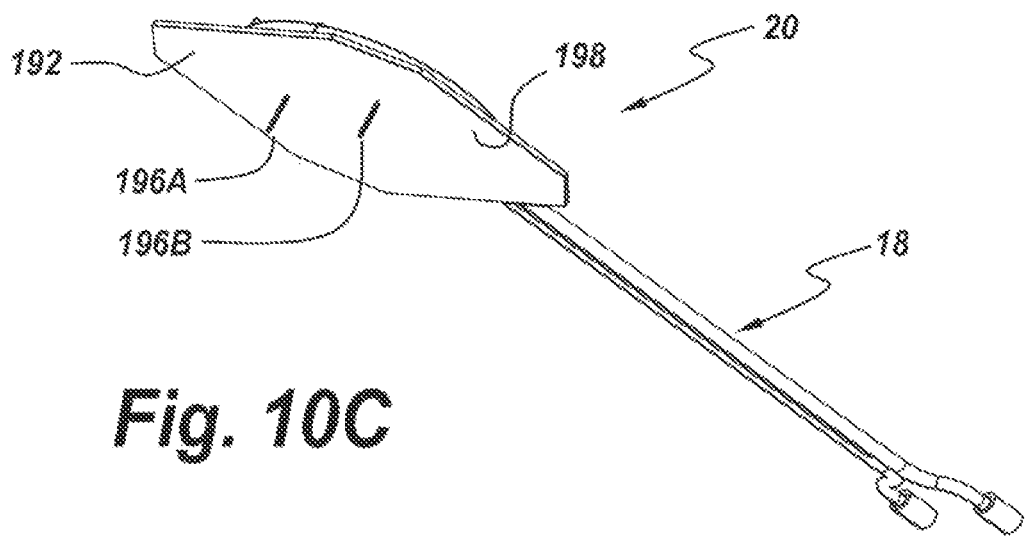
FIG. 10C is a perspective view of an underside of the infusion set portion of the infusion system of FIG. 1 according to the teachings of the present invention.
Figure 11:
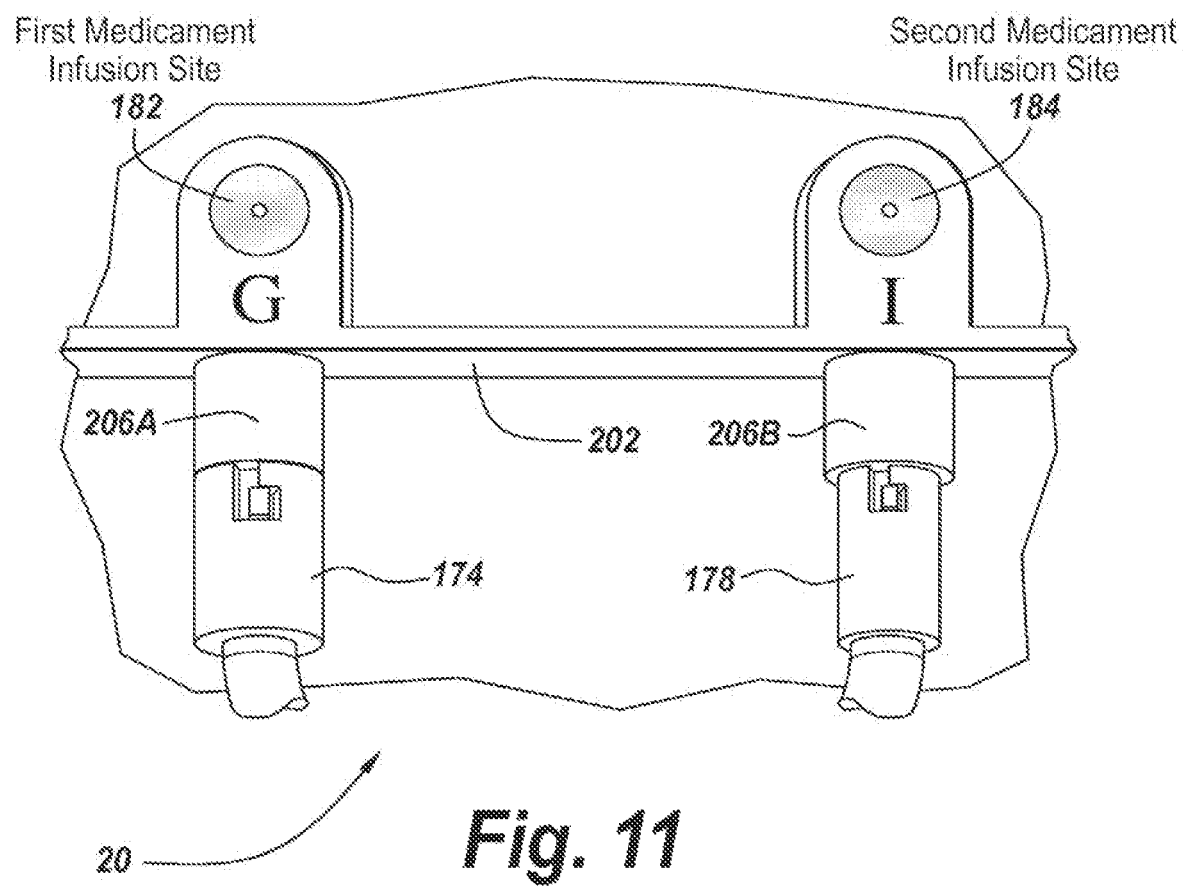
FIG. 11 is a partial exploded view of the infusion site portion of the infusion set according to the teachings of the present invention.
Figure 12:
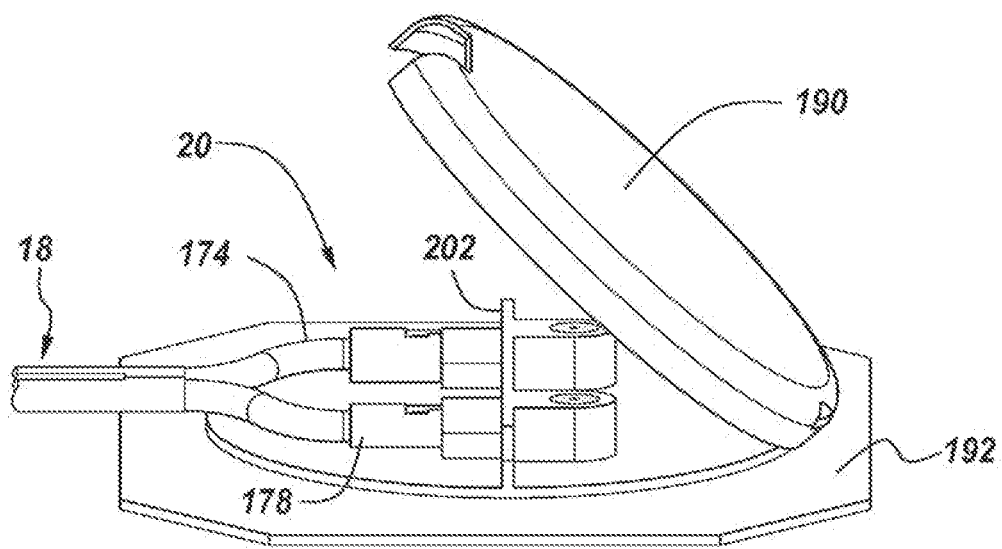
FIG. 12 is an exploded perspective view of the infusion site portion of the infusion set according to the teachings of the present invention.

FIGS. 7C and 8C illustrate still another embodiment of a feature element that can be used to form specific fluid pathways between selected medicament reservoirs and the infusion sites in order to help avoid the mischanneling of medicaments. The illustrated infusion pump 12 has outlet ports 102, 104 formed therein. The outlet ports are adapted to be coupled to the first and second tubes of the multichannel lumen assembly 18 so as deliver medicaments to the patient via the infusion set 20. As shown, the outlet port 102 can have a first portion 140 of a selected feature element having a base portion 144 that has attached thereto a female connector portion 134 and a male connector portion 136. A corresponding second portion 142 of the feature element can be coupled to the first tube of the multi-channel lumen assembly 18. The second feature element portion 142 also includes a base portion 144 having attached thereto a female connector portion 134 and a male connector portion 136, where the positions of the male and female connector portions are reversed so as to be able to properly engage the connector portions of the first feature element portion 140.

A similar feature element can be coupled to the outlet port 104. Specifically, the outlet port 104 has the first portion 140 of the feature element attached thereto. The first feature element can also have a base portion 144 having attached thereto the female connector portion 134 and the male connector portion 136. The corresponding second portion 142 of the feature element can be coupled to the second tube of the multi-channel lumen assembly 18. The second feature element portion 142 also includes a base portion 144 having attached thereto a female connector portion 134 and a male connector portion 136, where the positions of the male and female connector portions are reversed so as to be able to properly engage the connector portions of the first feature element portion 140. In order to couple the two connector portions 140, 142 together, the male and female portions of the first portion 140 are inserted into the corresponding male and female portions of the second portion 142 so as to lock the two portions together. Further, the first and second portions 140, 142 of the feature element coupled to the first outlet 102 and the first tube of the multi-channel lumen assembly can have a first selected size that is smaller than the size of the connector portions 140, 142 coupled to the second outlet port 104, as shown. This size difference ensures that the first tube can only be coupled to the first outlet 102 and that the second tube can only be coupled to the second outlet 104. Similar to the connectors 114, 116, 124, and 126, when the tubes of the multi-channel lumen assembly are coupled to the outlet ports as described above, the infusion system creates a pair of specific and non-interchangeable fluid pathways.

The first and second portions 140, 142 of the feature element can also be configured to include additional features such as unique keys or grooves such that they uniquely engage with the ends of the connectors that are distal (i.e., attached to the tubes) to the infusion pump and that are of matching sizes and shapes.

With reference to FIGS. 1, 2, 9A and 9B, the multi-channel lumen assembly 18 of the infusion system 10 is shown in more detail. The multi-channel lumen assembly is typically provided to help convey the medicaments from the infusion pump to the infusion set 20. The manner of connection between the multi-channel lumen assembly 18 and the site of infusion and/or infusion pump can employ feature elements (e.g., asymmetric positioning features) to ensure the correct channeling of medicaments to the patient. The infusion set 20 can also incorporate a channeling system that can pair with each of the tubes or channels of the multi-channel lumen assembly that spans the gap between the infusion pump and the site of infusion. The infusion set can be connected, disconnected, or reconnected with the multi-channel lumen assembly. The infusion set preferably infuses medicaments to the patient through multiple channels. These channels can infuse medicaments intradermally, subcutaneously, intramuscularly, or intravenously using one or more piercing elements, as is known in the art. Those of ordinary skill in the art will readily recognize that the tubing assembly can be combined with the infusion set to form, when coupled to the infusion pump, the infusion system 10 of the present invention. However, for purposes of clarity, the tubing assembly will be discussed separately from the infusion set 20.

The illustrated multi-channel lumen assembly 18 includes first and second tubes 150 and 152, respectively, forming medicament passages or channels. For example, the first tube 150 forms a medicament channel 154 and the second tube 152 forms a medicament channel 156. As described above in connection with FIGS. 7A-8C, the end portions of the first and second tubes can include if desired a feature element to help prevent the mischanneling of medicaments. For example, either or both end portions 172 and 174 of the first tube 150 can employ the feature element, and similarly either or both of the end portions 176 and 178 of the second tube 152 can employ a feature element. The first ends 172 and 176 of the first and second tubes 150 and 152, respectively, form the infusion pump side 166 of the multi-channel lumen assembly 18. The second ends 174 and 178 of the first and second tubes 150 and 152, respectively, form the infusion set side 168 of the multi-channel lumen assembly 18.

The tubes 150 and 152 of the multi-channel lumen assembly 18 can be configured so as to be able to be coupled together and then, if desired, be detached or decoupled from each other. This can preferably be done repeatedly. As shown in FIGS. 9A and 9B, the tubes 150 and 152 can have formed thereon mating connecting features that allow the tubes to be coupled together over at least a portion of the length of the tubes. According to one embodiment, the first tube 150 can employ a surface feature, such as a tongue-like rail portion 160, that is formed on and extends outwardly from the main body of the tube 150. The second tube can have formed thereon a surface feature, such as an extension portion having a groove 162 formed therein, that is complementary to the surface feature 160. Hence, the first and second tubes can be coupled together by inserting the tongue 160 of the first tube into the groove 162 of the second tube along the length of the groove. The ability to repeatedly couple and decouple the tubes of the multi-channel lumen assembly allows the patient significant flexibility in using the infusion system, and especially the multi-channel lumen assembly. Moreover, the patient can replace one or both of the tubes as needed rather than dispose of both tubes at the same time as is required in prior art systems. That is, in prior art systems, the first and second tubes are permanently coupled together. Those of ordinary skill in the art will readily recognize that other types of surface features can be used to join the first and second tubes together, while concomitantly providing the ability to repeatedly decouple the tubes from each other when needed, such as by spliced joints and the like. Moreover, the tubes of the multi-channel lumen assembly can be formed of any suitable material, such as plastic. Those of ordinary skill will readily recognize that the multi-channel lumen assembly can include more than two tubes or can include a single tube forming multiple channels. Further, the channels can include a single passage, as illustrated, or each tube can include multiple channels or lumens.

Furthermore, as shown in FIG. 2, the tubes 150 and 152 can be coupled together along at least a portion of the length of the tubes, such as by webbing or by feature elements such as those described above in connection with FIGS. 9A and 9B. This connection can be either permanent along at least a portion of the length of the tubes, or the connection can be configured to allow the tubes to be easily separated from each other and reconnected as appropriate. The tubes 150 and 152, however, are not connected together in a region adjacent the infusion set 20. That is, the infusion set can be formed into a pair of separate and distinct medicament administration regions that are spaced from each other.

FIGS. 1, 2, and 10A-14C illustrate the infusion set 20 according to the teachings of the present invention. Those of ordinary skill in the art will readily recognize that the use of an infusion pump requires the use of a disposable component, typically referred to as an infusion set, which helps convey the medicament from the reservoir and pump into the skin of the patient. Conventional infusion sets typically consist of a pump connector, a tubing assembly, and a hub or base from which one or more piercing elements extend therefrom. The piercing element can include for example a needle, infusion cannula, a flexible catheter and the like. The hub or base has an adhesive (not shown) which retains the base on the skin surface during use, and which may be applied to the skin manually or with the aid of a manual or automatic insertion device. In most cases, a detachable fluid connector is provided to allow the pump tubing to be disconnected from the hub or base when the user wishes to shower, bathe or swim.

The infusion set 20 of the present invention includes a multi-channel infusion device where each channel infuses a medicament into the patient. The channels are connected to the infusion sites by way of asymmetric positioning feature elements that help prevent the mischanneling of medicaments. The medicaments can be supplied from a single or multichannel system or directly from one or more medicament sources, such as a pumping system having one or more external or internal medicament reservoirs. The infusion set infuses medicaments either intradermally, transdermally, subcutaneously, and/or percutaneously.

The multi-channel lumen assembly 18 is coupled to the infusion set 20. The infusion pump side 166 of the multi-channel lumen assembly 18 can include one or more feature elements, as described above in connection with FIGS. 7A-9B, that only allows the tubes of the multi-channel lumen assembly 18 to connect to particular medicament reservoirs, thus preventing the mischanneling of medicaments. Likewise, the infusion set side 168 of the multi-channel lumen assembly 18 can also include one or more feature elements that help prevent the mischanneling of medicaments. In this regard, the feature elements are adapted to interface with like feature elements formed in the infusion set.

The illustrated infusion set 20 includes a base portion 192 that seats the medicament delivery components of the infusion set. The infusion set can include one or more infusion sites having associated therewith one or more piercing elements. The piercing elements can be formed from any suitable material, including metal and non-metal materials. According to one embodiment, the delivery components can include multiple piercing elements, such as first and second spatially separated cannulas 196A and 196B, a portion of which protrude from an underside or bottom surface 198 of a common base 192. The cannulas form first and second medicament infusion sites 182 and 184 from the common base. The cannulas can be attached to the base portion 192 via a support structure 202. The support structure forms inlet ports 206A and 206B. The connector ends 174, 178 of the tubes of the multi-channel lumen assembly 18 are adapted to couple with the inlet ports 206A, 206B, respectively. We describe the embodiments herein as employing cannulas for the sake of simplicity, although those of ordinary skill in the art will recognize that other types of piercing elements can also be used. Moreover, the infusion sites can be formed from a common base 192 or from separate base elements, FIG. 2. Those of ordinary skill in the art will readily recognize that if separate base elements are employed, then each base element can employ one or more piercing elements.

The connector ends 174, 178 and/or the inlet ports 206A, 206B can have the feature elements formed thereon. As shown for example in FIG. 11, the ports and connector ends can preferably mount the respective portion of a bayonet style connector or adapter. The bayonet style connector can be arranged on the connector ends and inlet ports, if desired, such that the connector end 174 only mates with the inlet port 206A and the connector end only mates with the inlet port 206B. In this way, similar to the various feature elements described above, and specifically consistent with the bayonet style adapter illustrated in FIGS. 5A-5C and 8A, the multi-channel lumen assembly 18 and infusion set 20 can create a first discrete fluid pathway in the system solely for the first medicament (e.g., insulin) and a second discrete fluid pathway solely for the second medicament (e.g., glucagon). Thus, the connector ends 174, 178 of the tubes of the multi-channel lumen assembly 18 and the inlet ports 206A, 206B associated therewith can differ by way of for example geometrical, dimensional, and/or positioning physical feature elements that are unique to each medicament source or reservoir.

Figure 13A:
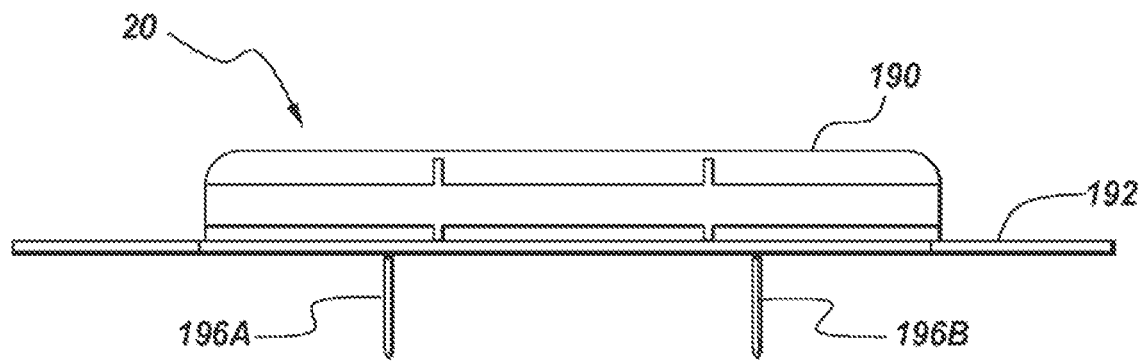
FIG. 13A is a side view of the infusion set having similar cannulas for delivering the medicament to the infusion sites according to the teachings of the present invention.
Figure 13B:
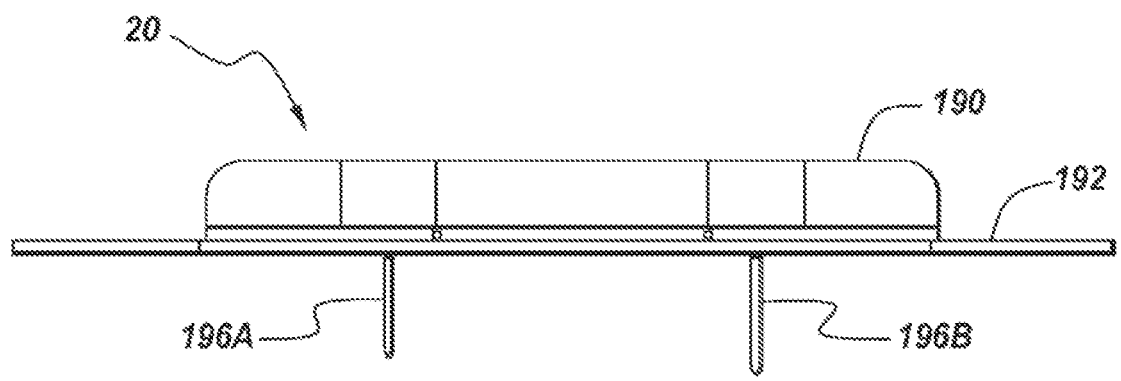
FIG. 13B is a side view of another embodiment of the infusion set employing different types of cannulas for delivering the medicament to the infusion sites according to the teachings of the present invention.
Figure 14:
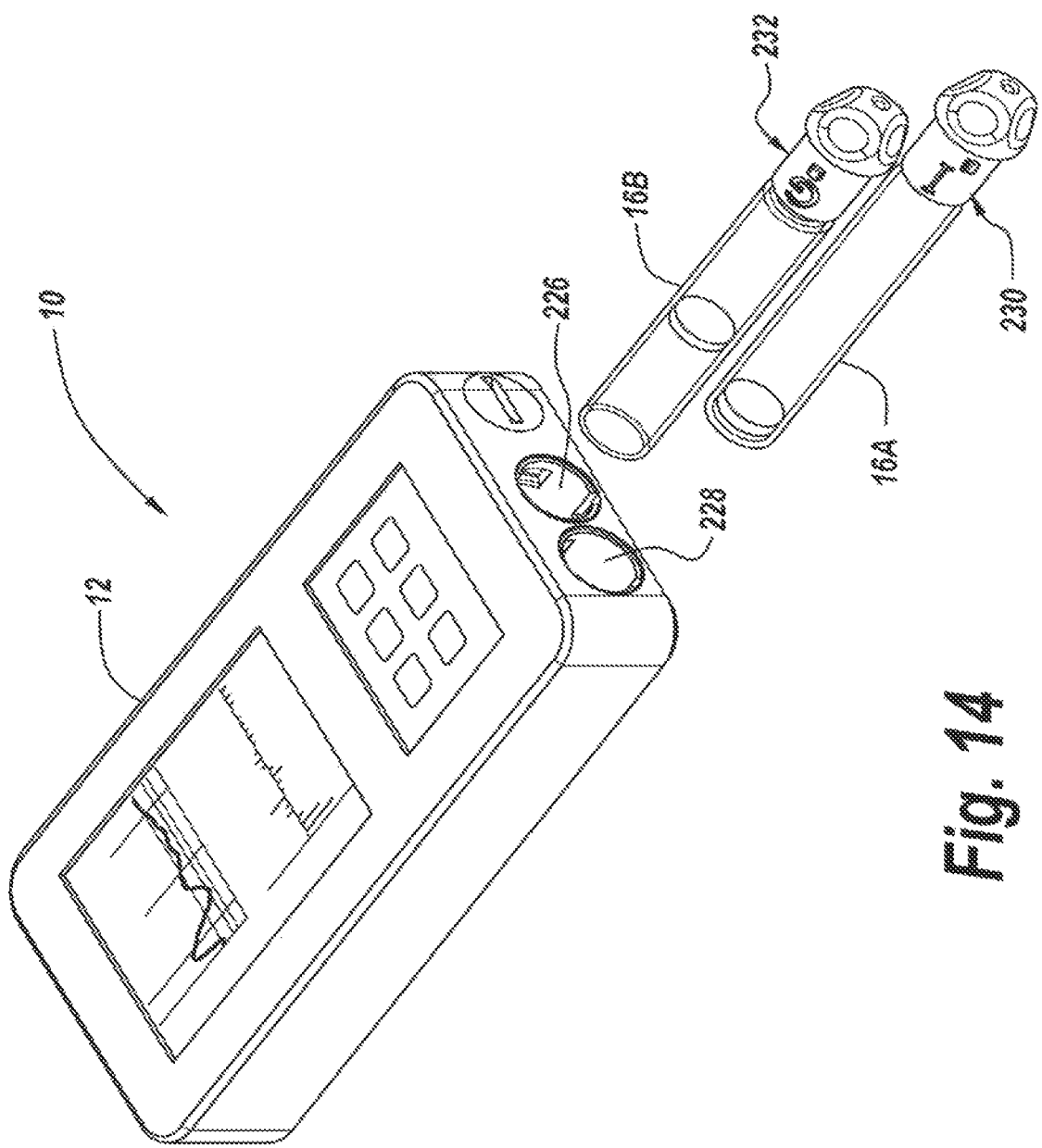
FIG. 14 is a perspective view of another embodiment of the multi-medicament infusion system illustrating the infusion pump with inlet/outlet ports configured for accepting reservoirs with attached coupling for connection to the multi-channel lumen assembly according to the teachings of the present invention.

The medicaments are delivered to the patient at the infusion sites 182, 184 by the cannulas 196A, 196B. As shown in FIG. 13A, the cannulas 196A, 196B can be the same. Specifically, the cannulas can be formed of the same material, such as from metal or non-metal. Alternatively, as shown in FIG. 13B, the cannulas 196A, 196*b* can be different and formed from different materials. According to one practice, the cannula 196A can be formed from metal and the second cannula 196B can be formed form plastic (e.g. Teflon®). The plastic cannula can be introduced into the infusion set via a supplemental device, such as a trocar.

Those of ordinary skill in the art will readily recognize that the cannulas 196A, 196B in the infusion set 20 can be inserted to the same or different depths under the skin. Moreover, the cannulas can have different lengths, shapes, and profiles. Those of ordinary skill in the art will also recognize that the medicaments can be infused into the patient by mechanisms other than the illustrated piercing elements, such as for example by micropore transfer via a transdermal tape activated by chemical, electrical or other means.

A selected cover 190 can be mounted to the base portion 192 be way of, for example, a hinge. The cover 190 serves to cover and hence protect the medicament delivery components of the infusion set 20. Alternatively, the cover 190 can be a static lid, and can if desired be transparent or opaque. The infusion set could also be constructed without a cover. An adhesive can be mounted to the bottom surface 198 of the base 192 so as to secure the infusion set to the infusion site selected by the patient.

The present invention thus contemplates a multi-channel infusion set 20 where each channel infuses a medicament and a manner of connecting to plural infusion sites that uses asymmetric positioning features to prevent the mischanneling of medicaments. The multiple channels of the multi-channel lumen assembly 18 can bridge the span between the infusion sources and the sites of infusion by way of separate, independent channels (where each channel can be a single channel or a multiple-lumen channel), or by way of channels that are joined or coupled together by webbing or by some other manner. The infusion set can also employ one or more septums that prevent the unwanted leaking of medicaments when connecting and disconnecting the ports from the multi-channel lumen assembly 18.

The present invention mitigates the possibility of mis-channeling by connecting the wrong tubing to the wrong infusion cannula by using feature elements having different geometrical, dimensional, and/or positioning physical features that are unique to each medicament source and channel in a manner that uniquely matches the infusion set connection interfaces. The infusion set 20 can be connected, disconnected, or reconnected from the multiple channels in a single engagement step or separately, and the connection provides a secure fluid path from each channel into the infusion sites. The connection between the channels and the infusion set can be released, separately for each channel, and re-connected for multiple use. The infusion set can itself house a channeling system that employs independent channels (where each channel can be a single or multiple-lumen channel), or a single multiple-lumen channel (where the enclosed lumens are arranged in an array, or as concentric lumens), or by any combination of the above.

FIGS. 14-17B and 22 illustrate another embodiment of the multi-medicament infusion system 10 of the present invention. Like reference numerals denoting like or similar structure will be used throughout the various Figures and views. The illustrated infusion system includes an infusion pump 12 having inlets 226 and 228 formed therein. The inlets 226, 228 can be formed as combined inlet/outlet ports as described above in connection with the system illustrated for example in FIG. 4. The manifolds formed within the infusion pump can be sized and configured to accommodate the reservoirs 16A, 16B. The reservoirs are configured to house medicaments. The reservoir 16A has a connector 230 associated therewith and the reservoir 16B has a connector 232 associated therewith. Although not illustrated, the multi-channel lumen assembly 18 can be coupled to the connectors 230, 232 at an end opposite the reservoirs by way of a piercing element assembly. The multi-channel lumen assembly 18 can in turn be coupled to the infusion set 20.

The illustrated infusion system 10 of the present invention provides for one or more selected feature elements or connectors to be disposed on the pump housing, the reservoir, and the connector for ensuring that the proper medicament reservoir is coupled to the proper or correct manifold of the infusion pump 12. This arrangement of components helps prevent the accidental coupling of a reservoir containing a specific medicament to an incorrect manifold. For example, according to one practice, the pump includes two separate manifolds each configured to mate with a specific medicament reservoir. Hence, a first manifold can be adapted to accommodate a first reservoir containing a first medicament, such as insulin, and a second manifold can be adapted to accommodate a second reservoir containing a second medicament, such as glucagon. In this example, it is important to ensure that the glucagon reservoir is not accidentally coupled to the insulin manifold and vice versa. The unique mating connectors and feature elements thus ensure that each portion of the system can only be connected to the system in a unique way or selected configuration, thus preventing the accidental mischanneling of medicaments.

The connectors 230, 232 can have formed therein a piercing element for piercing a septum formed as part of the neck or swage of the reservoirs. The piercing element can be formed as part of a piercing element assembly that seats within a central opening 240 formed in the connector, FIG. 22. For example, the reservoir 16A includes a swage 83 that typically includes a septum and the connector 230 is adapted to be coupled to the reservoir 16A. The reservoir can contain any suitable medicament, and preferably contains insulin. The swage can be constructed to have a feature element, here denoted as a round neck portion, that is adapted to seat within a corresponding and complementary shaped feature element, such as a recess or chamber 234, formed in the connector housing 254. Preferably, the feature elements help form a specific dedicated fluid pathway that helps prevent the mischanneling of medicaments and helps prevent the accidental administration of an incorrect medicament to the patient. The connector is adapted to permanently or non-permanently capture the reservoir 16A, as described further below. According to one practice, the connector when mounted over the swage 83 of the reservoir 16A permanently captures the reservoir.

Figure 15B:
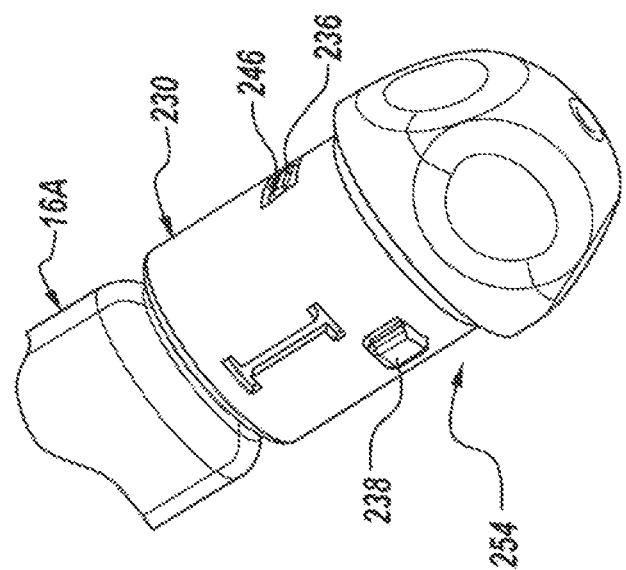
FIG. 15B is a perspective assembled view of the reservoir and coupler portion of FIG. 15A according to the teachings of the present invention.
Figure 15A:
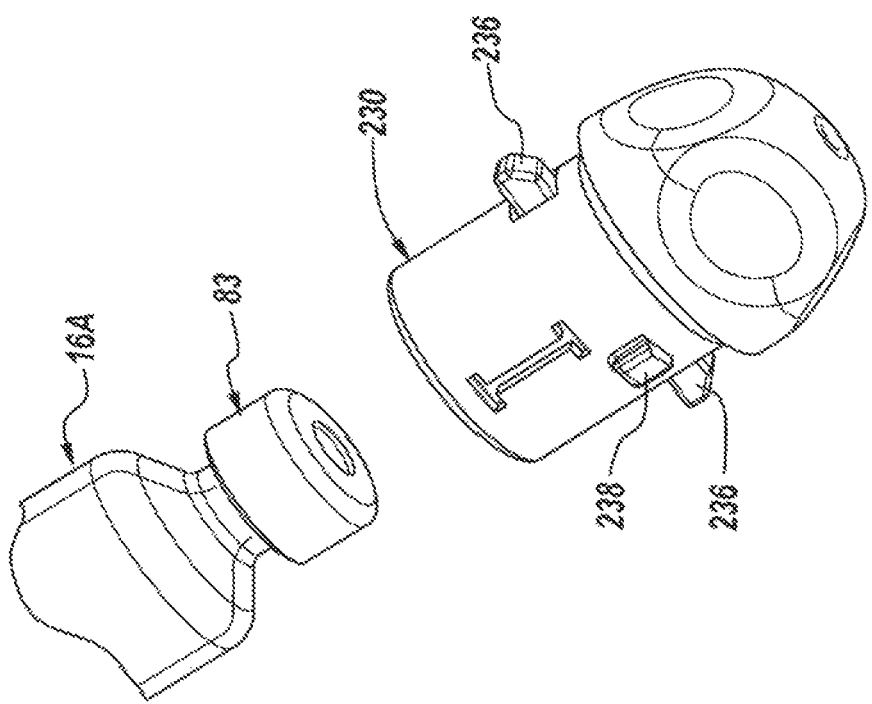
FIG. 15A is a perspective unassembled view of a reservoir and attached coupler having a selected feature element for coupling to a suitable coupler portion with a corresponding feature element according to the teachings of the present invention.
Figure 22:
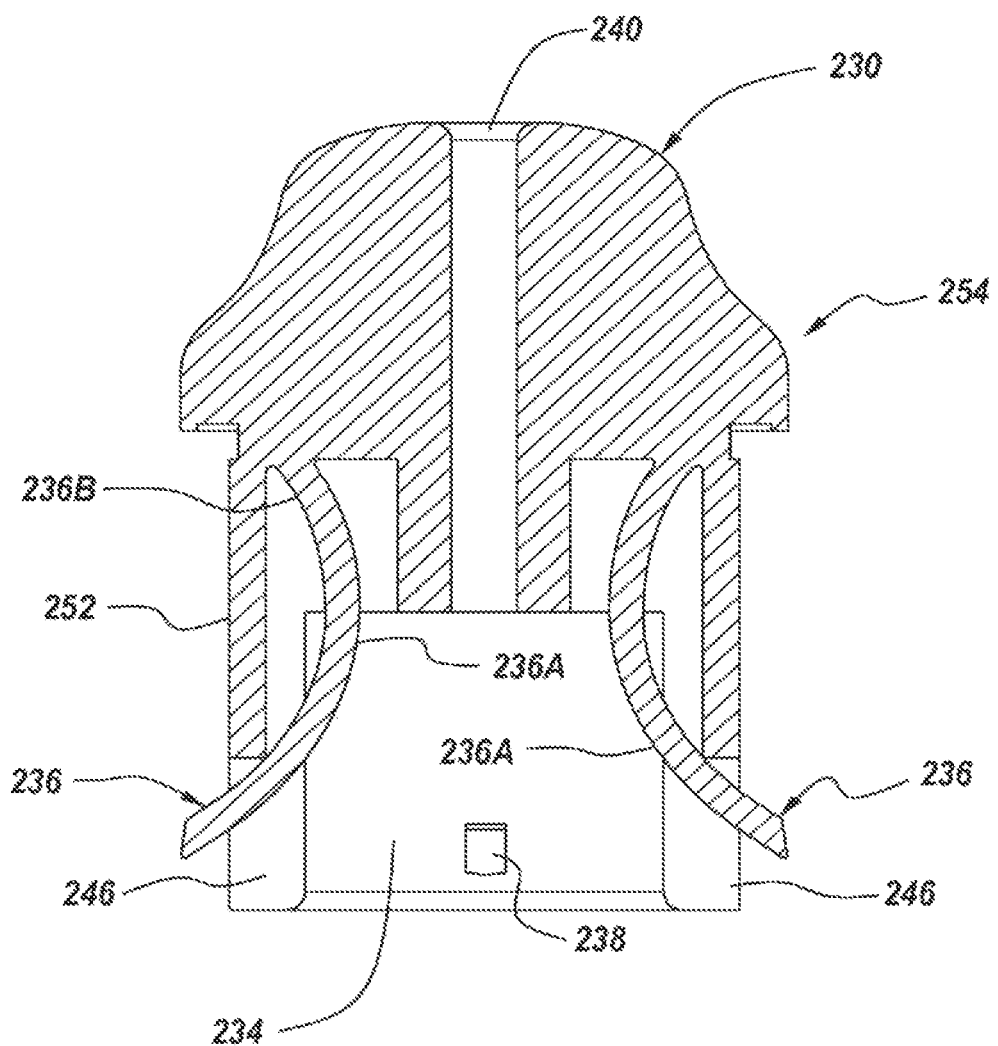
FIG. 22 is a partial cross-sectional view of a connector of the infusion system of the present invention illustrating the configuration of the movable tab according to the teachings of the present invention.

The illustrated connector 230 can also include one or more feature elements in the form of a plurality of surface features 236, 238 that extend outwardly from an outer surface of the connector 230. The surface features can include a plurality of tabs or detents, a subset of which is radially movable relative to the connector housing. According to one practice, the tabs 238 are formed on the outer surface of the connector housing and are fixed in place. That is, the tabs are not radially movable relative to the connector housing. The tabs 236 as shown in FIGS. 15A, 15B and 22 are movable tabs that can be moved between an extended position, where the tabs extend outwardly through an aperture 246 formed in a sidewall 252 of the connector housing, and a retracted position, where the tabs are radially movable such that they are primarily disposed within the housing, such as in the chamber 234. The tabs can be placed on or extend outwardly from the connector housing outer surface at any suitable location and preferably are placed at positions that correspond to the location of feature elements formed on a corresponding inlet or port (e.g., inlet port) of the pump housing, such as port 228. The tabs help prevent the loading of the incorrect reservoir in the pump housing. For example, if the connector is coupled to an incorrect reservoir, the movable tabs will not be disposed in the retracted position. When disposed in the extended position, the tabs prevent the reservoir from being fully placed and seated within the manifold of the pump.

As shown in FIGS. 15A, 15B, and 22, when the connector 230 is separately disposed relative to the reservoir, the tabs of the connector extend radially outwardly from the housing. The reservoir has a feature element formed on a neck portion thereof that is complementary in shape to a feature element formed in the connector. In the illustrated example, the feature element can include a round swage element formed on the neck portion of the reservoir 16A, which in turn seats within a round chamber 234 (i.e., feature element) formed in the underside of the connector. When the connector is coupled to the reservoir 16A, the neck portion engages the movable tabs 236 or any other suitable cooperating structure to move the tabs from the extended position into the retracted position. When coupled together in this manner, the connection between the reservoir and the connector can be non-permanent or permanent in nature, and the reservoir is preferably permanently retained or coupled to the connector.

Those of ordinary skill in the art will readily recognize that any suitable structure can be employed that is capable of moving the exposed portion of the tabs 236 between the extended and retracted positions upon insertion of the neck of the reservoir into the chamber 234 of the connector 230.

According to one practice, the movable tabs 236 can have an elongated, slightly arcuate main body 236A which is attached at one end 236B to the housing of the connector. The opposed free end of the tab extends outwardly through the aperture 246 formed in the sidewall of the housing. In this configuration, the tab is disposed in the extended position. The arcuate structure of the tab provides for a selected amount of resilience and elasticity such that as the reservoir is inserted into the chamber and engages with the tab main body 236A, the flexible tab bends by a selected amount such that the free end portion of the tab that extends through the aperture 246 is retracted inwardly into the chamber 234 and hence into the retracted position. Other tab designs can also be employed in the present invention, including designs where the tab main body has an angled cam surface such that the tab pivots between the retracted and extended positions.

Once the reservoir 16A and the connector 230 are attached together, the combined unit can be mounted within the corresponding port or inlet of the infusion pump 12. According to one practice, the inlet 228 functions as a combined inlet/outlet port or aperture. The inlet 228 preferably has one or more feature elements associated therewith. In the illustrated embodiment, the inlet 228 has a pair of keys or slots 248, FIG. 17A, formed in the inlet at locations that correspond to the locations of the fixed tabs 238 of the connector 230. As shown and not to be construed in a scope limiting way, the keys for example can be spaced apart by about 120 degrees. Those of ordinary skill in the art will readily recognize that the keys can be formed at any selected location provided that they are disposed at locations that are different than those formed in inlet 226, or any other similar inlet formed in the infusion pump 12. Hence, once the movable tabs are disposed in the retracted position by the coupling together of the connector and the reservoir, the combined unit can be mounted within the inlet 228 since the fixed tabs 238 can be aligned with the keys 248 formed therein. Further, the other inlet 226 has feature elements formed at locations that are different than the locations of the fixed tabs 238 of the connector 230, thus preventing the reservoir 16A from being accidentally seated within the incorrect inlet 226. This helps prevent the mischanneling of medicaments and the accidental administration of an incorrect medicament to the patient. Once the tabs 238 are aligned with the keys 248 of the correct inlet 228, the reservoir can be mounted therein, FIG. 17B. The reservoir can be retained within the infusion pump 12 by rotating the connector when coupled to the inlet so that the tabs and the keys are no longer aligned, thus locking the connector in place.

Figure 16B:
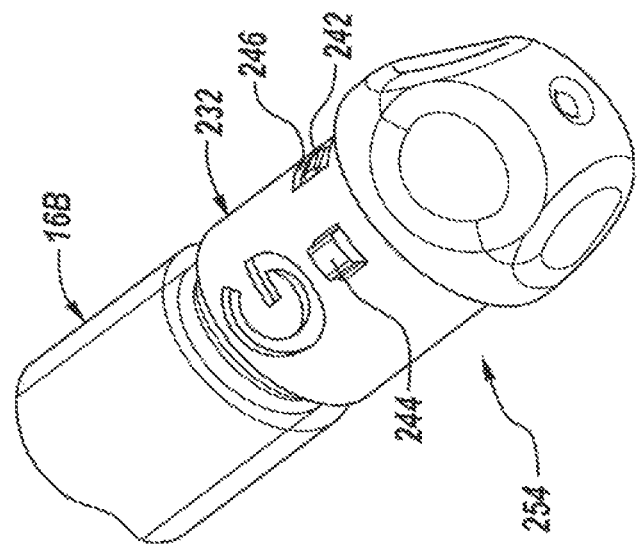
FIG. 16B is a perspective assembled view of the reservoir and coupler portion of FIG. 16A according to the teachings of the present invention.
Figure 16A:
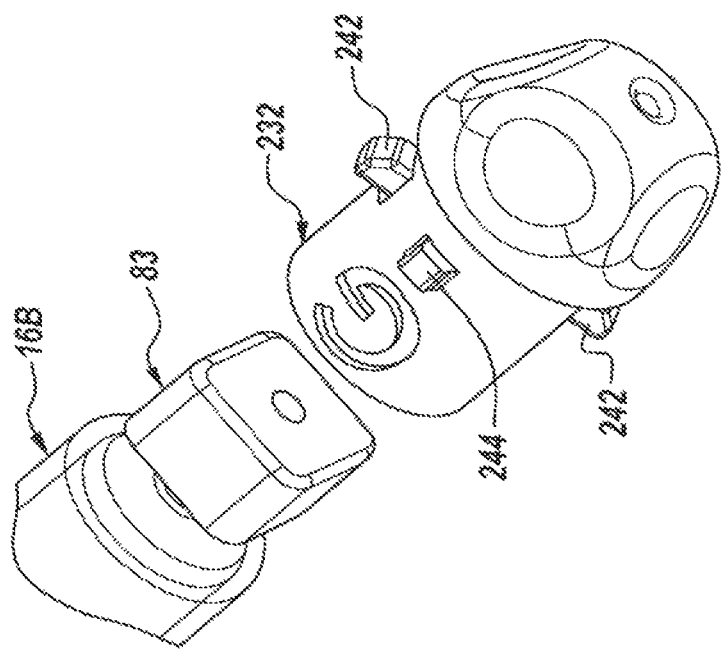
FIG. 16A is a perspective unassembled view of a second different reservoir having a different attached coupler having a selected feature element for coupling to a suitable coupler portion with a corresponding feature element to according to the teachings of the present invention.
Figure 17A:
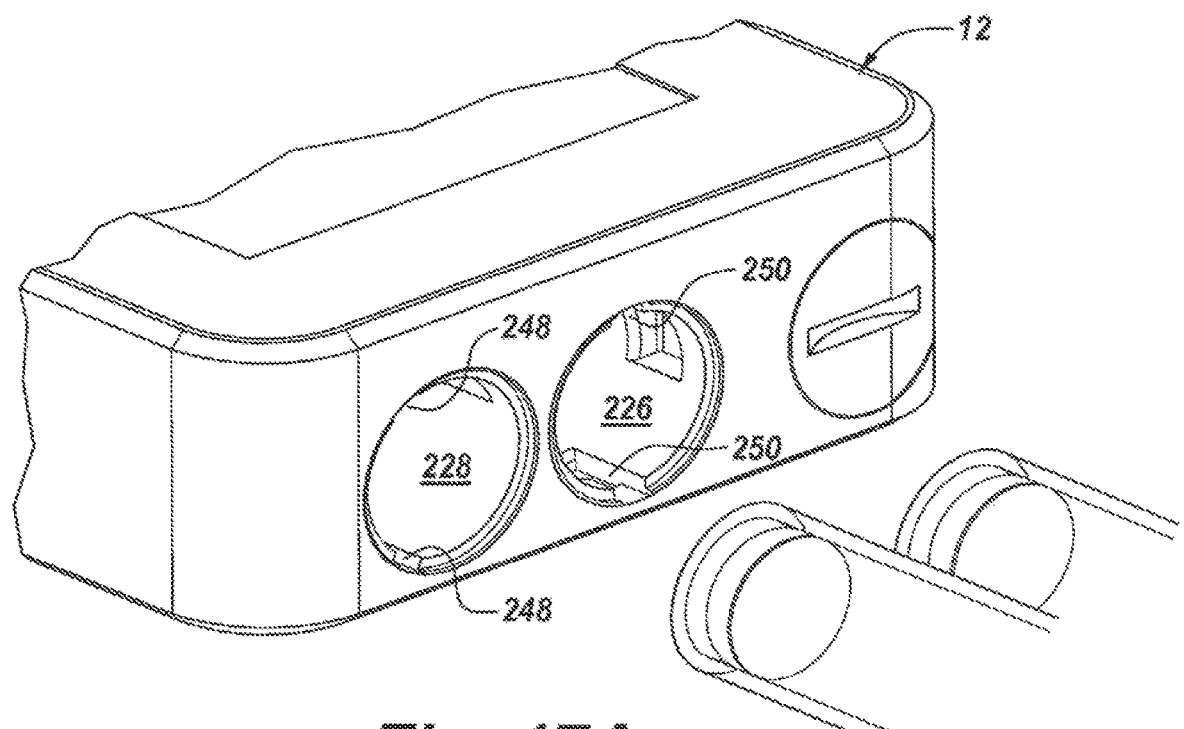
FIG. 17A is a perspective view of the infusion pump of the multi-medicament infusion system having selected feature elements formed on inlet/outlet ports according to the teachings of the present invention.
Figure 17B:
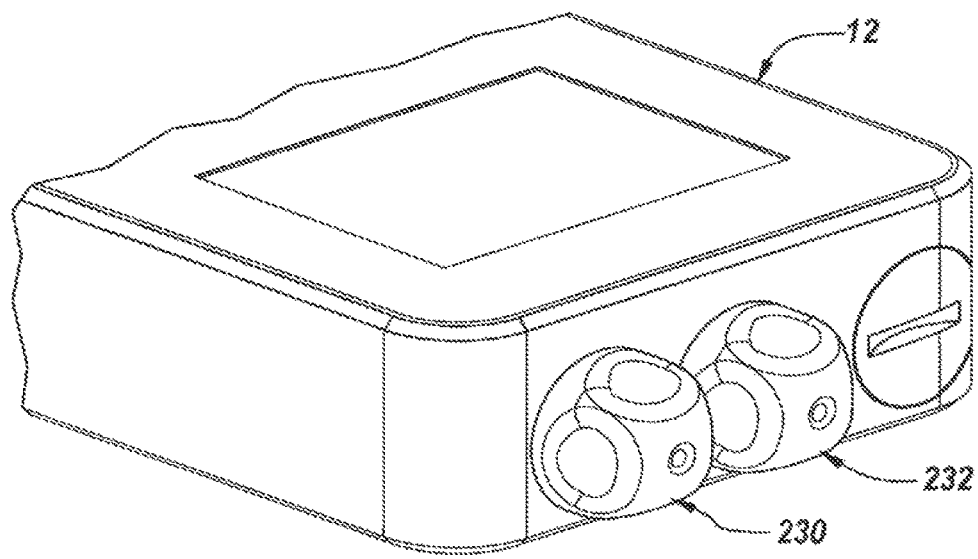
FIG. 17B is a perspective view of the infusion pump of the multi-medicament infusion system of FIG. 17A having selected reservoirs mounted in the ports with couplers having feature elements that are complementary to the feature elements formed on the coupler portions according to the teachings of the present invention.
Figure 18:
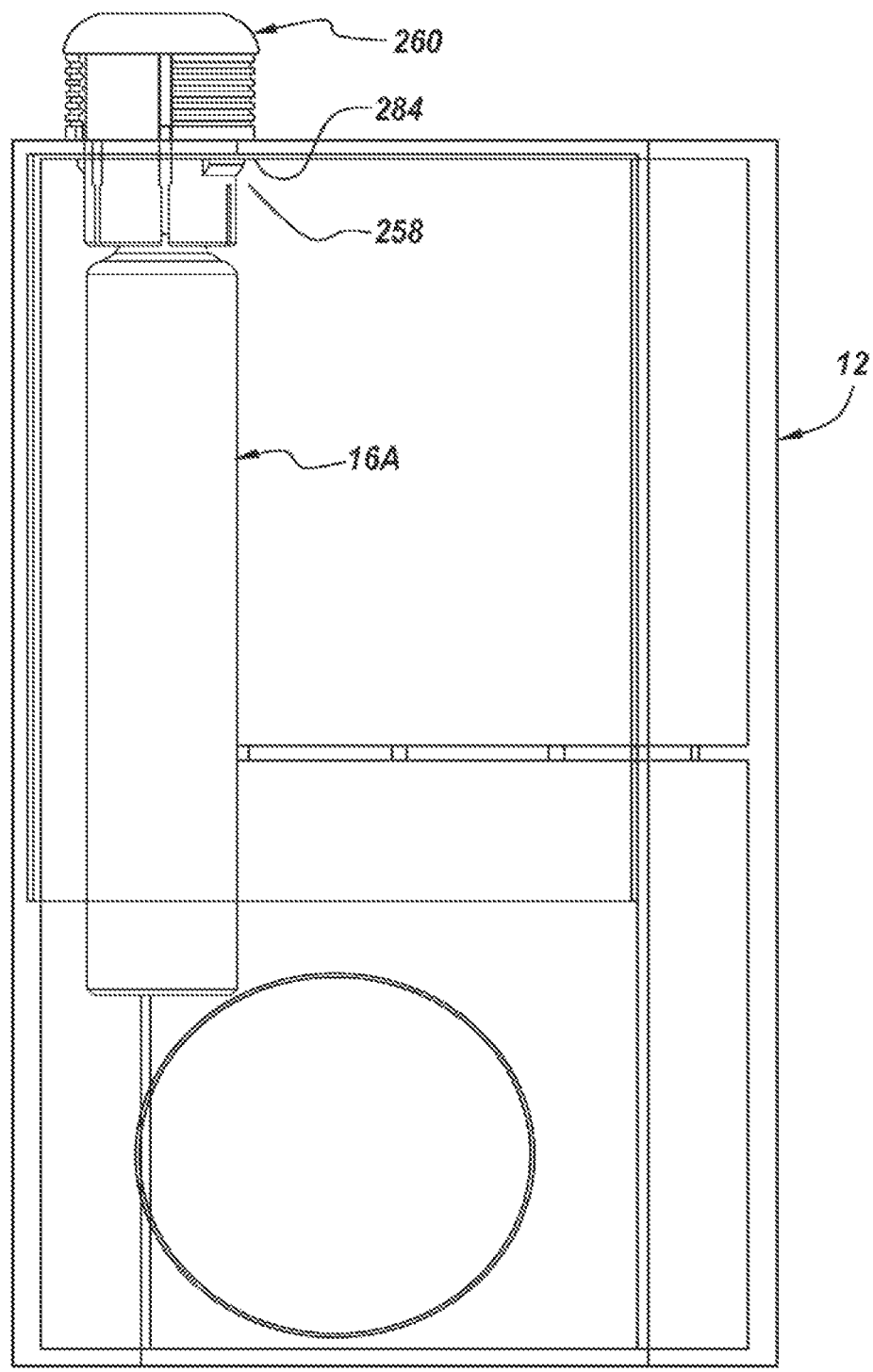
FIG. 18 is a schematic view of the infusion pump of for example FIGS. 17A and 17B illustrating another embodiment of a coupler suitable for connecting to a reservoir and mounting the reservoir within the pump according to the teachings of the present invention.

As illustrated in FIGS. 16A and 16B, the reservoir 16B includes a neck portion or swage 83 and the connector 232 is adapted to be coupled to the reservoir. The reservoir can contain any suitable medicament, and preferably contains glucagon. The swage can be constructed to have a feature element, here denoted as a generally square neck portion, that is adapted to seat within a corresponding and complementary shaped feature element, such as a chamber, formed in the underside of the connector housing. This is similar to the chamber formed in the connector 230 and illustrated in FIG. 22. Preferably, the feature elements help form a specific dedicated fluid pathway that helps prevent the mischanneling of medicaments and helps prevent the accidental administration of an incorrect medicament to the patient. Specifically, since the recess of the connector 232 is configured differently than the recess of the connector 230, the connector 232 is unable to be coupled to the insulin reservoir 16A. The connector is adapted to permanently or non-permanently capture the reservoir 16B. According to one practice, the connector 232 when mounted over the swage 83 of the reservoir 16B permanently captures or is coupled to the reservoir.

The illustrated connector 232 can also include one or more feature elements in the form of a plurality of surface features 242, 244 that extend outwardly from an outer surface of the connector housing 254. The surface features can include a plurality of tabs or detents, a subset of which is radially movable relative to the connector housing. According to one practice, the tabs 244 are also formed on the outer surface of the connector housing and are fixed in place. That is, the tabs 244 are not radially movable into the housing. The tabs 242 are configured as movable tabs that can be radially moved between an extended position, where the tabs extend outwardly from the connector housing outer surface 254 through the aperture 246, and a retracted position, where the tabs are primarily disposed within the chamber formed in the housing (similar to chamber 234). The tabs 244 can be placed on or extend outwardly from the connector housing outer surface at any suitable location and preferably are placed at positions that correspond with the location of feature elements formed on a corresponding inlet or port (e.g., inlet port) of the infusion pump housing, such as port 226. The operation and function of the movable tabs is similar or identical to that described above in connection with connector 230, and as illustrated for example in FIG. 22.

When the connector 232 is separately disposed relative to the reservoir, the tabs 242, 244 extend radially outwardly from the housing. When the connector is coupled to the reservoir 16B, the neck portion engages the movable tabs 242 or any other suitable cooperating structure to move the tabs 242 from the extended position into the retracted position. When coupled together in this manner, the connection between the reservoir and the connector can be non-permanent or permanent in nature, and the reservoir is preferably permanently retained or coupled to the connector. The tabs 244 can also be configured similar to the tabs 236, FIG. 22.

Once the reservoir 16B and the connector 232 are attached, the combined unit can be mounted within the corresponding port or inlet of the infusion pump 12. According to one practice, the inlet 226 functions as a combined inlet/outlet port or aperture. The inlet 226 preferably has one or more feature elements associated therewith. In the illustrated embodiment, the inlet 226 has a pair of keys or slots 250, FIG. 17A, formed in the inlet at locations that correspond to the locations of the fixed tabs 244 of the connector 232. As shown and not to be construed in a scope limiting way, the keys in the illustrated embodiment are formed at locations that are roughly opposite to each other. Hence, once the movable tabs 242 are disposed in the retracted position by the coupling together of the connector and the reservoir, the combined unit can be mounted within the inlet 226 since the fixed tabs 244 can be aligned with the keys 250 formed in the inlet. Further, the inlet 226 has feature elements formed at locations that are different than the locations of the fixed tabs 244 of the connector 232, thus preventing the reservoir 16B from accidentally being mounted in the incorrect inlet 228. This helps prevent the mischanneling of medicaments and the accidental administration of an incorrect medicament to the patient. Once the tabs 244 are aligned with the keys 250, the reservoir can be mounted within the inlet 226, FIG. 17B. The reservoir can be retained within the infusion pump 12 by rotating the connector when coupled to the inlet so that the tabs and the keys are no longer aligned.

Those of ordinary skill in the art will readily recognize that the inlets 226, 228 can have feature elements of any suitable design or shape, and any suitable number of feature elements can be provided on the connectors 230, 232 and at any suitable location.

According to another practice, the connector can be configured so that there is no rotation needed to attach the connector to the pump housing. An embodiment suitable for this purpose is illustrated in FIGS. 18-21. Like reference numerals denoting like or similar structure will be used throughout the various Figures and views. As shown, a connector 260 can be employed that is configured to couple to a reservoir, such as reservoir 16A, and to an inlet, such as port 258, of the infusion pump 12. The connector 260 has a housing 262 having an outer surface and an inner surface defining a chamber 264. The chamber is sized and configured to be able to be attached to a reservoir, such as for example reservoir 16A. The outer surface of the housing has a pair of opposed grip sections 266. The grip sections 266 are configured so as to have a series of ridges that enables a user to be able to securely grip and manipulate the connector 260 during use.

The connector housing 262 has a central opening or passage 268 that is adapted to accommodate a piercing element assembly 270. The piercing element assembly 270 includes a piercing element, such as a needle 272, that is in fluid communication with a channel or lumen 274. The lumen can form part of the multi-channel lumen assembly 18. The piercing element assembly 270 can be secured to the connector 260 and within the opening 268 by any suitable means known to those of ordinary skill in the art, such as by a suitable adhesive.

A bottom portion of the connector housing 262 has a connection assembly that includes a plurality of flexible retaining fingers or tabs 276. The retaining tabs have an inner surface that has a cam feature or surface 278 formed thereon. The cam feature is adapted to engage with a neck portion 83 of the reservoir 16A. As the neck portion is inserted into the opening or chamber 264 formed or defined by the retaining tabs 276 and the inner surface of the housing 262, the neck engages the cam surfaces and serves to flex or bend the retaining tabs in a radially outward direction as the neck travels axially along the cam surface. Once the neck portion of the reservoir passes the cam surface (i.e., disengages from the cam surface), the neck portion then seats in an annular groove 280. When the neck portion 83 is seated in the groove 280, the reservoir 16A is captured and retained by the connector 260.

Figure 19:
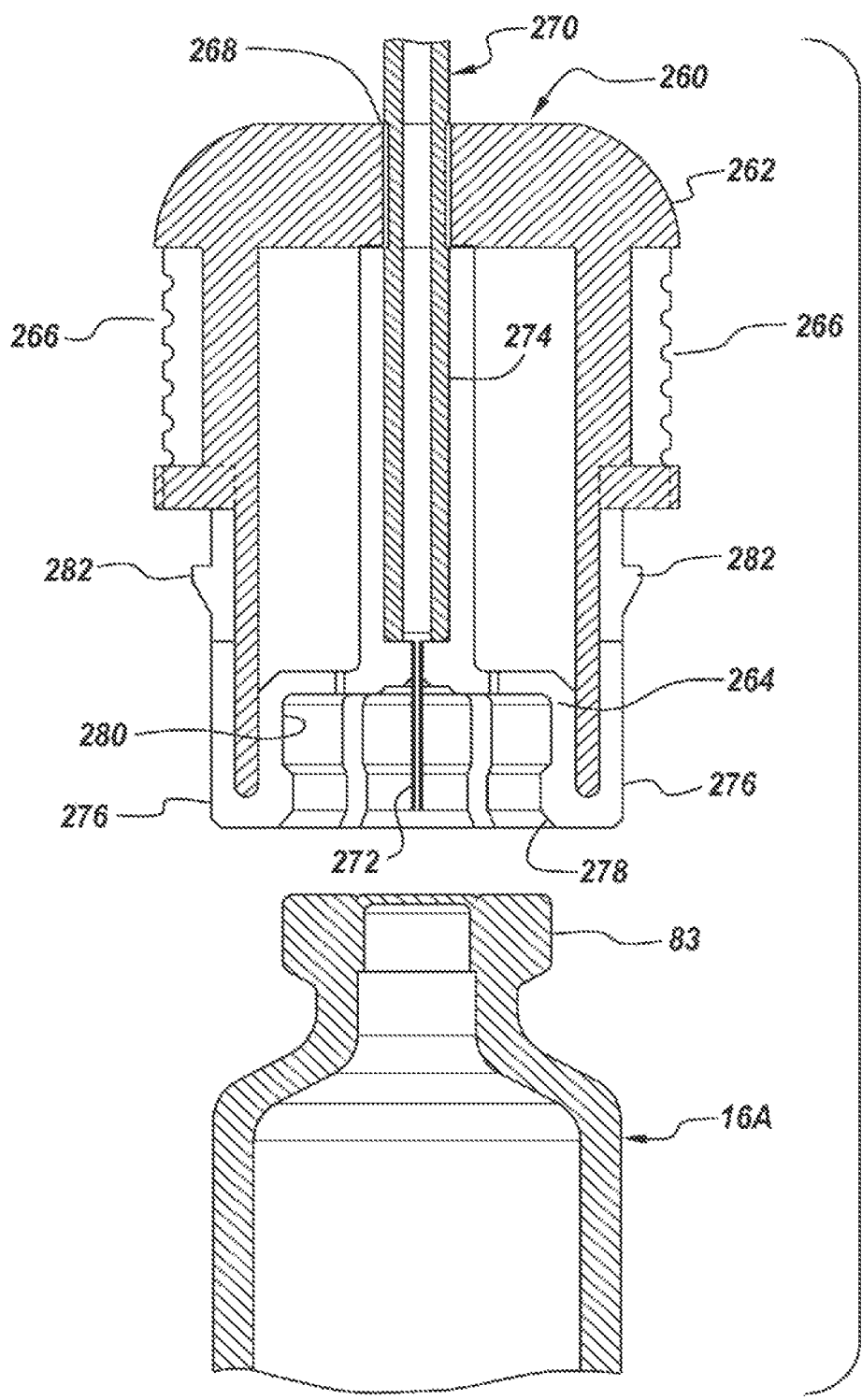
FIG. 19 is a schematic unassembled view of the coupler of FIG. 18 having a piercing element mounted therein according to the teachings of the present invention.
Figure 20:
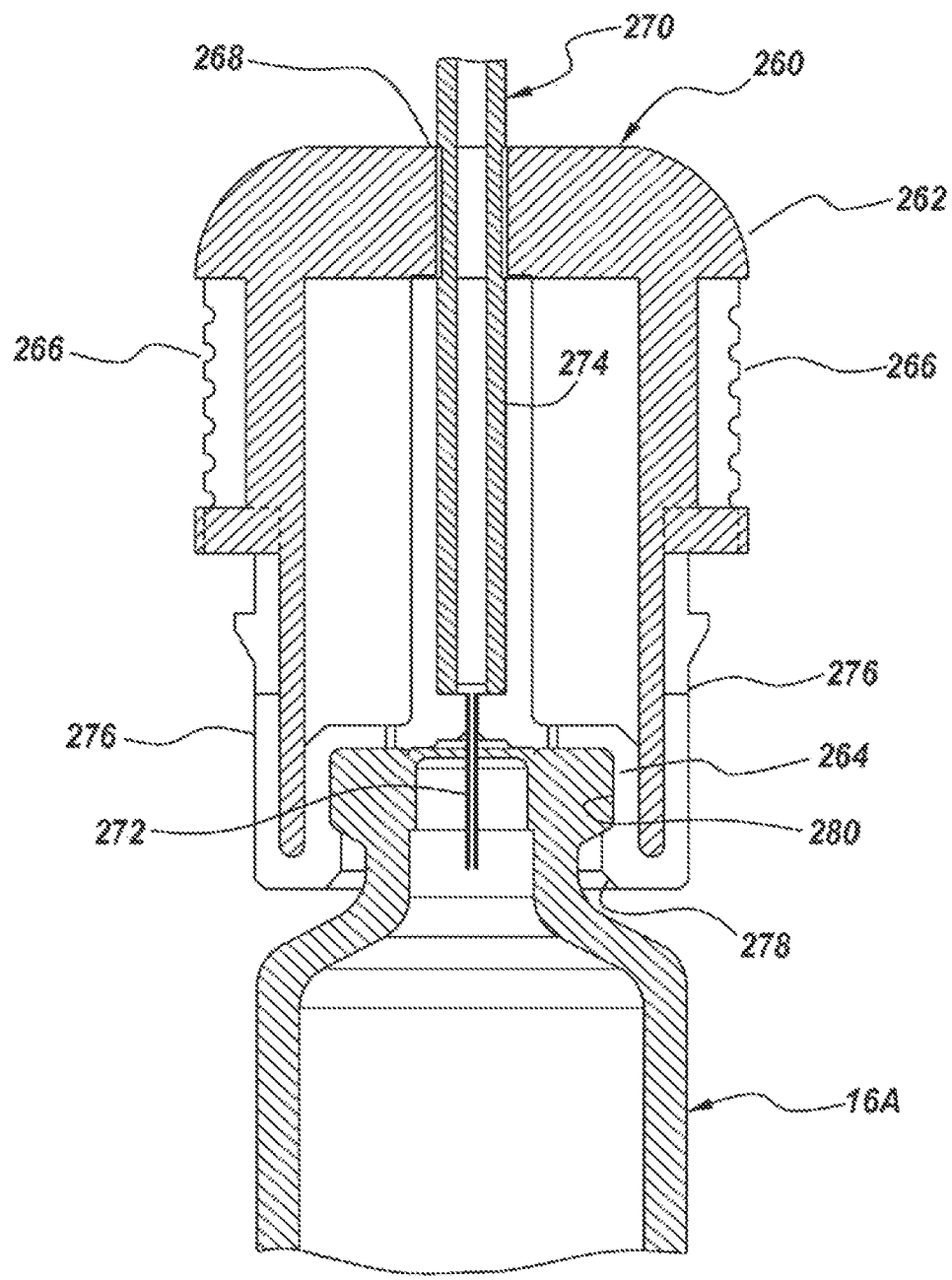
FIG. 20 is a schematic assembled view of the coupler and reservoir of FIGS. 18 and 19 according to the teachings of the present invention.
Figure 21:
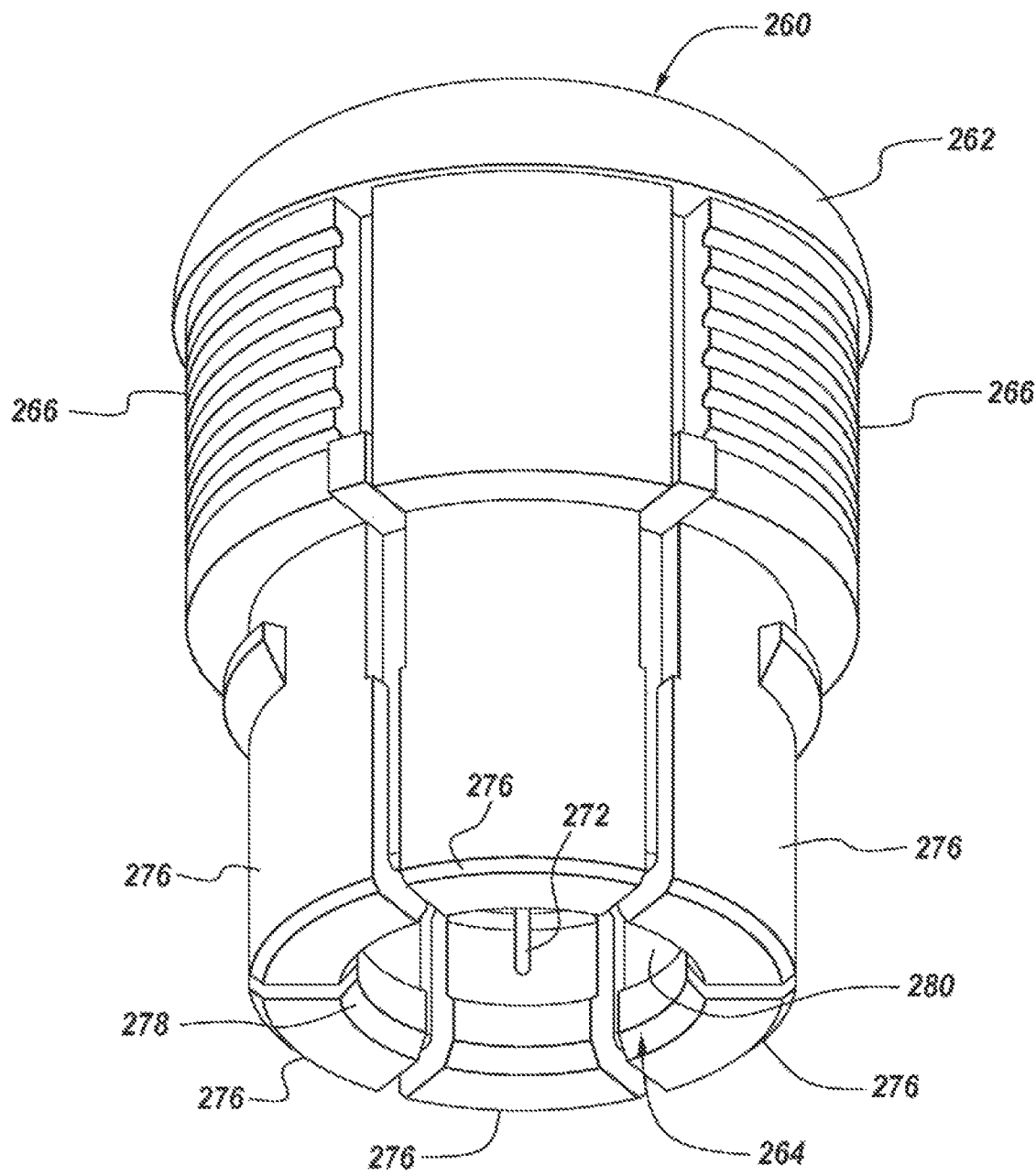
FIG. 21 is a schematic view of the coupler of FIGS. 18-20 according to the teachings of the present invention.

As further illustrated in FIGS. 19 and 20, when the connector 260 is separated and axially spaced from the reservoir 16A, the needle 272 does not engage the reservoir. When the neck portion 83, which typically includes a septum, is inserted into the chamber 264 of the connector housing 262, the needle 272 pierces the septum so as to be able to withdraw the medicament contained in the reservoir into the channel 274.

The retaining tabs 276 or a selected subset of the retaining tabs can have a cam or securing feature 282 formed on an outer surface thereof. The cam feature 282 is formed at a location that is axially spaced from the groove 280 so as to allow the retaining tabs to flex under selected conditions without allowing the reservoir 16A to disengage from the connector 260. The cam feature 282 has an angled surface, similar to the cam feature 278, that allows the connector 260 when inserted within the inlet 258 to squeeze or move the retaining tabs radially inwardly to allow the cam feature to travel along the axial length of the inlet. When fully inserted within the inlet 258, the cam features 282 engage an underside or undercut portion of the pump housing 284. This securing technique allows the connector to be attached to the pump housing without requiring rotation of the connector. To remove or disengage the connector 260 from the pump housing, the user applies radially inward pressure (i.e., squeezes) to the grip sections 266. The application of this radially inward force serves to disengage the cam feature from the undercut 284 by moving the cam feature radially inwardly and into the inlet. This allows the user to disengage the connector from the pump and thus remove the reservoir from the manifold formed within the pump housing.

In a multi-medicament infusion system according to the teachings of the present invention, the pump housing can include a pair of inlets as set forth above in connection with other embodiments. The inlets can have different feature elements relative to each other. According to one practice, the inlets can have different sizes relative to each other such that only a connector having the same size and hence having a corresponding or complementary surface feature can be coupled thereto. Additionally or alternatively, the reservoirs can include collars having different surface features, such as different sizes or shapes. These various feature elements help prevent the accidental mischanneling of medicament to the user by preventing the accidental loading of a selected medicament reservoir in the incorrect manifold.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween. Having described the invention, what is claimed as new and desired to be secured by Letters Patent is:

What is claimed is:

1. An infusion pump for delivering multiple medicaments to a patient, theinfusion pump comprising:
    a pump housing configured to house at least a first medicament reservoir and a second medicament reservoir;
    a first inlet port and second inlet port;
    a first chamber configured to receive the first medicament reservoir when inserted through the first inlet port and a second chamber configured to receive the second medicament reservoir when inserted through the second inlet port;
    a first pumping mechanism and a second pumping mechanism;
    wherein the first pumping mechanism is configured to actuate a plunger of the first medicament reservoir when the first medicament reservoir is inside the first chamber;
    wherein the second pumping mechanism is configured to actuate a plunger of the second medicament reservoir when the second medicament reservoir is inside the second chamber;
    a power source and a motor located within the pump housing;

wherein the first chamber and the second chamber are located within the pump housing and laterally spaced apart from each other;

wherein the first pumping mechanism and the second pumping mechanism are also located within the pump housing and laterally spaced apart from each other;

wherein the power source is located at a position within the pump housing and between the first chamber and the second chamber;

wherein the motor is located at a position within the pump housing and between the first pumping mechanism and the second pumping mechanism;

wherein the first inlet port is configured to engage a first reservoir connector having a feature element and the second inlet port is configured to engage a second reservoir connector having a feature element, wherein the feature element of the first reservoir connector is different than the feature element of the second reservoir connector;

wherein the first inlet port comprises a feature element and the second inlet port comprises a feature element, wherein the feature element of the first inlet port is different than the feature element of the second inlet port; and wherein the feature element of the first reservoir connector is complementary to the feature element of the first inlet port and the feature element of the second reservoir connector is complementary to the feature element of the second inlet port.

2. The infusion pump of claim 1, wherein the feature element of the first inlet port prevents proper docking of the first inlet port to the second reservoir connector.

3. The infusion pump of claim 1, wherein the feature element of the second inlet port prevents proper docking of the second inlet port to the first reservoir connector.

4. The infusion pump of claim 3, wherein the feature element of the first inlet port comprises a first slot that coincides with and is configured to engage a detent of the first reservoir connector and wherein the detent of the first reservoir connector prevents engagement of the first reservoir connector with the second inlet port.

5. The infusion pump of claim 1, wherein the feature element of the second inlet port comprises a slot that coincides with and is configured to engage a detent of the second reservoir connector and wherein the detent of the second reservoir connector prevents engagement of the second reservoir connector with the first inlet port.

6. The infusion pump of claim 1, wherein the first reservoir connector and the second reservoir connector are configured to respectively engage the first medicament reservoir and the second medicament reservoir and wherein the first reservoir connector and the second reservoir connector are configured to respectively engage with the first inlet port and the second inlet port so as to secure the first medicament reservoir and the second medicament reservoir in place.

7. The infusion pump of claim 1, wherein the pumping mechanism comprises a first lead screw configured to actuate a first plunger of the first medicament reservoir and wherein the pumping mechanism comprises a second lead screw configured to actuate a second plunger of the second medicament reservoir.

8. The infusion pump of claim 1, wherein the infusion pump further comprises a display screen.

9. The infusion pump claim 1, wherein the infusion pump is configured to communicate with a controller and wherein the controller receives a signal associated with a condition of the patient.

10. The infusion pump of claim 9, wherein the infusion pump is fully autonomous.

11. The infusion pump of claim 1, wherein the first medicament reservoir is configured to house a regulating agent and the second medicament reservoir is configured to house a counter-regulatory agent.

12. The infusion pump of claim 11, wherein the infusion pump is configured to communicate with a controller to control delivery of the regulating agent and the counter-regulatory agent.

13. The infusion pump of claim 12, wherein the regulating agent is insulin and the counter-regulatory agent is glucagon.

14. An infusion system for delivering multiple fluids to the patient, the system comprising the pump of claim 1.

15. The infusion system of claim 14, further comprising a multi-channel lumen assembly, the multi-channel lumen assembly comprising:
a first tube comprising a first inlet port and a first outlet port, the first inlet port configured to fluidly couple to the first inlet port of the infusion pump via the first reservoir connector; and
a second tube comprising a second inlet port and a second outlet port, the second inlet port configured to fluidly couple to the second inlet port of the infusion pump via the second reservoir connector.

16. The infusion system of claim 15, wherein the multi-channel lumen assembly comprises the first reservoir connector and the second reservoir connector.

17. The infusion system of claim 15, wherein the first tube and the second tube of the multi-channel lumen assembly are configured to be coupled together along at least a portion of the length of the assembly, wherein the first tube includes an outer surface having a surface feature associated therewith and the second tube includes an outer surface having a surface feature associated therewith, wherein the surface features of the first and second tubes are complementary in shape and configured to engage with each other to couple together the first and second tubes.

18. The infusion system of claim 15, further comprising an infusion set configured to deliver the first and second medicaments to a patient.

19. The infusion system of claim 18, wherein the infusion set comprises a first inlet port configured to fluidly couple to the first outlet port of the first tube and a second inlet port configured to fluidly couple to the second outlet port of the second tube.

20. The infusion system of claim 14, wherein the system comprises the first medicament reservoir and the second medicament reservoir.

21. The infusion system of claim 14, wherein the system comprises the first reservoir connector and the second reservoir connector and each have formed therein a piercing element for piercing the first medicament reservoir and the second medicament reservoir, respectively.

22. The infusion system of claim 18, wherein the piercing elements are touch proof.

* * * * *

UNITED STATES PATENT AND TRADEMARK OFFICE
CERTIFICATE OF CORRECTION

PATENT NO. : 11,357,911 B2
APPLICATION NO. : 17/122263
DATED : June 14, 2022
INVENTOR(S) : Edward R. Damiano, Kirk D. Ramey and Firas H. El-Khatib It is certified that error appears in the above-identified patent and that said Letters Patent is hereby corrected as shown below:

In the Claims

Claim 1, Column 32, Line 46, "theinfusion" should read --the infusion--.

Signed and Sealed this
Sixteenth Day of August, 2022

Katherine Kelly Vidal
*Director of the United States Patent and Trademark Office*